United States Patent [19]

Inouye et al.

[11] Patent Number: 4,643,969

[45] Date of Patent: Feb. 17, 1987

[54] NOVEL CLONING VEHICLES FOR POLYPEPTIDE EXPRESSION IN MICROBIAL HOSTS

[75] Inventors: Masayori Inouye, Setauket, N.Y.; Yoshihiro Masui, Osaka, Japan

[73] Assignee: The Research Foundation of State University of New York, Albany, N.Y.

[21] Appl. No.: 494,040

[22] Filed: Jul. 25, 1983

[51] Int. Cl.[4] .................... C12P 21/00; C12N 15/00; C12N 1/00

[52] U.S. Cl. .................... 435/68; 435/172.3; 435/317; 935/6; 935/29; 935/41; 935/48; 935/56; 935/72

[58] Field of Search .............. 435/68, 70, 71, 172.3, 435/172.1, 172.2, 317; 935/22, 27, 40, 41, 60, 73

[56] References Cited

U.S. PATENT DOCUMENTS 4,237,244 12/1980 Cohen et al. .................. 435/317 X

OTHER PUBLICATIONS

Masui et al, "Multipurpose Expression Cloning Vehicles in *E. Coli*", Date: 5/23/83.
Nakamura et al, *The EMBO Journal*, vol. 1, pp. 771–775, Jun. 1982.
Nakamura et al, *Journal of Molecular and Applied Genetics*, vol. 1, pp. 289–299, Jun. 1982.

*Primary Examiner*—Thomas G. Wiseman
*Assistant Examiner*—J. M. Gresser
*Attorney, Agent, or Firm*—Gottlieb, Rackman & Reisman

[57] ABSTRACT

Methods and compositions are provided for regulated expression of polypeptides in transformed bacterial hosts. A novel class of plasmid cloning vehicles includes a DNA sequence coding for the desired polypeptide (on an insertion site therefor) linked for transcriptional expression in reading phase with four functional fragments derived from the lipoprotein gene of *E. coli*. The plasmids further include a DNA sequence coding for a specific segment of the *E. coli* lac promoter-operator, which is positioned in the proper orientation for transcriptional expression of the desired polypeptide, as well as a separate functional *E. coli* lacI gene coding for the associated repressor molecule which can interact with the lac promoter-operator to prevent transcription therefrom. Expression of the desired polypeptide is under the control of both the constitutive promoter and the inducible promoter, although transcription from either promotor is normally blocked by the repressor molecule. However, the repressor can be selectively inactivated by means of an inducer molecule to permit transcriptional expression of the desired polypeptide from both promoter. The methods utilize such plasmids to introduce genetic capability into micro-organisms for the production of proteins, such as medically or commerically useful hormones, enzymes, immunogenic proteins, or intermediates therefor, but only in the presence of an appropriate inducer.

25 Claims, 33 Drawing Figures

FIG. 1

```
                                                                    TGGCTCTGCAGAGCA
                                                                    ACCGAGACGTCTCGT

-350                                    -300
ATCTGGCACACAAAGGTGACGTTGTAGTTATGGTTTCTGGTGCACTGGTACCGAGCGGCACTACTAACACCGCATCTGTTCACGTCCTGTAATATTGCTT
TAGACCGTGTGTTTCCACTGCAACATCAATACCAAAGACCACGTGACCATGGCTCGCCGTGATGATTGTGGCGTAGACAAGTGCAGGACATTATAACGAA

-250                                    -200
TTGTGAATTAATTTGTATATCGGCGCTTTTTTTATTTAATCGATAACCAGAAGCAATAAAAAATCAAATCGGATTTCACTATATAATCTCACTTTATCTA
AACACTTAATTAAACATATAGCCGCGAAAAAAATAAATTAGCTATTGGTCTTCGTTATTTTTTAGTTTAGCCTAAAGTGATATATTAGAGTGAAATAGAT

-150                                    -100
AGATGAATCCGATGGAAGCATCCTGTTTTCTCTCAATTTTTTTATCTAAAACCCAGCGTTCGATGCTTCTTTGAGCGAACGATCAAAAATAAGTGCCTTC
TCTACTTAGGCTACCTICGTAGGACAAAAGAGAGTTAAAAAAATAGATTTTGGGTCGCAAGCTACGAAGAAACTCGCTIGCTAGTTTTTATTCACGGAAG

-50                                     -1 +1                                              +50
CCATCAAAAAAATATTCTCAACATAAAAAACTTTGTGTAATACTTGTAAGGCTACATGGAGATTAACTCAATCTAGAGGGTATTAATAATGAAAGCTACT
GGTAGTTTTTTTATAAGAGTTGTATTTTTTGAAACACATTATGAACATTGCGATGTACCTCTAATTGAGTTAGATCTCCCATAATTATTACTTTCGATGA
                                           mRNA Start                                      MetLysAlaThr
                                                                                            1

+100                                               +150
AAACTGGTACTGGGCGCGGTAATCCTGGGTTCTACTCTGCTGGCAGGTTGCTCCAGCAACGCTAAAATCGATCAGCTGTCTTCTGACGTTCAGACTCTGA
TTTGACCATGACCCGCGCCATTAGGACCCAAGATGAGACGACCGTCCAACGAGGTCGTTGCGATTTTAGCTAGTCGACAGAAGACTGCAAGTCTGAGACT
LysLeuValLeuGlyAlaValIleLeuGlySerThrLeuLeuAlaGlyCysSerSerAsnAlaLysIleAspGlnLeuSerSerAspValGlnThrLeuA
             10                       20                        30

+200                                               +250
ACGCTAAAGTTGACCAGCTGAGCAACGACGTGAACGCAATGCGTTCCGACGTTCAGGCTGCTAAAGATGACGCAGCTCGTGCTAACCAGCGTCTGGACAA
TGCGATTTCAACTGGTCGACTCTGTGCTGCACTTGCGTTACGCAAGGCTGCAAGTCCGACGATTTCTACTGCGTCGAGCACGATTGGTCGCAGACCTGTT
snAlaLysValAspGlnLeuSerAsnAspValAsnAlaMetArgSerAspValGlnAlaAlaLysAspAspAlaAlaArgAlaAsnGlnArgLeuAspAs
 40                        50                        60                                    70

+300                                               +350
CATGGCTACTAAATACCGCAAGTAATAGTACCTGTGAAGTGAAAAATGGCGCACATTGTGCGACATTTTTTTTGTCTGCCGTTTACCGCTACTGCGTCAC
GTACCGATGATTTATGGCGTTCATTATCATGGACACTTCACTTTTTACCGCGTGTAACACGCTGTAAAAAAAACAGACGGCAAATGGCGATGACGCAGTG
nMetAlaThrLysTyrArgLys                                              Stop
                      78

+400
GCGTAACATATTCCCITGCTCTGGTTCACCATTCTGCGCTGACTCTACTGAAGGCGCATTGCTGGCTGCGGGAGTTGCTCCACTGCTCACCGAAACCGG
CGCATTGTATAAGGGAACGAGACCAAGTGGTAAGACGCGACTGAGATGACTTCCGCGTAACGACCGACGCCCTCAACGAGGTGACGAGTGGCTTTGGCC
```

5'-end:

```
        1                                     10                                      20                                      30                                      40
        G-C-U-A-C-A-U-G-G-A-U-U-A-A-C-U-C-A-A-U-C-U-A-G-A-G-G-U-A-U-A-A-A-U-A-A-U-G-A-A-A-G-C-U
                                                                                                          MET - LYS - ALA
                                                                                                           1
        50                                    60                                      70                                      80                                      90
        A-C-U-A-A-A-A-C-U-G-G-A-U-C-U-G-G-G-C-C-U-G-G-C-C-U-G-G-G-U-A-A-U-C-C-U-G-G-C-U-U-G-G-U
        THR - LYS - LEU - VAL - LEU - GLY - VAL - LEU - GLY - LEU - SER - THR - LEU - LEU - ALA - GLY
             5                    10                    15                     20
        100                                   110                                     120                                     130                                     140
        U-G-C-U-C-C-A-G-C-A-A-C-C-G-C-A-A-A-A-U-C-G-A-U-U-C-U-U-G-A-C-G-G-U-C-A-G-A-C-U-C-U-G
        CYS - SER - SER - ASN - ALA - LYS - ILE - ASP - SER - GLN - LEU - SER - ASP - VAL - GLN - THR - LEU
              25                    30                    35
        150                                   160                                     170                                     180                                     190                                     200
        A-A-C-G-C-U-A-A-A-A-G-U-U-G-A-C-C-A-G-C-U-G-A-C-A-G-G-U-A-A-C-G-C-U-U-C-C-G-A-C
        ASN - ALA - LYS - VAL - ASP - GLN - LEU - SER - ASN - ASP - VAL - ASN - ALA - MET - ARG - SER - ASP
              40                    45                    50
        210                                   220                                     230                                     240                                     250
        G-U-U-C-A-G-G-C-U-G-C-U-A-A-A-G-A-A-C-C-A-G-C-A-G-C-U-A-A-C-C-U-G-G-A-C-A-C
        VAL - GLN - ALA - ALA - LYS - ASP - ASP - ALA - ALA - ARG - ALA - ASN - GLN - ARG - LEU - ASP - ASN
              55                    60                     65                     70
        260                                   270                                     280                                     290                                     300
        A-U-U-A-G-G-C-U-A-A-A-A-U-A-C-C-G-C-A-A-G-U-A-A-C-C-U-G-U-G-A-A-A-A-A-A-U-G-G-C-G-G-C
        MET - ALA - THR - LYS - TYR - ARG - LYS
              75                    78
        310                                   320
        A-C-A-U-U-G-U-G-C-C-C-A-U-U-U-U-U-U-U-OH   :3'-end
```

NOVEL CLONING VEHICLES FOR POLYPEPTIDE EXPRESSION IN MICROBIAL HOSTS

DESCRIPTION

This invention was made with Government support under Contrast No. 5-R01-GM1904308 awarded by the National Institute of Health. The Government has certain rights in this invention.

TECHNICAL FIELD

This invention relates generally to the field of recombinant genetics, and specifically to a novel class of plasmid cloning vehicles with which exogenous genes may be expressed in transformed bacterial hosts.

As is well-known in the art, genetic information is encoded on double-stranded deoxyribonucleic acid ("DNA") molecules ("genes") according to the sequence in which the DNA coding strand presents the characteristic bases of its repeating nucleotide components. The four nitrogenous bases that characterize the two strands of DNA nucleotide are linked in complementary pairs by hydrogen bonds to form the double helix of DNA; adenine (A) is linked to thymine (T) and quanine (G) to cytosine (C). "Expression" of the encoded information involves a two-part process. According to the dictates of certain control regions in the gene, an enzyme ("RNA polymerase") may be caused to move along the DNA coding strands, synthesizing messenger ribonucleic acid ("mRNA") in a process called "transcription." The DNA coding strand typically includes signals, which can be recognized by RNA polymerase, for both initiation and termination of transcription. In a subsequent "translation" step, the cell's ribosomes, in conjunction with transfer-RNA, convert the RNA "message" into proteins or "polypeptides," which determine cell form and function. Included in the information transcribed by mRNA from DNA are signals for the initiation and termination of ribosomal translation, as well as signals specifying the identity and sequence of the amino acids which make up the polypeptide.

The DNA coding strand comprises long sequences of nucleotide triplets called "codons" in which the characteristic bases of the nucleotides in each triplet or codon encode specific bits of information. For example, three nucleotides read as ATG (adenine-thymine-guanine) result in an mRNA signal which is interpreted as "start translation," while termination codons TAG, TAA and TGA are interpreted as "stop translation." Between the initiation codon and the termination codon lies the so-called "structural gene," the codons of which define the amino acid sequence ultimately translated. That definition proceeds according to the well-established "genetic code" (e.g., Watson, J. D., *Molecular Biology Of The Gene*, 3rd ed. [New York: W. A. Benjamin, Inc., 1976]), which specifies the codons for the various amino acids. Since there are 64 possible codon sequences but only twenty known amino acids, the genetic code is degenerate in the sense that different codons may yield the same amino acid. However, the code is precise in that for each amino acid there is at least one codon, and in that each codon yields a single amino acid and no other. Thus, for example, all of the codons, TTT, TTC, TTA and TTG, when read as such, encode for serine and no other amino acid. It will be apparent that during translation the proper reading phase or reading frame must be maintained in order to obtain the proper amino acid sequence in the polypeptide ultimately produced.

The DNA sequence within the control region of a gene which mediates the initiation of transcription is termed the "promoter" of the gene, while the specific signal encoded in the DNA following the structural gene at which transcription ends is defined as the "transcription termination site." Although the mechanisms which underlie the initiation and termination of transcription are not completely understood, it is believed that the promoter provides the site at which RNA polymerase must bind in order to initiate transcription, and that the effectiveness or "strength" of a particular promoter or terminator signal is determined by the efficiency with which RNA polymerase can recognize and interact with these signals. This in turn depends in large part upon the particular base sequence of the DNA at or near these sites (see, e.g., Rosenberg, M., et al., *Ann. Rev. Genet.*, 1979 13, 319-353).

The control regions of some genes may also include DNA sequences which can be recognized by certain effector molecules, the action of which can positively or negatively influence the interaction between RNA polymerase and DNA and thereby further regulate gene expression at the level of transcription. The expression of genetic information by such genes may, for example, be inhibited in the absence of a given substance, and is therefore termed "inducible." On the other hand, there also exist many genes (such as the lipoprotein gene of the gram-negative bacterium *Escherichia coli* ["*E. coli*"]) whose control regions are not affected by effector molecules. The expression of genetic information by such genes is continuous during the lifetime of the cell, and is termed "constitutive." The control regions of such genes are generally comprised solely of a promoter signal and a terminator signal which immediately precede and follow, respectively, the DNA sequence to be transcribed.

The control regions cause mRNA synthesis to begin at a "transcription initiation site" located at or near the promoter, and to proceed until the transcription termination site is reached, producing an mRNA molecule of predetermined length with a base sequence complementary to the base sequence of the transcribed DNA. The DNA sequence between these two points defines not only the structural gene, the codons of which are ultimately translated for polypeptide expression, but also an "untranslated" region on either side of the structural gene.

Transcription therefore typically results in an mRNA molecule which carries a translatable RNA sequence, located between two untranslated regions. The untranslated region which precedes the structural sequence is known as the "5'-untranslated region," while the region which follows the structural signals is known as the "3'-untranslated region." As disclosed in detail hereinbelow, the DNA coding sequences for both of these untranslated regions, as well as the DNA coding sequences embodying the promoter signal and the terminator signal of certain genes, all of which may be referred to individually or collectively herein as "functional fragments" of those genes, may be effectively used in the creation of the novel cloning vehicles of the present invention.

As used herein, the term "cloning vehicle" defines a non-chromosomal double-stranded DNA molecule in "plasmid" form which can be replicated after being placed within a unicellular organism by a process called "transformation." An organism so transformed is called a "transformant." For present purposes, a "plasmid" is a circular non-chromosomal double-stranded DNA molecule derived from viruses or bacteria, the latter being termed "bacterial plasmids."

Advances in biochemistry in recent years have led to the construction of "recombinant" cloning vehicles in which, for example, plasmids are made to contain exogenous DNA. In particular instances a recombinant plasmid may include DNA that codes for polypeptides not ordinarily produced by the organism susceptible to transformation by the recombinant plasmid, and the exogenous DNA may in some cases comprise human genetic material. Typically, plasmids are cleaved to provide linear DNA having ligatable termini. These are bound to an exogenous gene having ligatable termini to provide a biologically functional moiety with a desired phenotypical property. The recombinant moiety is inserted into a micro-organism by transformation and transformants are isolated and cloned, with the object of obtaining large populations capable of expressing the new genetic information. Methods and means of forming recombinant cloning vehicles and transforming organisms with them have been widely reported in the literature, and generalized discussions of the subject appear in Cohen, S., *Scientific American* 233, 24–33 (July 1975), and in Gilbert, W., et al., *Scientific American* 242, 74–94 (April 1980). These and other publications alluded to herein are incorporated by reference.

A variety of techniques are available for DNA recombination, according to which adjoining ends of separate DNA fragments are tailored in one way or another to facilitate ligation. The latter term refers to the formation of phosphodiester bonds between adjoining nucleotides, through the agency of a catalytic enzyme such as T4 DNA ligase. Thus, DNA fragments with "blunt" ends may be directly ligated. Alternatively, fragments containing complementary single strands at their adjoining ends are advantaged by hydrogen bonding which positions the respective ends for subsequent ligation. Such single strands, referred to as "cohesive termini," may be formed by the addition of nucleotides to blunt ends using terminal transferase, or sometimes simply by "chewing back" one strand of a blunt end with an enzyme such as λ-exonuclease. Most commonly, however, such single strands may be formed by restriction endonucleases (also called restriction enzymes), which cleave the phosphodiester bonds in and around unique sequences of nucleotides of about 4–6 base pairs in length. Many restriction endonucleases and their recognition sequences are known, the so-called Eco RI endonuclease being one of the most widely employed.

Restriction endonucleases which cleave double-stranded DNA at unique sequences (e.g., at rotationally symmetric "palindromes") may leave cohesive termini. Thus, a plasmid or other cloning vehicle may be cleaved, leaving termini each comprising half of the restriction endonuclease recognition site. A cleavage product of exogenous DNA obtained with the same restriction endonuclease will have ends complementary to those of the plasmid termini. Alternatively, synthetic DNA comprising cohesive termini may be provided for insertion into the cleaved vehicle. To discourage rejoinder of the vehicle's cohesive termini pending insertion of exogenous DNA, the termini can be digested with alkaline phosphatase, providing molecular selection for closure incorporating the exogenous fragment. Incorporation of a fragment in the proper orientation relative to other aspects of the vehicle may be enhanced when the fragment supplants vehicle DNA excised by two different restriction endonucleases, and when the fragment itself comprises termini respectively constituting half the recognition sequence of the same two different endonucleases.

As a result of wide-ranging work in recent years is recombinant DNA research, the prior art includes a number of successful and commercially viable schemes to express functional polypeptide products such as insulin, somatostatin and human and animal growth hormone. The present invention relates to an improvement of one of those schemes.

BACKGROUND ART

In the earlier research efforts conducted by one of the present inventors, a group of recombinant bacterial plasmid cloning vehicles for expression of exogenous genes in transformed bacterial hosts was constructed, comprising a DNA insert fragment coding for the desired polypeptide, linked in reading phase with one or more functional fragments derived from any outer membrane protein gene of any gram-negative bacterium. In a preferred embodiment of these expression plasmids, the exogenous DNA codes for mammalian hormones, enzymes or immunogenic proteins (or intermediates therefor), the functional fragments are derived from the lipoprotein gene of *E. coli*, and the desired polypeptide is expressed in *E. coli* transformants. In a more preferred embodiment, the DNA sequence coding for the desired protein is linked with and is expressed under the control of four specific functional fragments associated with the *E. coli* lipoprotein gene, namely, the promoter, the 5'-untranslated region, the 3'-untranslated region and the transcription termination site of that gene.

These expression plasmids may also include a second promoter, preferably an inducible promoter and most preferably a DNA sequence consisting of 95 base pairs ("bp") and containing the *E. coli* β-galactosidase or "lac" promoter-operator, which is inserted immediately downstream of the lipoprotein promoter. This region serves not only as another transcription initiation site, but also as a repressor-binding site, thus working as a transcriptional "switch" for transcription initiated from the lipoprotein or "lpp" promoter, so that the exogenous DNA is expressed only in the presence of a "lactose inducer." When induced, the DNA coding for the desired polypeptide is transcribed from both promoters, thereby increasing the yield of the desired product over that obtained when expression is directed by the inducible lac promoter-operator alone. Accordingly, either constitutive or inducible gene expression may be achieved using these lpp gene cloning vehicles, provided that when inducible expression is desired, special *E. coli* strains are used as transformants, specifically, those which carry a mutant gene which overproduces the lactose repressor molecule.

Most preferably, each class of expression plasmids (both constitutive and inducible) includes three subclasses of plasmids, the members of each subclass containing one of three alternative insertion sites. In this manner, the selection of a particular plasmid or a particular sub-class of plasmids for gene expression can influence the ultimate location at which the expression product can be found and collected. Using one of these insertion sites, for example, the desired polypeptide can be expressed with a leader sequence located at the amino terminal, the leader comprising the signal peptide of the *E. coli* lipoprotein, such that the desired product may be secreted through the cytoplasmic membrane and the signal peptide removed in vivo by processes native to the transformant, to yield the exogenous gene product. On the other hand, using expression plasmids which contain one or the other of the two remaining insertion sites, the expression product can be expected to be found either in the cytoplasm of the cell, or in the cell wall.

While the plasmids of each sub-class share a common insertion site, they differ from one another in their individual reading frames. Thus, each sub-class comprises three plasmids, whose reading frames in effect differ by one base pair, enabling the selection of any desired reading frame for each insertion site and thereby facilitating the use of these expression vehicles with a wide variety of DNA insert fragments without the necessity of any direct modification of the reading frames of those fragments.

The earlier research efforts of one of the present inventors also provided a modification of the foregoing scheme, namely, a class of "auto-regulated" inducible expression cloning vehicles, each member of the class being otherwise identical with its analog in the class of inducible expression vehicles described above, but further including the DNA sequence coding for the repressor molecule capable of binding with the inducible promoter used in the vehicle. In the preferred embodiment, the autoregulated expression plasmids incorporate an intact, functional *E. coli* lacI gene for this purpose. Since the expression of the exogenous information in these cloning vehicles is regulated from within each cloning vehicle itself, a more effective transcriptional "switch" is provided, insuring that transcription is completely repressed in the absence of the appropriate inducer, without the necessity of utilizing special *E. coli* strains which overproduce the repressor molecule as transformants.

DISCLOSURE OF INVENTION

It has now been discovered that the yield of the desired expression product can be enhanced still further, without affecting the inducibility of the system, provided that the size of the DNA fragment carrying the lac promoter-operator region is varied slightly. Specifically, if a different, slightly longer DNA fragment is used, consisting of 105 bp but containing substantially the same, natural *E. coli* lac promoter-operator DNA sequence as used in the previous schemes described above, the amount of the desired polypeptide produced may increase dramatically.

Accordingly, in the present invention a class of inducible recombinant bacterial plasmid cloning vehicles for expression of exogenous genes in transformed bacterial hosts is provided, each plasmid comprising a DNA insert fragment coding for the desired polypeptide, linked with one or more functional fragments derived from the *E. coli* lpp gene and also linked in reading phase with the inducible *E. coli* lac promoter-operator carried on a particular 105 bp DNA fragment. Most preferably, each plasmid also includes an intact, functional *E. coli* lacI gene, providing inducible gene expression which is auto-regulated.

BRIEF DESCRIPTION OF DRAWINGS

The structure and function of the recombinant bacterial plasmids of the present invention, with which gene products such as human insulin may be expressed in bacterial transformants, is illustrated in the following specification, when taken in conjunction with the accompanying drawings wherein:

FIG. 1 is a schematic illustration of the 814-base pair DNA sequence encompassing the *E. coli* lipoprotein gene, in which the transcription initiation and termination sites are indicated by arrows (↕), and in which the 78 amino acid sequence of the proliproprotein deduced from the DNA sequence is also shown, written below the corresponding codons of the DNA coding strand;

FIG. 2 shows the complete 322-nucleotide sequence of the lipoprotein mRNA of *E. coli,* in which the amino acid sequence of the prolipoprotein deduced from the mRNA sequence is also indicated, written below the corresponding codons of the nucleotide sequence;

BEST MODE OF CARRYING OUT THE INVENTION

1. Summary Of Preliminary Research

Figure 3:
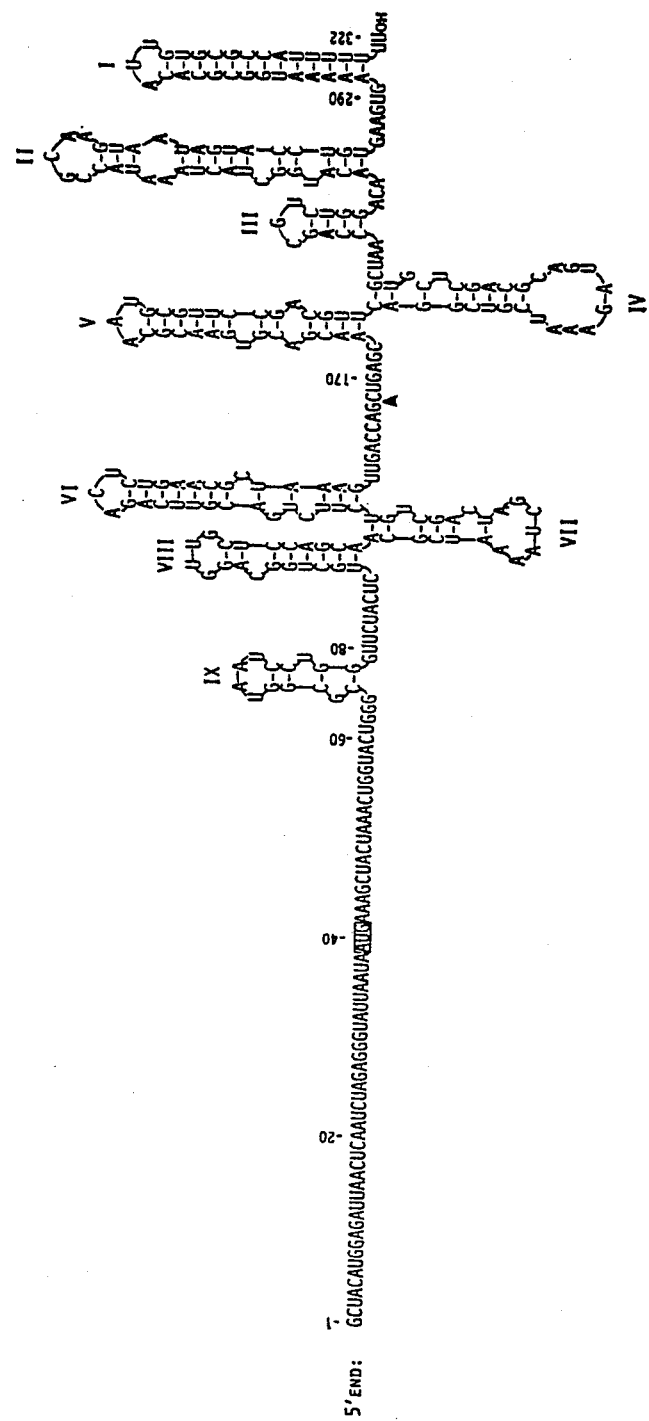
FIG. 3 illustrates the proposed secondary structure of *E. coli* lipoprotein mRNA, in which the translation initiation codon is boxed.

The earlier research of one of the present inventors has shown that as a class, the major outer membrane proteins of gram-negative bacteria are present in rather large quantities in each bacterial cell. For example, it has been found that the *E. coli* lipoprotein, which is one of the most extensively investigated membrane proteins, is also the most abundant protein in the cell in terms of numbers of molecules, there being approximately 700,000–750,000 lipoprotein molecules per cell. Since it has also been shown that there is only one structural gene for the lipoprotein of *E. coli,* extremely efficient machinery for lipoprotein gene expression, at the levels of both transcription and translation, is indicated. It is believed that the lipoprotein gene may be expressed at least ten times more efficiently than genes for ribosomal proteins. The presence of comparable quantities of other major outer membrane proteins in *E. coli*, such as the ompA protein, and the presence of comparable quantities of the major outer membrane proteins in other gram-negative bacteria, such as the lipoprotein of *Serratia marcescens*, indicate that these systems may also have very efficient machinery for gene expression. Thus, while the discussion herein may refer in large part to the lipoprotein system in *E. coli*, it is to be understood that similar results are to be expected from recombinant cloning vehicles which utilize the machinery for gene expression associated with any of the outer membrane protein genes of any gram-negative bacterium.

Although the mechanisms which are responsible for the highly efficient expression of the *E. coli* lipoprotein gene are not yet completely understood, it is believed that several factors must contribute to the abundance of lipoprotein molecules in a bacterial cell. As shown in FIG. 1, the DNA nucleotide sequence of the lipoprotein gene of *E. coli* has been determined, an analysis of which has revealed many unique properties associated with the expression of this gene.

In particular, it has been found that in comparison with other known promoter sequences of *E. coli* genes, the lipoprotein promoter region shows a most striking feature, namely, an extremely high A-T content, which is believed likely to be essential for highly efficient transcription of the lipoprotein gene. The segment of 261 bp preceding the transcription initiation site (from position −261 through position −1 as shown in FIG. 1) has a very high A-T content of 70%, in contrast with 53% for the transcribed region (or mRNA region) of 322 base pairs (positions +1 to +322), 44% for a segment of 126 bp after the transcription termination site (positions +323 to +449), and 49% for the average A-T content of the *E. coli* chromosome. The A-T content of the segment from position −45 to position −1, within which the nucleotide sequence of the lpp promoter appears to reside, is especially high (80%), and appears to be the highest among the *E. coli* promoter regions thus far sequenced. The A-T richness of the promoter sequence is considered to destabilize the helix structure of the DNA and thereby facilitate the RNA polymerase-mediated strand unwinding necessary for the initiation of transcription.

Apart from its A-T content, the lpp promoter also appears to contain heptanucleotide sequence at positions −15 through −9 (only eight base pairs distal to the transcription initiation site) which is homologous to the generalized "Pribnow box," as well as a dodecanucleotide sequence at positions −38 through −27 which is homologous to the generalized "RNA polymerase recognition site." The homology of these sequences is striking, in that the Pribnow box sequence of the lpp promoter has only one base mismatching with the generalized sequence, while the recognition site sequence shows a mismatch of only 5 out of 12 bases of the generalized sequence. The importance of the specific base sequences at these sites for efficient trascription is well-documented, in that mutants with enhanced promoter efficiency show increased homology of these regions with the generalized sequences.

Further analysis of the DNA sequence of FIG. 1 has revealed that besides having an extremely "strong" promoter, the lipoprotein gene also has an oligo-T transcription termination signal, located between positions +316 and +322, which is at least as efficient as all other *E. coli* transcription termination sites that have been studied. It is believed that this factor contributes to the overall efficiency of transcription by hastening the rate of mRNA production, and by limiting the size of the mRNA molecule which is transcribed from the DNA.

As shown in FIG. 2, the complete nucleotide sequence of the *E. coli* lipoprotein mRNA has also been determined, revealing that the mRNA has several unique features in its structure which appear to be important for efficient translation of the mRNA transcript. The mRNA consists of 322 nucleotides, 38 of which are in the 5'-untranslated region and 50 of which are in the 3'-untranslated region, leaving 234 nucleotides in the translated region which code for the lipoprotein precursor, or prolipoprotein. The mRNA sequence of FIG. 2 is complementary to the DNA sequence of FIG. 1, with the exception of the nucleotide at position 313 which is shown as C in FIG. 2 as determined by RNA sequencing, rather than A as determined by the DNA sequencing shown in FIG. 1. The reason for this difference is not known at present.

The lipoprotein mRNA has been shown to be unusually stable, and it has been proposed that this stability is probably attributable to the formation of extensive secondary structures within the molecule. As shown in FIG. 3, the mRNA can form nine stable "hairpin" stem-and-loop structures (designated by Roman numerals I–IX), the most stable of which (I) is in the 3'-untranslated region. These secondary structures may be responsible for the longer functional half-life which has been observed for the lipoprotein mRNA in comparison with other *E. coli* mRNAs, and may thereby increase the availability of this molecule for ribosomal translation.

Furthermore, although 68% of the total nucleotides in the mRNA molecule are involved in the formation of the hairpin structures shown in FIG. 3, it should be noted that in the first 64 nucleotides from the 5' end there are no stable hairpin structures, whereas between the 65th nucleotide and the 3' end, 85% of the nucleotides are involved in the formation of hairpin structures. This is significant because in the 5'-untranslated region (positions +1 to +38) there appear to be two extensive inverted repeat sequences of nucleotides which are thought to prevent the formation of secondary structures in this region, allowing the ribosome-binding site in this segment to be fully exposed to ribosomes, thereby facilitating the initiation of translation. Moreover, the rate of initiation of translation is probably further facilitated by the presence of two possible ribosome binding sites in this region of the molecule.

Finally, the presence of all three translation termination codons in the 3'-untranslated region of the mRNA (UAA, positions +273 to +275, UAG, positions +276 to +278, and UGA, positions +285 to +287 [see FIG. 2]), all three of which are in the same reading frame as the translatable or "coding" region of the mRNA, provides a unique "back-up" sequence of tandem terminators which probably contributes to the overall efficiency of translation by assuring proper termination of translation in a "fail-safe" manner.

The cumulative effect of these as well as other unique features of the lipoprotein mRNA is believed to result in very efficient translation of this genetic information in *E. coli* cells.

Apart from the efficiency of its expression, another important aspect of the lipoprotein of *E. coli* is that it is a "secretory" protein, i.e., it is produced from a precursor, which is then secreted across the cytoplasmic membrane and processed to the lipoprotein. Thus, translation of the lipoprotein mRNA transcript actually yields this precursor, called the prolipoprotein, which has a peptide extension or signal peptide at its amino terminus, consisting of 20 amino acid residues whose sequence has been determined, followed by the known 58 amino acid sequence of the lipoprotein. While the mechanisms involved in the secretion process are not yet well understood, the signal peptide is considered to direct the translocation in vivo of the prolipoprotein across the cytoplasmic membrane, in the process of which the peptide extension itself is removed, yielding mature lipoprotein.

It is believed that analogous elaboration processes are involved in the production of the major outer membrane proteins of all gram-negative bacteria. For example, an analysis and comparison of the DNA sequence of the *Serratia marcescens* ("*S. marcescens*") lipoprotein gene with that of the *E. coli* lpp gene has revealed striking homologies in the promoter region (84%) and in the 5'-untranslated region (95%). Moreover, the A-T content in the promoter region of the *S. marcescens* lipoprotein gene is extremely high (78%), as found in the case of the *E. coli* lipoprotein gene (80%). Furthermore, although the DNA sequence coding for the peptide extension of the prolipoprotein of *S. marcescens* differs somewhat from that of *E. coli*, the resultant alterations in the amino acid sequence do not change the basic properties of the signal peptide as proposed for the *E. coli* prolipoprotein and for other bacterial secretory proteins. In addition, the lipoprotein mRNA of *S. marcescens*, as deduced from the DNA sequence, seems capable of forming seven stable hairpin stem-and-loop structures. The existence of the lipoprotein in many different genera of gram-negative bacteria has now been confirmed, and it has been found that the *E. coli* lipoprotein mRNA hybridizes with DNAs from at least the following seven bacterial species (besides *S. marcescens*) in the family Enterobacteriaceae: *Shigella dysenteriae, Salmonella typhimurium, Citrobacter freundii, Klebsiella aerogenes, Enterobacter aerogenes, Edwardsiella tarda*, and *Erwinia amylovora*, thereby confirming a degree of homology of the lipoprotein gene between *E. coli* and other gram-negative bacteria. The expectation that similar properties will be found in recombinant plasmid cloning vehicles utilizing analogous and highly efficient machinery for gene expression derived from any gram-negative bacterium is believed justified by all of these as well as other findings.

The unique characteristics of the biosynthesis and assembly of the outer membrane proteins of gram-negative bacteria, as discussed above, make the lipoprotein genes and other major outer membrane protein genes of these organisms extremely attractive vehicles with which to control the expression of exogenous DNA insert fragments in bacterial transformants. In this application, the structure and function of several such cloning vehicles is described.

2. Strategy For Gene Expression

Figure 4:
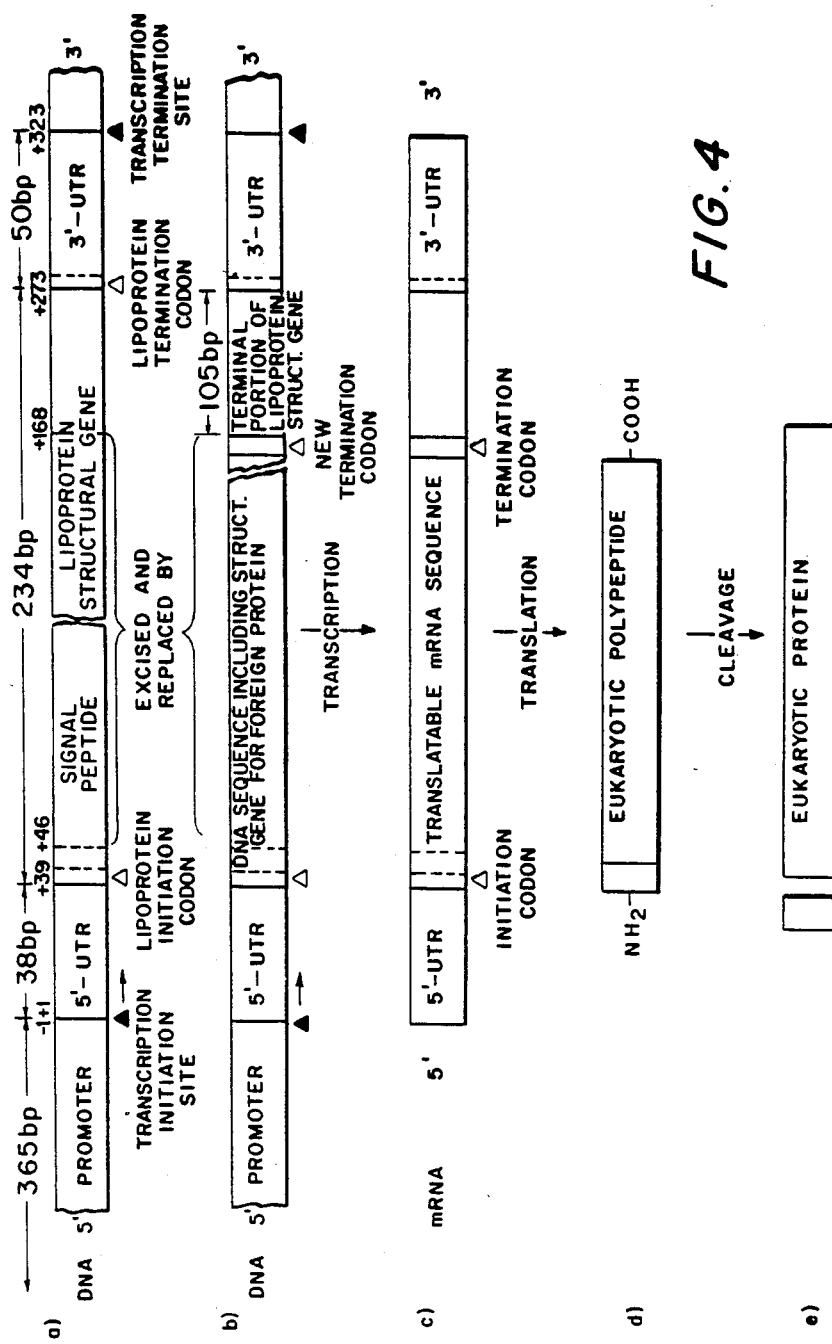
FIG. 4 is a schematic outline of the process by which a eukaryotic protein or other desired polypeptide may be expressed using recombinant plasmid cloning vehicles, in which the transcription initiation and termination sites are indicated by arrows (↕) and the translation initiation and termination sites are indicated by arrows (Δ)

It will be apparent from the foregoing discussion that a majority of the features which appear to be responsible for the efficient transcription and translation of the lipoprotein gene of *E. coli* reside in the functional fragments of the gene, namely, the promoter, the 5'-untranslated region, the 3'-untranslated region, and the transcription termination site, all of which are located either "upstream" or "downstream" of the lpp structural gene, as shown in FIG. 4, line a. Hence, by inserting a structural gene for a eukaryotic protein or other desired polypeptide in an expression plasmid containing various combinations of the foregoing functional fragments, and by transforming a bacterial host with such a plasmid, the transcription and subsequent translation of the structural gene has been made to take place under the control of those functional fragments.

For reasons which will be evident to those skilled in the art, it is particularly desirable and advantageous to utilize all of the foregoing functional fragments together in tandem in a single expression plasmid. By fusing the structural gene for the desired polypeptide at its 5' end to a DNA sequence comprising both the promoter and the 5'-untranslated region of the *E. coli* lpp gene (most preferably, this DNA sequence also includes the entire 260 bp A-T rich DNA segment preceding the transcription initiation site), highly efficient transcription is achieved by utilizing one of the strongest bacterial promoters, and highly efficient translation is achieved by utilizing a DNA sequence which can code for features which facilitate the initiation of translation, including the most effective ribosome binding site. Moreover, by fusing the structural gene at its 3' end to a DNA sequence comprising the 3'-untranslated region and the transcription termination signal of the *E. coli* lpp gene, the efficiency of transcription is believed to be further enhanced, avoiding transcriptional "read-through" (the synthesis of an unnecessarily long 3'-untranslated region in the mRNA) and more importantly, facilitating the rate of mRNA production. The stability of the mRNA molecule is also augmented by the formation of secondary structure in the 3'-untranslated region.

As described in detail hereinbelow, the secretory nature of the lipoprotein can be utilized to control yet another aspect of the expression of a eukaryotic protein or other desired polypeptide, namely, the location at which the expression product can be expected to be found. Depending upon the site within the lpp gene chosen for insertion of the exogenous DNA, the expression product can be expected to accumulate either within the cytoplasm of the transformant cell, within the periplasmic space, or in the cell's outer membrane.

FIG. 4 schematically illustrates a process wherein a transformant organism expresses a natural eukaryotic protein in accordance with the foregoing scheme. In the particular embodiment illustrated in FIG. 4, the structural gene for the eukaryotic protein is inserted within the signal peptide of the lpp gene, several base pairs after the translation initiation codon and downstream of certain functional fragments (namely, the promoter and the 5'-untranslated region) normally associated with the lipoprotein gene. As will be seen by comparing line a with line b in FIG. 4, the orientation of these functional fragments is identical to the natural orientation of these elements in the lipoprotein gene, while the exogenous DNA insert fragment supplants most of the signal peptide as well as a portion of the structural region of the lipoprotein gene.

As shown in FIG. 4, line b, the foreign gene is linked at its 3' end to an extra translation termination codon, which is in turn fused to the remainder of the lipoprotein structural gene. This is linked still further downstream in the normal manner to the 3'-untranslated region of the lpp gene, which ends with the transcription termination site. As can be seen by again comparing line a with line b in FIG. 4, the functional fragments which follow the DNA insert fragment are essentially identical to those which are present normally in the lipoprotein gene.

The 3'-untranslated region derived from the lpp gene codes for an mRNA sequence capable of forming the stem-and-loop structure designated by the numeral I in FIG. 3, which, as discussed previously, is the most stable secondary structure in the lipoprotein mRNA. However, the recombinant DNA sequence depicted schematically in FIG. 4, line b, also includes a terminal portion of the lipoprotein structural gene consisting of 105 base pairs starting with position +168 (this position is designated by the arrow (↓) in FIG. 3). This region is chosen so that the stability of the mRNA transcript can be further enhanced by including four additional stem-and-loop structures (designated by the numerals II, III, IV and V in FIG. 3), without unduly increasing the size of the mRNA molecule produced. However as set forth below, this region is not ultimately translated.

Transcription of the recombinant DNA sequence illustrated in FIG. 4, line b, yields an mRNA sequence which is illustrated schematically in FIG. 4, line c. It will be seen that this sequence contains the 5'-untranslated region and the 3'-untranslated region, both of which are normally associated with the production of the lipoprotein. However, the mRNA also incorporates a region coding for the eukaryotic protein, preceded by a region which codes for a short segment of the signal peptide of the prolipoprotein, and followed by another region which codes for a segment of the lipoprotein. The latter region ultimately will not be translated, however, due to the insertion of the extra termination codon (designated by an arrow (Δ) in FIG. 4, lines b and c) at the 3' end of the eukaryotic structural gene. Following translation, a polypeptide is produced comprising several extraneous amino acid residues, followed by the amino acid sequence of the desired eukaryotic protein (see FIG. 4, line d). This conjugate expression product can be expected to accumulate within the cytoplasm of the cell, because secretion can not occur in the absence of a complete signal peptide. However, for certain proteins, the expression product can be purified from the cytoplasm in a known manner, and the superfluous protein fragment may then be separated and removed from the natural protein product by known techniques (see FIG. 4, line e), yielding the desired polypeptide which may then be stored for future use.

Alternatively, the DNA sequence coding for the extraneous amino acids can be excised from the expression plasmid in a known manner prior to transformation of the bacterial host, such that the expression product corresponds exactly with the desired foreign protein and may be purified by known techniques.

In an alternative embodiment of the foregoing scheme, the same functional fragments are used, but the DNA sequence coding for the desired polypeptide is inserted further downstream, following the last codon of the signal peptide (i.e., at or near the signal peptide cleavage site). It will be apparent to those skilled in the art that in this embodiment, the orientation of the functional fragments is once again identical to the natural orientation of these elements in the lipoprotein gene, allowing full advantage to be taken of the efficiencies of transcription and translation associated therewith, including the enhanced stability of the mRNA transcript attributable to the incorporation of four additional stem-and-loop structures, as described hereinabove.

The transcription and ultimate translation of such a recombinant DNA sequence proceeds in a manner analogous to that described hereinabove and illustrated in FIG. 4, except that following translation, a polypeptide is produced comprising a signal peptide corresponding to the signal peptide of the prolipoprotein, followed by the amino acid sequence of the desired eukaryotic protein. This precursor product can then be secreted across the cytoplasmic membrane under the control of the signal peptide, in the process of which the peptide extension itself may be recognized and removed by enzymatic action natural to the E. coli transformant cell, yielding a product consisting of the natural eukaryotic protein, perhaps with several extraneous amino acid residues at the amino terminus which can be removed as discussed hereinabove. This product accumulates initially in the periplasmic space, and may ultimately pass through the cell's outer membrane and into the culture medium provided that certain E. coli transformant strains are used, as set forth in more detail hereinbelow.

Using this approach, the accumulation of a large amount of the expression product inside the cell is less likely to interfere with cell growth, because the eukaryotic protein is linked with a signal peptide which is natural to the cell. Furthermore, the presence of the signal peptide may protect the foreign protein from possible degradative action inside the cell, which could otherwise lower the protein yield and could also cause contamination of the foreign protein by heterogenous degradative products, resulting in purification difficulties.

In yet another alternative embodiment of the foregoing scheme, the same functional fragments are again used, but the DNA sequence coding for the desired polypeptide is inserted still further downstream, for example, as illustrated herein, following the codon for the eighth amino acid residue after the signal peptide cleavage site. It will be apparent to those skilled in the art that in this embodiment, the orientation of the functional fragments is once again identical to the natural orientation of these elements in the lipoprotein gene, allowing full advantage to be taken of the efficiencies of transcription and translation associated therewith, including the enhanced stability of the mRNA transcript attributable to the incorporation of four additional stem-and-loop structures, as described hereinabove.

The transcription and ultimate translation of such a recombinant DNA sequence proceeds in a manner analogous to that described hereinabove and illustrated in FIG. 4, except that following translation, a polypeptide is produced comprising a signal peptide of 20 amino acid residues, corresponding to the signal peptide of the prolipoprotein, followed by eight amino acid residues corresponding to the first eight amino acid residues of the mature lipoprotein, followed by the amino acid sequence of the desired eukaryotic protein. As with the embodiment previously described, this precursor product may be translocated naturally across the cytoplasmic membrane, in the process of which the signal peptide can be recognized and removed. However, the product may not accumulate in the periplasmic space; instead, the eight amino acids corresponding to the lipoprotein can be recognized by processes native to the transformant, and the expression product may then be processed further and inserted into the outer membrane of the cell in a manner analogous to the normal insertion of the lipoprotein into the outer membrane. If, as expected, only the first eight amino acid residues of the expression product corresponding to the lipoprotein are actually bound into the outer membrane, then the remainder of the expression product, consisting of the amino acid sequence of the eukaryotic protein or other desired polypeptide, will protrude from the outer membrane, such that, for certain proteins, the membrane may be isolated and the desired protein purified from the membrane easily.

It will therefore be evident to those skilled in the art that by constructing a plasmid cloning vehicle according to the present invention with one or another of the three insertion sites described above, and by using such a plasmid to express as exogenous gene product, the location of that product can be predicted with a reasonable degree of certainty, and the appropriate methods for isolating and purifying that product will thereby be suggested. The choice of insertion site will often be dictated by the identity and structure of the desired polypeptide itself, especially if the method of purification most appropriate for that product is known.

In order to facilitate still further the expression of a wide variety of exogenous DNA fragments using the cloning vehicles of the present invention, a short polynucleotide sequence containing the recognition sites for the Eco RI, Hind III and Bam HI restriction enzymes can be incorporated at the insertion site in each expression plasmid. This allows additional flexibility, in that six different types of restriction fragments can be inserted into each plasmid according to the straightforward and well-known techniques described hereinabove. Thus, DNA insert fragments tailored to have any one of the following pairs of cohesive termini can be readily used with the present invention: Eco RI-Eco RI, Hind III-Hind III, Bam HI-Bam HI, Eco RI-Hind III, Eco RI-Bam HI and Hind III-Bam HI.

As mentioned hereinabove, the expression of genetic information is termed inducible if transcription cannot be initiated in the absence of a certain molecule. Inducible gene expression is exemplified in nature by the *E. coli* lac promoter-operator, which controls the production of β-galactosidase, an important enzyme in lactose digestion. Normally, the expression of this gene is "switched off" by the presence of a lactose repressor, which binds to the lac promoter-operator, preventing interaction between RNA polymerase and the promoter sequence and thereby inhibiting transcription (and subsequent translation) of the β-galactosidase structural gene. In the presence of lactose, however, the repressor molecule is removed from the DNA and the gene is "switched on," allowing transcription to proceed until a sufficient quantity of the β-galactosidase enzyme is produced to digest the lactose, after which the repressor again "switches off" the gene.

The constitutive lpp gene cloning vehicles described hereinabove have been made inducible by inserting the lac promoter-operator downstream of the lpp promoter, but upstream of the exogenous DNA insert fragment. The lac promoter-operator region is carried on a 95 by DNA fragment derived from the natural *E. coli* lacZ gene. In this configuration, transcription of the foreign DNA from either promoter is blocked by the repressor molecule and cannot proceed in the absence of a substance, termed a "lactose inducer," which for present purposes is a molecule that reacts with and alters the lactose repressor molecule such that the repressor molecule can no longer bind to the lac promoter-operator. When induced with lactose or with a synthetic inducer such as isopropyl-β-D-thiogalactoside (hereinafter "IPTG"), the foreign DNA can be transcribed from both the lpp and lac promoters independently, allowing approximately five to ten times higher gene expression than would occur using the lac promoter alone.

The inducible lpp gene cloning vehicles described above have, in turn, been modified for auto-regulation by inserting within each plasmid a functional *E. coli* lacI gene. In this manner, the 1:1 ratio between lactose repressor genes and lac promoters, which is normally present in wild-type *E. coli* cells, can be maintained in transformants chosen for expression of the desired polypeptide. Accordingly, such transformants need not carry and need not be provided with the F-prime factor thought necessary, but found to be unsatisfactory to repress the expression of the desired product by microorganisms transformed with the inducible expression plasmids described hereinabove.

The inducible and auto-regulated inducible lpp gene cloning vehicles previously constructed all utilize a lac promoter-operator fragment consisting of 95 bp, corresponding to the DNA segment lying between position −59 and position +36 of the natural lacZ gene, plus an additional 8 bp attributable to linker molecules which are added to facilitate insertion of the fragment into the expression plasmid, for a total fragment length of 103 bp. It has now been determined that an unexpected increase of up to 100% in expression of the desired product can be obtained if a different DNA fragment is used as the source of the lac promoter-operator. The latter fragment consists of 105 bp, corresponding to the DNA segment lying between position −40 and position +65 of the lacZ gene, plus the same additional 8 bp derived from the linker molecules which are used to tailor the fragment for easy insertion into the expression plasmid, for a total fragment length of 113 bp. The latter fragment, which incorporates 19 fewer bp upstream of the promoter-operator region than the 95 bp fragment used previously, but also includes 29 additional bp downstream of the promoter-operator region, will be referred to generally herein as the "113 bp lac promoter-operator fragment" or simply the "113 bp lac fragment." The reasons for the differences in activity between the 95 bp lac fragment and the 113 bp lac fragment are not known at present.

It is to be understood that all of the desirable features described hereinabove in connection with the inducible and auto-regulated inducible lpp gene expression plasmids constructed previously may be incorporated with equal advantage in the inducible and auto-regulated inducible lpp gene expression plasmids of the present invention. These include the efficiencies of transcription and translation usually associated with the four specified functional fragments of the lpp gene, the enhanced stability of the mRNA transcript attributable to the incorporation of the four additional stem-and-loop structures normally associated with the mRNA transcript of the terminal portion of the lipoprotein structural gene, the provision of three different insertion sites for the foreign DNA to control the location at which the expression product can be expected to be found, and the incorporation of Eco RI, Hind III and Bam HI restriction enzyme recognition sequences at the exogenous DNA insertion site in each plasmid to facilitate the expression of a wide variety of DNA insert fragments.

It is to be understood also that virtually any structural gene coding for a desired polypeptide, including mammalian and human hormones, enzymes and immunogenic proteins (or intermediates therefor), may be expressed using the recombinant plasmids of the present invention. Examples of such proteins includes A-chain insulin, B-chain insulin, proinsulin, growth hormone, somatostatin, interferon and trypanosome antigen, but the invention is not confined to these exemplary products.

3. The Transformant

In the preferred embodiment of the present invention, the auto-regulated inducible recombinant cloning vehicles utilizing the 113 bp lac promoter-operator fragment and incorporating the gene for the desired eukaryotic protein or other polypeptide, are used to transform particular E. coli strains as hosts for cloning and for subsequent production of the protein. The host cell strains used will be chosen to have a "deletion mutant" in the lpp gene, so that the host cells cannot produce the lipoprotein. The use of a deletion mutant strain as the transformant is thought to stimulate the production of a large amount of the foreign protein, since the entire capacity of the host cells to produce the lipoprotein is thereby channelled towards production of the foreign protein. Furthermore, secretion of the foreign protein across the cytoplasmic membrane is facilitated in lpp-defective host cells, since the secretion sites in the membrane which are intended to be used for lipoprotein secretion are instead available for secretion of the foreign protein.

The use of the lpp-defective cells is especially beneficial when the gene coding for the foreign protein is inserted at or near the lipoprotein signal peptide cleavage site. This is because such cells are known to be "leaky", i.e., proteins secreted across the cytoplasmic membrane of such cells ultimately "leak" out into the culture medium through the outer membrane of the cell. This is believed to be desirable not only because release of the desired foreign protein into the culture medium may in some cases allow easier insolation and purification of the foreign protein than would be possible if the foreign protein remained inside the cell, but also because the foreign protein would otherwise accumulate in the periplasmic space, perhaps leading to undesirable interference with normal cellular activities or cell growth. Secretion of the desired eukaryotic gene product outside the cell may also avoid degradation of that product into smaller fragments by proteolitic enzymes which are normally present within the cell.

While the present invention also contemplates the construction and use of inducible (but not auto-regulated) cloning vehicles utilizing the 113 bp lac fragment, these are not preferred for exogenous gene expression because even more specialized E. coli strains are needed for use as transformants, specifically, those which can overproduce the lactose repressor molecule. In wild-type E. coli cells, only about 10 copies of the lactose repressor molecule are maintained in each cell at any one time, which is just enough to repress (i.e., inhibit the expression of) the one lacZ gene normally contained in the cell. This is insufficient, however, to block the expression of the exogenous DNA cloned in one of the inducible expression plasmids of the present invention, since 10 to 20 copies of the cloning vehicle, each containing an active lac promoter, may exist in each cell at a given time. Therefore, much larger amounts of the lactose repressor are needed, and for this purpose, the strain required for transformation is preferably a special E. coli strain JA221/F' lacI$^q$ lac$^+$ pro$^+$, which carries the mutant lacI$^q$ gene. The lacI$^q$ gene is a mutant of lacI, the "normal" gene coding for the lactose repressor. The mutant gene overproduces the lactose repressor, providing about 100-150 molecules/cell at any given time. The lacI$^q$ gene is carried on the plasmid F-prime in this E. coli strain.

The fact that this scheme necessitates expression of the desired polypeptide in transformants carrying the plasmid F-prime gives rise to certain disadvantages. First of all, the class of recipients for the inducible expression plasmids is inherently limited to those E. coli strains which carry the lacI$^q$ gene, since strains which lack this gene would not produce enough of the lactose repressor and would therefore continuously generate the desired expression product. Secondly, the F-prime plasmid is a sex factor which causes E. coli cells to conjugate, resulting in transfer of the F-prime plasmid from one cell to another. Therefore, the use of E. coli strains carrying this factor for eukaryotic gene cloning is complicated, thereby reducing still further the applicability of the scheme which utilizes the inducible expression plasmids. Finally, since there are usually 2 or 3 copies of the F-prime plasmid in a cell (each of which maintains about 100-150 lactose repressor molecules), and since each cell also contains 10-20 copies of one of the inducible expression plasmids (each carrying a functional lac promoter), the ratio of repressor molecules to lac promoters will vary widely from cell to cell, and in some instances will not achieve complete repression of the desired expression product. Accordingly, while inducible (but not auto-regulated) expression plasmids are considered to be part of the present invention, the auto-regulated inducible cloning vehicles described herein are preferred for polypeptide expression in microbial hosts.

4. Experimental

The strategy and techniques described hereinabove were applied experimentally to construct a recombinant bacterial plasmid cloning vehicle according to the present invention. For completeness and continuity, the specific experimental steps used to construct the lpp gene expression plasmids resulting from the previous research of one of the present inventors are repeated herein in full, followed by the experimental steps used to construct one of the plasmids of the present invention, and then followed by a description of the preferred method of constructing all of the plasmids of the present invention. In the prior research, three types or "families" of vehicles were contemplated, one for constitutive gene expression (labelled the "pIN-I" type), a second for inducible gene expression (the "pIN-II" type), and a third for auto-regulated inducible gene expression (the "pIN-III" type). The pIN-II and pIN-III types both utilize the 95 bp lac promoter-operator fragment discussed hereinabove. For clarity, the new inducible and auto-regulated inducible expression plasmids of the present invention which utilize the 113 bp lac fragment are hereinafter referred to collectively as the "pIN-II(113)" and "pIN-III(113)" types or series, respectively.

Figure 5:
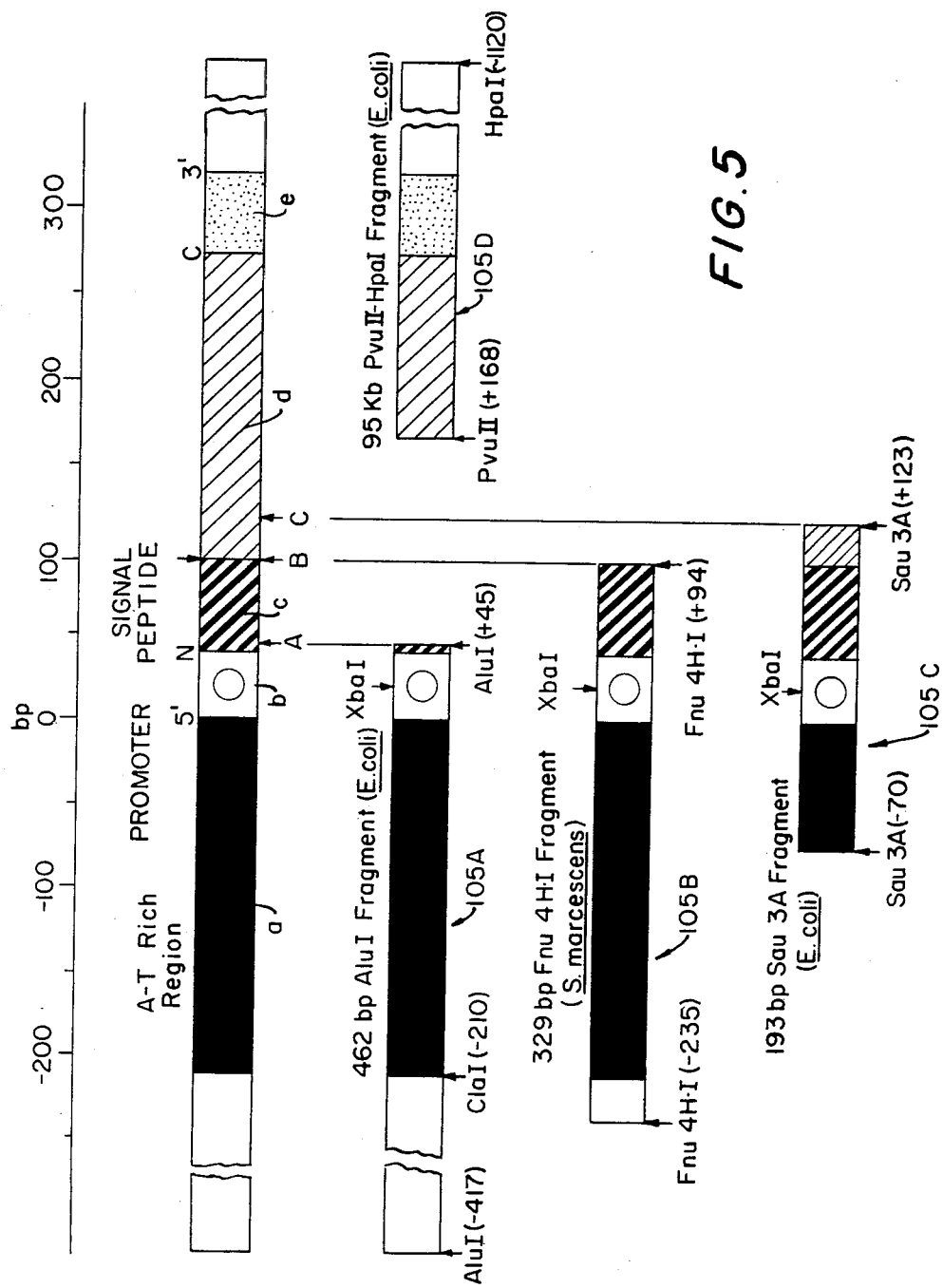
FIGS. 5–29 together comprise a schematic illustration of the preferred method for construction of the constitutive, inducible, and auto-regulated inducible, recombinant plasmid cloning vehicles resulting from the earlier research efforts of one of the present inventors, in which the relative positions of various restriction endonuclease cleavage sites are shown, and in which Amp$^r$ and Tc$^r$, respectively, denote genes for ampicillin and tetracycline resistance.

In the remainder of this application, the insertion site located within the DNA sequence coding for the prolipoprotein signal peptide will be designated the "A" site, while the insertion site located immediately after the last codon of the signal peptide will be labelled the "B" site, and the insertion site located after the codon for the eighth amino acid residue of the mature lipoprotein will be referred to as the "C" site (see FIG. 5). For each site, three plasmids can be prepared (one corresponding to each of the three possible reading frames), yielding a total of nine expression plasmids in each series which are labelled A-1, A-2, A-3, B-1, B-2, B-3, and C-1, C-2, C-3.

The restriction enzymes used herein were obtained from New England Biolabs and Bethesda Research Laboratories. T4 DNA ligase was obtained from Bethesda Research Laboratories (unless otherwise indicated), and S1 Nuclease was obtained from Miles Laboratories.

A. Construction of A Site Plasmids (pIN-I)

FIGS. 6-15 schematically depict the manner in which constitutive recombinant plasmids incorporating the A insertion site were constructed, and may be referred to in connection with the following more particularized discussion.

1. Construction of Plasmid pKEN111

The first step in the construction of the A site lpp gene cloning vehicles was to construct a plasmid to serve as a source of lpp gene components in subsequent steps of the procedure. The plasmid chosen to receive the *E. coli* lpp gene for this purpose was pSC101, a small (molecular wt. approximately 5.8 megadaltons) plasmid carrying a gene conferring resistance to the antibiotic tetracycline (Tc) (Cohen, S. N., et al., *J. Bacteriol.* 132: 737-737 [1977]). As shown at 100 in FIG. 6, pSC101 includes a cleavage site for the restriction endonuclease Eco RI located at the 5' end of the tetracycline resistance gene. The plasmid pSC101 was obtained from Dr. E. Ohtsubo at the Department of Microbiology, State University of New York at Stony Brook.

As shown schematically at 101 in FIG. 6, 2 micrograms of plasmid pSC101 DNA were digested to completion with two units of the restriction endonuclease Eco RI in 50 microliters of a reaction mixture comprising 100 mM Tris:HCl (pH 7.5), 75 mM NaCl, 6 mM MgCl$_2$, 6 mM β-mercaptoethanol and 100 micrograms/ml bovine serum albumin (hereinafter "BSA") (this reaction mixture will hereinafter be referred to as an "Eco RI buffer") at 37° C. for 60 minutes. To prevent self-ligation of the Eco RI-treated pSC101 DNA, bacterial alkaline phosphatase (hereinafter "BAP") was added (0.1 units of Worthington BAPF), and incubation was continued for 60 minutes at 37° C. The reaction was terminated by phenol extraction, and the linearized DNAs were recovered by ethanol precipitation.

Figure 6:
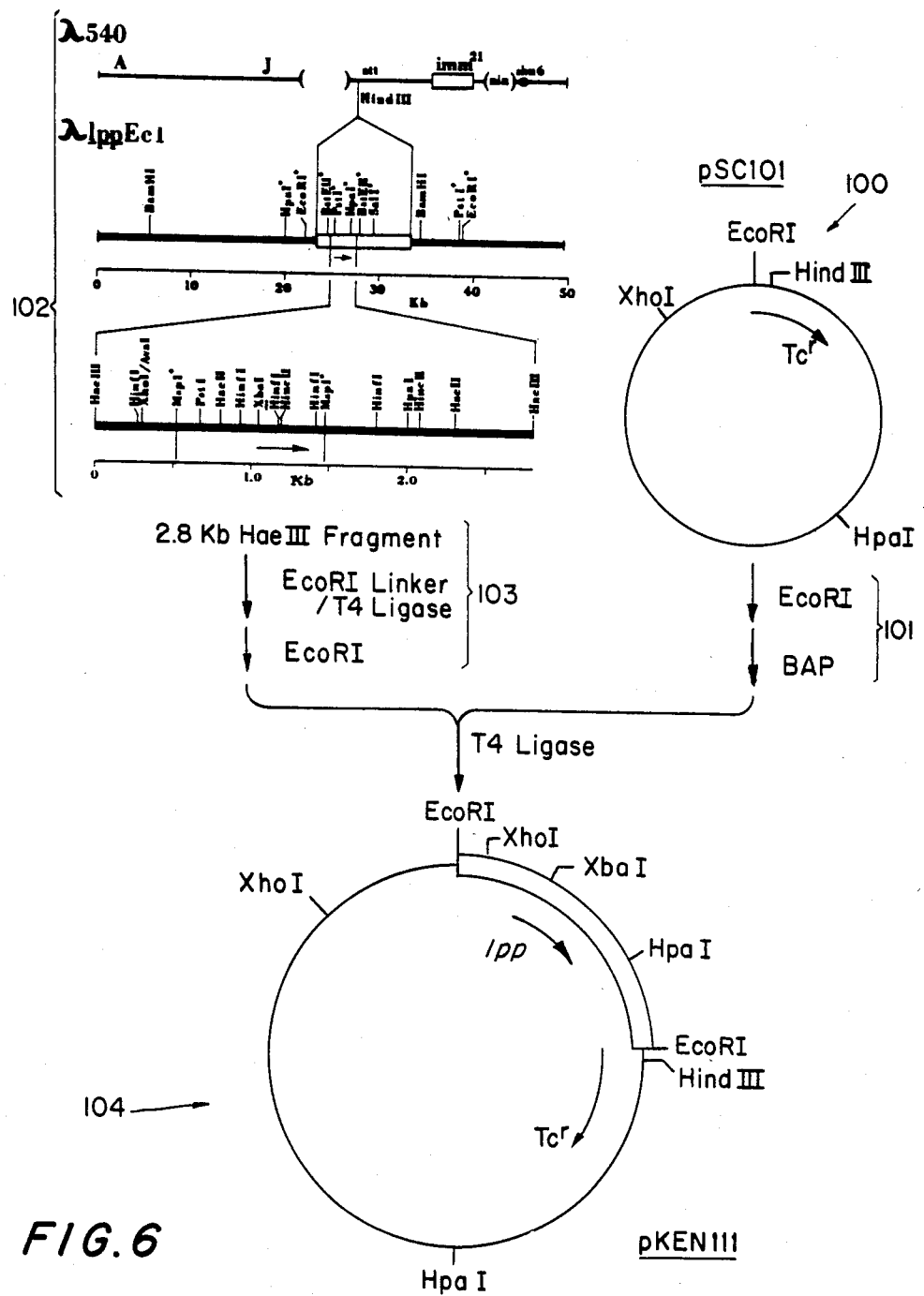

A 2.8 kilobase ("Kb") DNA fragment containing the *E. coli* lpp gene was separately derived, as shown at 102 in FIG. 6, from a hybrid λ phage carrying the *E. coli* lpp gene (designated λlppEc-1). The lpp gene had previously been cloned into a λ phage vector, λ540 (Murray and Murray, *J. Mol. Biol.* 98: 551-564 [1975]), as follows: Total DNA (200 micrograms) isolated from an *E. coli* K-12 strain merodiploid for the lpp gene (JE5519/F506 [Movva, N. R., et al., *J. Bacteriol.* 133: 81-84 (1978)]) was digested with 200 units of the restriction enzyme Hind III. DNA fragments were separated on a preparative agarose gel, and fractions of DNA fragments of approximately 10 Kb which showed positive hybridization with 5'-$^{32}$P-lipoprotein mRNA were collected, using the Southern hybridization technique (*J. Mol. Biol.* 98: 503-517). A mixture of 10 Kb Hind III fragments (enriched approximately twenty-fold) and Hind III-cleaved λ540 vector DNA was reacted with T4 DNA ligase. Ligated DNA was used to transfect *E. coli* K802, NRRL B-15016 (obtained from Dr. F. R. Blattner at the Laboratory of Genetics, University of Wisconsin-Madison). This strain is available to the public from the permanent collection of the Northern Regional Research Laboratory, U.S. Department of Agriculture, Peoria, Ill., U.S.A. Recombinant phages carrying the lpp gene were screened by the plaque hybridization technique of Benton and Davis (*Science* 196: 180-182 [1977]) using 5'-=P-lipoprotein mRNA. One of the plaques examined which gave positive hybridization was found to carry a fully functional lpp gene, and was designated λlppEc-1.

Two hundred micrograms of λlppEc-1 DNA were then digested completely with 200 units of the restriction enzyme Hae III in 500 microliters of a reaction mixture containing 6 mM Tris:HCl (pH 7.5), 6 mM MgCl$_2$, 6 mM NaCl, 6 mM β-mercaptoethanol and 100 micrograms/ml BSA (the foregoing reaction mixture will hereinafter be referred to as a "Hae III buffer") at 37° C. for 2 hours, and the 2.8 Kb Hae III fragment carrying the *E. coli* lpp gene was purified by fractionation on a 5% polyacrylamide gel according to the following procedure: The reaction mixture was first extracted with phenol, and the DNA fragments were then precipitated with 2.5 volumes of ethanol, dried under vacuum, dissolved in 200 microliters of a buffer comprising 5% glycerol, 20 mM EDTA, 0.05% bromophenol blue and 0.05% xylen cyanol (this mixture will hereinafter be referred to as a "gel buffer") and thereafter fractionated on a 5% polyacrylamide gel. The DNA band which had migrated to a 2.8 Kb position was excised from the gel, and the DNA fragments were eluted from the gel by electrophoresis. Ethidium bromide dye, used to locate the DNA band in the gel, was removed from the DNA fragments by phenol extraction. The DNA fragments were precipitated with 2.5 volumes of ethanol, centrifuged, dissolved in 200 microliters of 0.3M Na-acetate, re-precipitated with 0.5 ml of ethanol and dried again under vacuum. Approximately 10 micrograms of a purified 2.8 Kb Hae III fragment were recovered.

In order to clone the 2.8 Kb Hae III fragment into pSC101, synthetic "Eco RI linker" molecules were attached to the termini of the 2.8 Kb Hae III fragment, as shown schematically at 103 in FIG. 6. The Eco RI linker (5'GGAATTCC3'; obtained from Collaborative Research) was phosphorylated by T4 polynucleotide kinase (obtained from P.L. Biochemicals) with ATP in 50 microliters of a reaction mixture containing 3 moles of the linker, 66 mM Tris:HCl (pH 7.5), 10 mM MgCl$_2$, 10 mM β-mercaptoethanol, 60 μM ATP and 10 units of T4 polynucleotide kinase. After the mixture was incubated at 37° C. for 30 minutes, it was heated at 60° C. for 10 minutes, and cooled to 37° C. Five microliters of 0.1M β-mercaptoethanol and 10 units of T4 polynucleotide kinase were added to the mixture, and the reaction was continued at 37° C. for 30 minutes. The reaction was terminated by freezing the mixture in a dry ice-ethanol bath.

The 2.8 Kb Hae III fragment (2 micrograms) was mixed with 150 pmoles of phosphorylated Eco RI linker and was treated with 4 units of T4 DNA ligase in 12.5 microliters of a reaction mixture containing 66 mM Tris:HCl (pH 7.5), 10 mM MgCl$_2$, 10 mM dithiothreitol (the foregoing reaction mixture will hereinafter be referred to as a "ligase buffer") and 0.6 mM ATP at 12.5° C. for 15 hours. The reaction was terminated by diluting the mixture twenty-fold with Eco RI buffer and by heating the mixture at 60° C. for 10 minutes. Thirty units of the restriction enzyme Eco RI were added, and the mixture was incubated at 37° C. for one hour to create Eco RI cohesive termini. The reaction was terminated by heating at 60° C. for 10 minutes.

The mixture thus obtained was added to 2 micrograms of the previously-linearized plasmid pSC101 DNA, and phenol extraction was performed. After extraction with ether, the DNAs were precipitated with ethanol, dried under vacuum, and dissolved in 100 microliters of ligase buffer. The mixture was heated at 37° C. for 5 minutes, and the Eco RI cohesive termini were annealed by incubating at 4° C. for 16 hours and then at 0° C. for one hour. After adding ATP (0.4 mM final) and 1 unit of T4 DNA ligase, the mixture was incubated at 12.5° C. for 7 hours.

One-fourth of the ligation mixture was thereafter used to transform *E. coli* lpp deletion mutant strain JE5527, NRRL B-15012 (F-, man, lpp-2, pps, thi, his, rpsL, gyrA, recAl [Hirota, Y., et al., *Proc. Natl. Acad. Sci. U.S.A.* 74: 1417–1420 (1977)], obtained from Dr. Y. Hirota, National Institute of Genetics, Mishima, Japan). This strain is available to the public from the permanent collection of the Northern Regional Research Laboratory, U.S. Department of Agriculture, Peoria, Ill., U.S.A. Transformation was carried out as described in Cohen, S. N., et al., *Proc. Natl. Acad. Sci. U.S.A.* 69: 2110–2114 (1972), and tetracycline-resistant transformants were grown overnight on Whatman 3 MM filter papers, placed on the surface of an L broth plate containing 10 micrograms/ml of tetracycline, and screened for lpp clones by colony hybridization (Gergen, J. P., et al., *Nucleic Acids Res.* 7: 2115–2136 [1979]). A 0.95 Kb Msp I fragment of λlppEc-1 containing the lpp gene was nick-translated with [α-$^{32}$P]dATP and [α-$^{32}$P]dCTP, as described i Maniatis, T., et al., *Proc. Natl. Acad. Sci. U.S.A.* 72: 1184–1188 (1975 ), and was used as a $^{32}$P-probe. One of the transformants which gave positive hybridization was shown to contain the plasmid with the structure illustrated at 104 in FIG. 6, and this plasmid was designated pKEN1l1. This plasmid is obtainable from *E. coli* CC620/pKEN1l1, NRRL B-15011, which is available to the public from the permanent collection of the Northern Regional Research Laboratory, U.S. Department of Agriculture, Peoria, Ill., U.S.A. The plasmid can be obtained from NRRL B-15011 by conventional means.

2. Construction of Plasmid pKEN008

Figure 7:
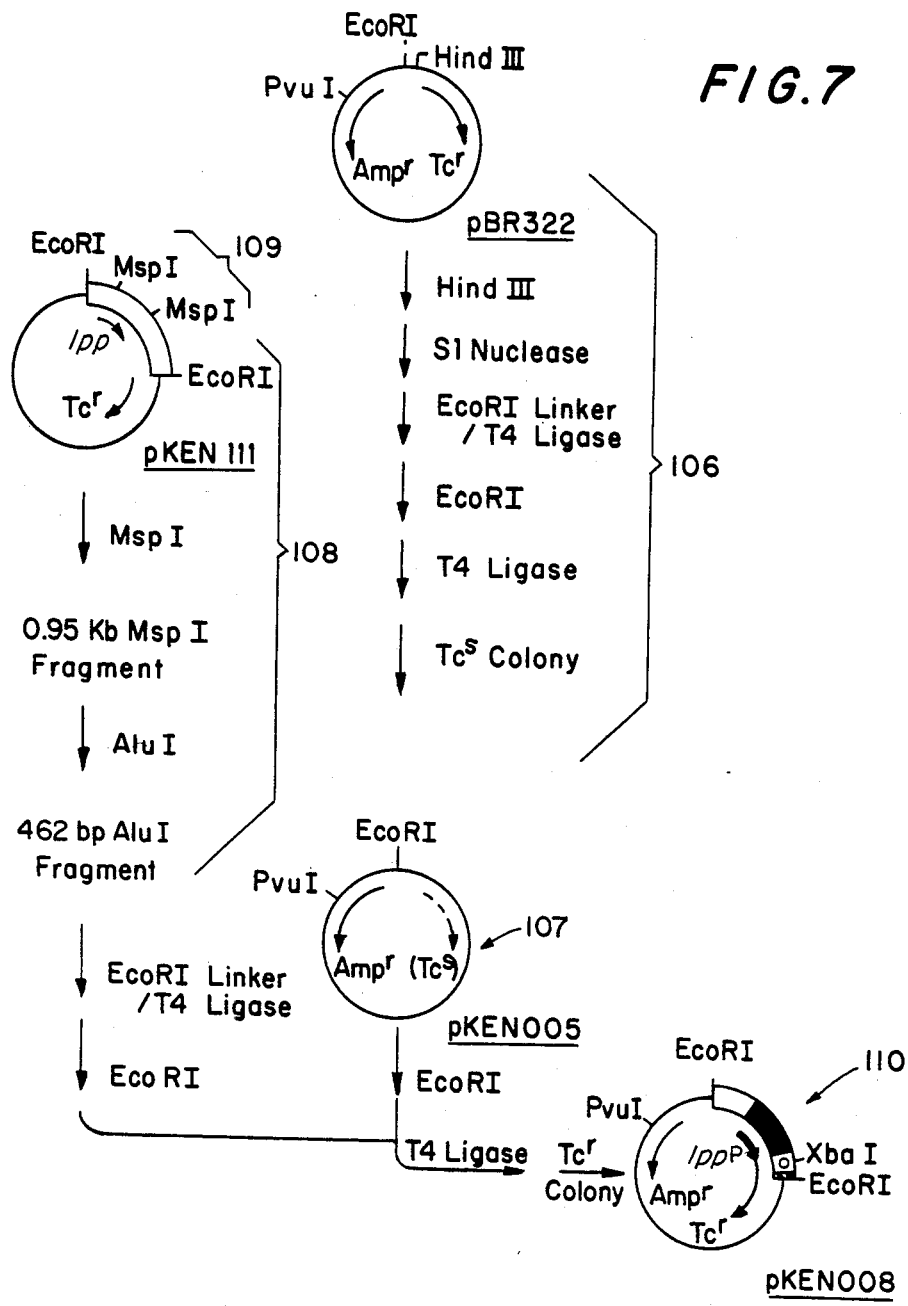

The parental plasmid chosen for construction of the lpp gene expression plasmids of the present invention was pBR322 (molecular wt. approximately 2.6 megadaltons), carrying genes conferring resistance to the antibiotics ampicillin (Amp) and tetracycline (Tc) (Bolivar, F., et al., *Gene* 2: 95–113 [1977]). As shown in FIG. 7, pBR322 includes an Eco RI cleavage site located at the 5' end of the tetracycline resistance gene, as well as a Hind III cleavage site located within the promoter of the tetracycline resistance gene and a Pvu I cleavage site located within the ampicillin resistance gene. The plasmid pBR322 was obtained from Dr. N. Arnheim of the Department of Biochemistry, State University of New York at Stony Brook, and is available commercially from Bethesda Research Laboratories.

FIG. 5 illustrates schematically the various components of the lpp gene, each of which is identified by a symbol or shading. Specifically, the shaded segment indicated by the letter "a" identifies the A-T rich region of approximately 260 base pairs preceding the transcription initiation site and containing the lpp promoter. The 5'-untranslated region is identified by the segment containing the circular device and marked with the letter "b". The signal peptide region of the prolipoprotein is identified by the diagonally hatched and shaded segment "c". The structural region of the lpp gene is identified by the diagonally hatched segment labelled with the letter "d", while the speckled segment "e" identifies the 3'-untranslated region and the transcription termination site. These symbols and shading are used in a like manner to identify the same functional fragments of the lpp gene in FIGS. 7–11, 15, 17–18, 21–23, and 26–31B.

FIG. 7 illustrates the strategy used for inserting a fragment carrying the promoter and the 5'-untranslated region of the lpp gene into pBR322. The fragment chosen for this purpose was a 462 bp Alu I fragment of pKEN111 which, as shown schematically at 105A in FIG. 5, contains not only the promoter sequence and the 5'-untranslated region (positions -45 to -1 and +1 to +39, respectively) of the lpp gene, but also the entire extremely A-T rich segment preceding the promoter sequence.

In order to clone the 462 bp Alu I fragment containing the lpp promoter region in pBR322, the DNA fragment lying between the Eco RI and Hind III cleavage sites of pBR322 (containing the promoter of the tetracycline resistance gene) was first deleted, as shown schematically at 106 in FIG. 7, using the following procedure: 11 micrograms of pBR322 plasmid DNA were digested with 11 units of Hind III restriction endonuclease in 200 microliters of a reaction mixture comprising 10 mM Tris:HCl (pH 7.5), 10 mM MgCl$_2$, 60 mM NaCl, 6 mM β-mercaptoethanol and 100 micrograms/ml BSA (this reaction mixture will hereinafter be referred to as a "Hind III buffer") at 37° C. for one hour. After digestion was completed, phenol extraction was performed, and DNAs were recovered by ethanol precipitation.

To remove the Hind III cohesive termini, the DNA was treated with 1.5 microliters of S1 Nuclease (Miles Laboratories) in a final volume of 300 microliters of a buffer containing 30 mM Na-acetate (pH 4.25), 0.3M NaCl and 4 mM ZnSO$_4$ (hereinafter referred to as an "S1 buffer") at 20° C. for one hour. The reaction was terminated by adding 30 microliters 500 mM Tris:HCl (pH 8.0) and 30 microliters 250 mM EDTA, following which phenol extraction was performed. To remove phenol, the mixture was extracted with ether and dialyzed against 0.01×SSC (SSC=0.15M NaCl+0.015M Na-citrate) at 4° C. overnight, and the DNAs were recovered by ethanol precipitation.

Phosphorylated Eco RI linker (200 pmoles) was then added and the mixture was treated with 4 units of T4 DNA ligase in 12.5 microliters of ligase buffer containing 0.6 mM ATP at 12.5° C. for 16 hours. Eco RI cohesive termini were created by addition of 30 units of Eco RI restriction enzyme in 75 microliters of Eco RI buffer at 37° C. for 2 hours. The reaction was terminated by phenol extraction and the DNAs were recovered by ethanol precipitation.

Eco RI cohesive termini were ligated and the plasmid was thereby re-circularized by treatment with 0.3 units of T4 DNA ligase in 20 microliters of ligase buffer containing 0.4 mM ATP at 12.5° C. for 7 hours. A 0.5 microgram aliquot of the ligated DNA was used to transform *E. coli* strain JE5519, NRRL B-15013 (F-, aroD, man, argE, lac, gal, rpsL, gyrA, recAl; obtained from Dr. Y. Hirota, National Institute of Genetics, Mishima, Japan). This strain is available to the public from the permanent collection of the Northern Regional Research Laboratory, U.S. Department of Agriculture, Peoria, Ill. U.S.A. Ten of the ampicillin-resistant, tetracycline-sensitive transformants were grown overnight in one ml of L broth containing 50 micrograms/ml of ampicillin. Plasmid DNAs were isolated from 0.5 ml of the cultures by the rapid alkaline-denaturation method described by Birnboim, H. C. and Doly, J., *Nucleic Acids Res.* 7: 1513 (1979), and analyzed by restriction enzyme mapping. One of the plasmids had the structure shown at 107 in FIG. 7, and was designated pKEN005.

As shown schematically at 108 in FIG. 7, the 462 bp Alu I fragment containing the lpp promoter was derived as follows: 100 micrograms of pKEN111 plasmid DNA were digested with Msp I restriction enzyme in 600 microliters of a buffer containing 10 mM Tris:HCl (pH 7.5), 10 mM MgCl$_2$, 6 mM KCl, 1 mM dithiothreitol, and 100 micrograms/ml BSA (this mixture will hereinafter be referred to as an "Hpa I buffer") at 37° C. for 3 hours. (Although pKEN111 contains numerous Msp I cleavage sites, only the two of interest are illustrated at 109 in FIG. 7.) Following extraction with phenol, the DNA fragments were precipitated with 2.5 volumes of ethanol, dried under vacuum, dissolved in 100 microliters of gel buffer, and fractionated on a 5% polyacrylamide gel. Approximately 6 micrograms of a purified 0.95 Kb Msp I fragment were recovered after elution of the separated DNA fragments from the gel. The purified 0.95 Kb Msp I fragment was subsequently digested with Alu I restriction endonuclease in 400 microliters of Hind III buffer at 37° C. for 2 hours, yielding a 462 bp Alu I fragment which was purified by gel electrophoresis.

One microgram of the 462 bp Alu I fragment was then mixed with 150 pmoles of phosphorylated Eco RI linker and treated with 4 units of T4 DNA ligase in 10 microliters of ligase buffer containing 0.6 mM ATP at 12.5° C. for 16 hours. The ligated DNA was digested with 40 units of Eco RI restriction enzyme in 100 microliters of Eco RI buffer at 37° C. for one hour to create Eco RI cohesive termini. The digestion was terminated by heating the mixture at 60° C. for 10 minutes, and 0.6 micrograms of Eco RI-digested pKEN005 plasmid DNA were added to the mixture and phenol extraction was performed. The DNAs were recovered by ethanol precipitation, and the Eco RI cohesive termini were joined by treating with 0.4 units of T4 DNA ligase in 20 microliters of ligase buffer containing 0.4 mM ATP at 12.5° C. for 7 hours. Ligated DNAs were used to transform *E. coli* strain JE5519, NRRL B-15013, and transformants were selected for tetracycline resistance on an L broth plate containing 12.5 micrograms/ml of tetracycline. Analysis of the plasmid DNAs isolated from the tetracycline-resistant transformants by the rapid alkaline-denaturation method showed insertion of the 462 bp Alu I fragment at the Eco RI site of pKEN005 as depicted at 110 in FIG. 7, and one of the plasmids thus obtained was designated pKEN008.

3. Construction of Plasmid pKEN010

Figure 8:
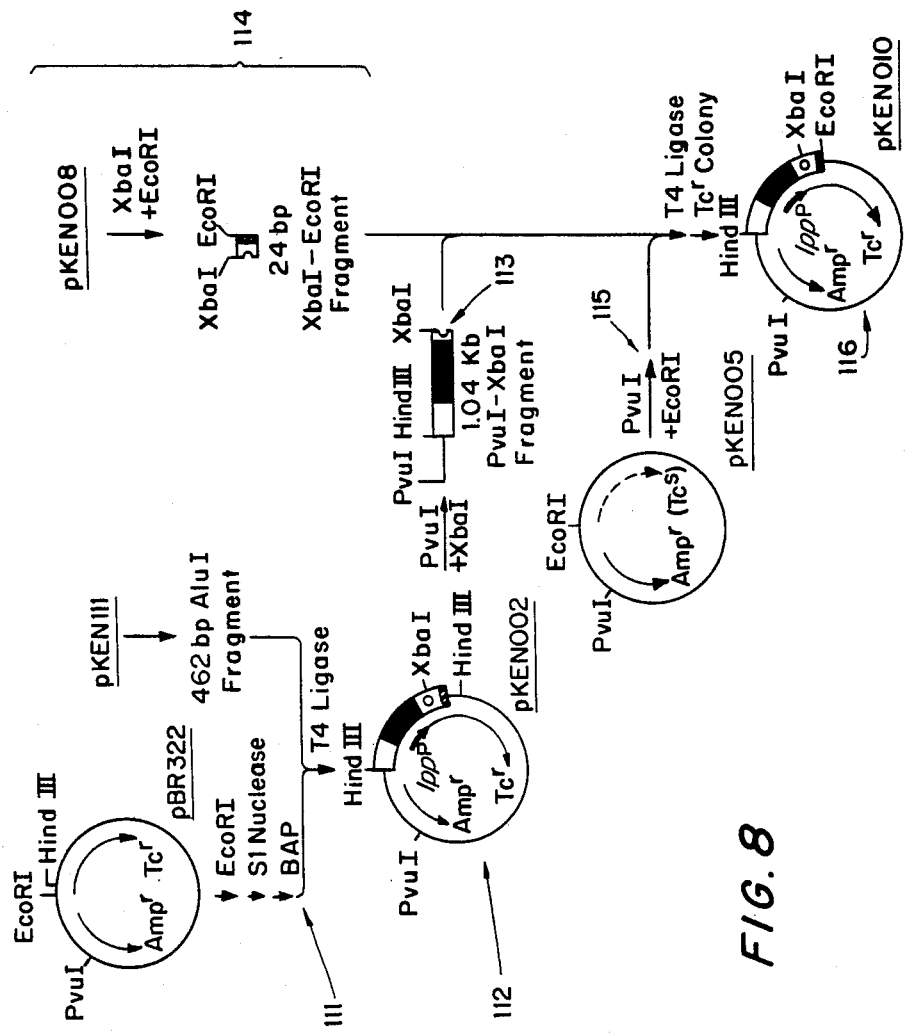

The next step in the construction of the A site lpp gene cloning vehicles was to eliminate one of the two Eco RI cleavage sites of pKEN008. This was necessry in order to insure that the only insertion point available for the exogenous gene chosen for cloning would be immediately downstream of the 462 bp Alu I fragment (now an Eco RI fragment) containing the lpp gene promoter and 5'-untranslated region. FIG. 8 illustrates schematically the strategy for removing the Eco RI site distal to the lpp gene promoter.

In order to accomplish this result, the following procedure was used: 4 micrograms of Eco RI-digested pBR322 plasmid DNA were treated first with S1 Nuclease to remove the Eco RI cohesive termini, and then with BAP to prevent self-ligation. As shown schematically at 111 in FIG. 8, the DNAs were then mixed with 0.76 micrograms of the purified 462 bp ALu I fragment (derived from pKEN111 as described above in connection with FIG. 7), and blunt-end ligated with 2.4 units of T4 DNA ligase in 10 microliters of ligase buffer containing 0.6 mM ATP at 12.5° C. for 16 hours. One-half of the ligated DNA was used to transform *E. coli* strain JE5519, NRRL B-15013, and one of the transformants was shown to contain the plasmid with the structure illustrated at 112 in FIG. 8. This plasmid was designated pKEN002, and after digestion of 25 micrograms of pKEN002 plasmid DNA with Pvu I and Xba I restriction enzymes in 500 microliters of a buffer comprising 6 mM Tris:HCl (pH 7.9), 6 mM MgC12, 150 mM NaCl, 6 mM β-mercaptoethanol and 100 micrograms/ml BSA (the foregoing mixture will hereinafter be referred to as a "Bam HI buffer") at 37° C. for one hour, a 1.04 Kb Pvu I-Xba I DNA fragment (illustrated at 113 in FIG. 8) was purified by gel electrophoresis.

As shown schematically at 114 in FIG. 8, a 24 bp Xba I-Eco RI DNA fragment was derived from pKEN008 as follows: 25 micrograms of pKEN008 plasmid DNA was digested with Eco RI restriction enzyme, and a 470 bp Eco RI fragment was purified by gel electrophoresis. One microgram of the 470 bp Eco RI fragment was then digested with Xba I restriction enzyme, and was mixed with one microgram of the 1.04 Kb Pvu I-Xba I DNA fragment obtained previously, as well as with 0.75 micrograms of pKEN005 plasmid DNA previously digested with Pvu I and Eco RI restriction enzymes (as shown at 115 in FIG. 8). The DNA mixture was treated with 0.8 units of T4 DNA ligase in 50 microliters of ligase buffer containing 0.4 mM ATP at 12.5° C. for 7 hours. One-half of the ligated DNA was used to transform *E. coli* strain JE5519, NRRL B-15013, and transformants were selected for tetracycline resistance. Analysis of the plasmid DNAs obtained from 0.5 ml cultures of tetracycline-resistant transformants by the rapid alkaline-denaturation method, indicated that one of the plasmids had the structure shown at 116 in FIG. 8. This plasmid was designated pKEN010.

4. Construction of Plasmid pKEN018

Figure 9:
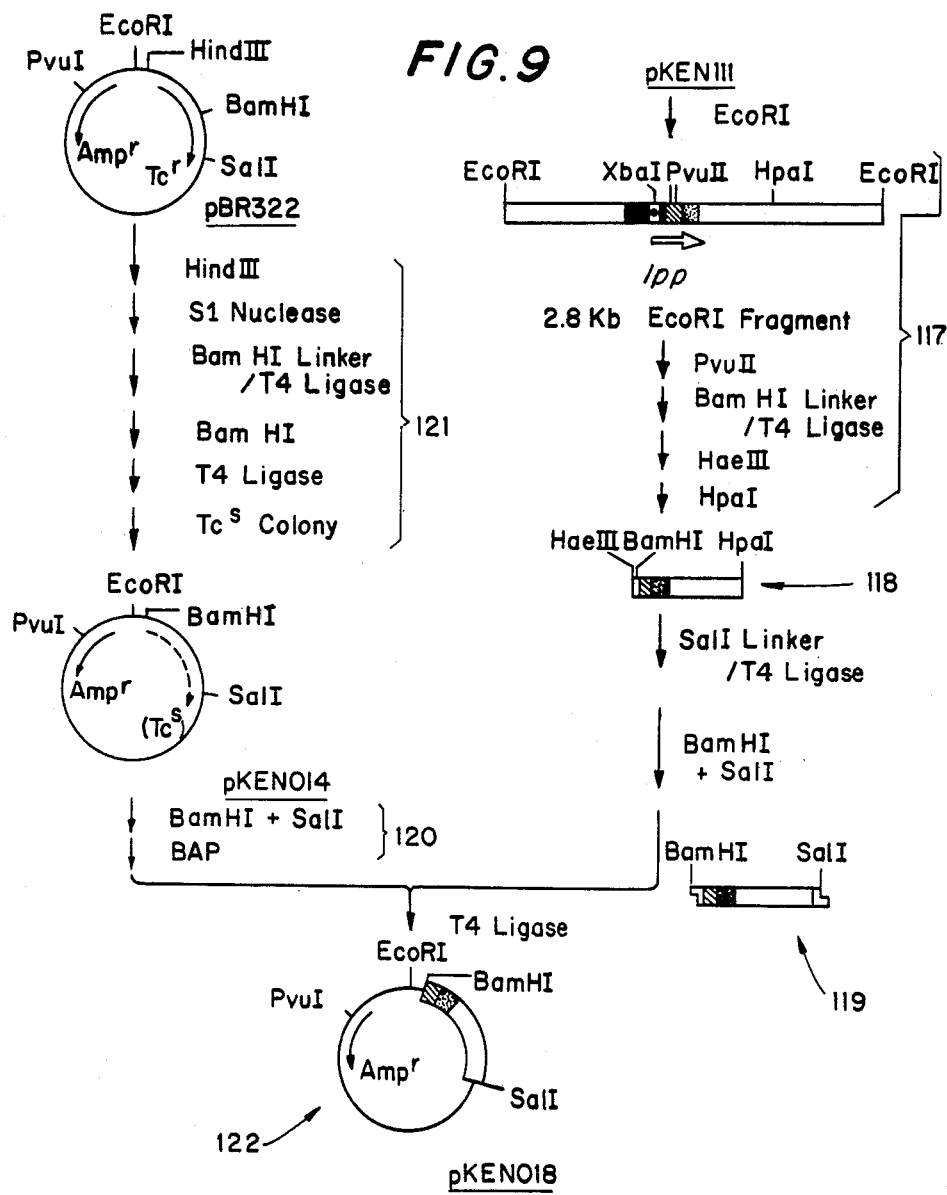

FIG. 9 illustrates the strategy used for cloning a DNA fragment carrying the 3'-untranslated region and the transcription termination site of the lpp gene. The fragment chosen for this purpose was a 0.95 Kb Pvu II-Hpa I fragment of pKEN111, shown schematically at 105D in FIG. 5. Since the Pvu II restriction enzyme cleaves the lpp gene sequence between positions +167 and +168, this fragment contains approximately the latter half of the lpp gene (see FIGS. 1 and 5). In order to insert this fragment into the cloning vehicle in the same orientation as the promoter fragment, Bam HI linker and Sal I linker were attached to the Pvu II and Hpa I cleavage sites, respectively.

As shown schematically at 117 in FIG. 9, a 2.8 Kb Eco RI fragment was obtained from pKEN111 plasmid DNA by digestion with Eco RI restriction enzyme and fractionation on a polyacrylamide gel, and 10 micrograms of this purified fragment were digested completely with Pvu II restriction endonuclease in 500 microliters of Hae III buffer at 37° C. for one hour. The reaction was terminated by phenol extraction, and the mixture was extracted with ether. The DNA fragments were precipitated with 2.5 volumes of ethanol, centrifuged, re-dissolved in 200 microliters of 0.3M Na-acetate and re-precipitated with 0.5 ml of ethanol. Five micrograms of the Pvu II-digested 2.8 Kb Eco RI fragment were mixed with 390 pmoles of phosphorylated Bam HI linker and blunt-end ligated with 6 units of T4 DNA ligase in 25 microliters of ligase buffer containing 0.6 mM ATP at 12.5° C. for 16 hours. The reaction mixture was diluted to 150 microliters with Hae III buffer and heated at 60° C. for 10 minutes to inactivate the T4 DNA ligase. After the addition of 60 units of Hae III restriction enzyme, the mixture was incubated at 37° C. for one hour.

Since the Bam HI linker used here (obtained from Collaborative Research and phosphorylated in the same manner as described previously in connection with the Eco RI linker) has the base sequence 5'CCGGATCCGG3', the recognition sequence for the restriction enzyme Hae III

was created at the junction of any two linker fragments. Thus, the use of Hae III restriction enzyme as set forth above to digest the Bam HI linker-ligated Pvu II fragments (which fragments do not contain any internal Hae III cleavage sites) effected the removal of superfluous multiple Bam HI linker fragments joined to the Pvu II terminus, leaving only one such linker fragment directly joined to that terminus. This procedure greatly simplified the purification of the DNA fragment containing the 3' end of the lpp gene, as described below.

After inactivation of the Hae III enzyme by heating the reaction mixture at 60° C. for 10 minutes, the DNA fragments were digested completely with Hpa I restriction enzyme in 400 microliters of Hpa I buffer at 37° C. for 2 hours. The reaction mixture was extracted with phenol and the DNA fragments were precipitated with ethanol, dried under vacuum, dissolved in 100 microliters of gel buffer and fractionated on a 5% polyacrylamide gel. The DNA band which had migrated to a 0.95 Kb position was excised from the gel, and the DNA fragments were eluted from the gel by electrophoresis. After removal of ethidium bromide dye by phenol extraction, the DNA fragments were precipitated with 2.5 volumes of ethanol, centrifuged, dissolved in 200 microliters of 0.3M Na-acetate, re-precipitaed with 0.5 ml of ethanol and again dried under vacuum. Approximately one microgram of a purified 0.95 Kb Hae III-Hpa I fragment (illustrated at 118 in FIG. 9) was recovered.

One hundred and twenty pmoles of phosphorylated Sal I linker (5'GGTCGACC3'; obtained from Collaborative Research and phosphorylated according to the same procedure as described hereinabove) were mixed with 0.75 micrograms of the purified 0.95 Kb Hae III-Hpa I fragment, and blunt-end ligated with 3.5 units of T4 DNA ligase in 25 microliters of ligase buffer containing 0.6 mM ATP at 12.5° C. for 16 hours. The reaction mixture was diluted with sufficient Bam HI buffer to make a final volume of 300 microliters and was then heated at 60° C. for 10 minutes. Sufficient amounts of Bam HI and Sal I restriction enzymes were added and the mixture was incubated at 37° C. for 2 hours to create cohesive termini by cleaving the Bam HI and Sal I linkers attached to the Pvu II and Hpa I termini, respectively, resulting in a 0.95 Kb Bam HI-Sal I fragment (illustrated at 119 in FIG. 9). The restriction endonuclease digestion was terminated by heating at 60° C. for 10 minutes.

At this stage, half the volume of the mixture (150 microliters), containing approximately 0.38 micrograms of the 0.95 Kb Bam HI-Sal I fragment, was mixed with one microgram of pKEN014 plasmid DNA, which had previously been digested with Bam HI and Sal I restriction enzymes and treated with BAP (as shown schematically at 120 in FIG. 9). Plasmid pKEN014 had been previously derived from pBR322 by deleting a 346 bp Hind III-Bam HI fragment (containing most of the tetracycline resistance gene) from pBR322. This fragment was removed in order to keep the size of the expression plasmids to a minimum (approximately 5 Kb). The deletion of this fragment was accomplished, as shown schematically at 121 in FIG. 9, by Hind III digestion, followed by S1 Nuclease treatment for one hour at 20° C., Bam HI linker attachment, Bam HI complete digestion, re-circularization by T4 DNA ligase, and selection of tetracycline-sensitive transformants.

The mixture of linearized pKEN014 plasmid DNA and 0.95 Kb Bam HI-Sal I fragments was extracted with phenol, and the DNAs were precipitated with 2.5 volumes of ethanol, centrifuged and dissolved in 200 microliters of 0.3M Na-acetate. The DNAs were re-precipitated with 0.5 ml of ethanol, centrifuged and dried under vacuum. Cohesive termini of the DNA fragments were annealed with 0.4 units of T4 DNA ligase in 60 microliters of ligase buffer containing 0.4 mM ATP at 12.5° C. for 7 hours. Twelve microliters of the ligated mixture were then used to transform E. coli strain JE5519, NRRL B-15013, and twelve of the ampicillin-resistant transformants were grown overnight in one ml of L broth containing 50 micrograms/ml of ampicillin. Plasmid DNAs were isolated from 0.5 ml of the cultures by the rapid alkaline-denaturation method and analyzed by agarose gel electrophoresis. Five of the plasmid DNAs were found to carry the 0.95 Kb Bam HI-Sal I fragment, and one of these plasmids were designated pKEN018. DNA sequencing of the pKEN018 plasmid DNA indicated the structure shown at 122 in FIG. 9, and specifically showed that the Bam HI linker was attached at the Pvu II site within the lpp gene at the correct position.

5. Construction of Plasmid pKEN021

The next step in the construction of the A site lpp gene cloning vehicles was to combine the lpp promoter fragment with the transcription terminator fragment in the same orientation. This step was carried out by replacing a 630 bp Pvu I-Eco RI fragment of pKEN018 with a 1.1 Kb Pvu I-Eco RI fragment of pKEN010, as illustrated schematically in FIG. 10.

In order to accomplish this result, 20 micrograms of pKEN010 plasmid DNA were digested to completion (as shown at 213 in FIG. 10) with Pvu I restriction endonuclease in 100 microliters of Bam HI buffer at 37° C. for 1.5 hours. After inactivating the Pvu I enzyme by heating the reaction mixture at 60° C. for 10 minutes, 52 microliters of water, 40 microliters of 0.5M Tris:HCl (pH 7.5), 4 microliters of 0.1M MgCl$_2$ and 40 units of Eco RI restriction enzyme were added. The reaction mixture was incubated at 37° C. for one hour and the digestion was terminated by phenol extraction. The DNA fragments were precipitated with 2.5 volumes of ethanol, dried under vacuum, dissolved in 100 microliters of gel buffer, and fractionated on a 5% polyacrylamide gel. Four micrograms of a purified 1.1 Kb Pvu I-Eco RI fragment were obtained after elution of the separated DNA fragments from the gel.

Figure 10:
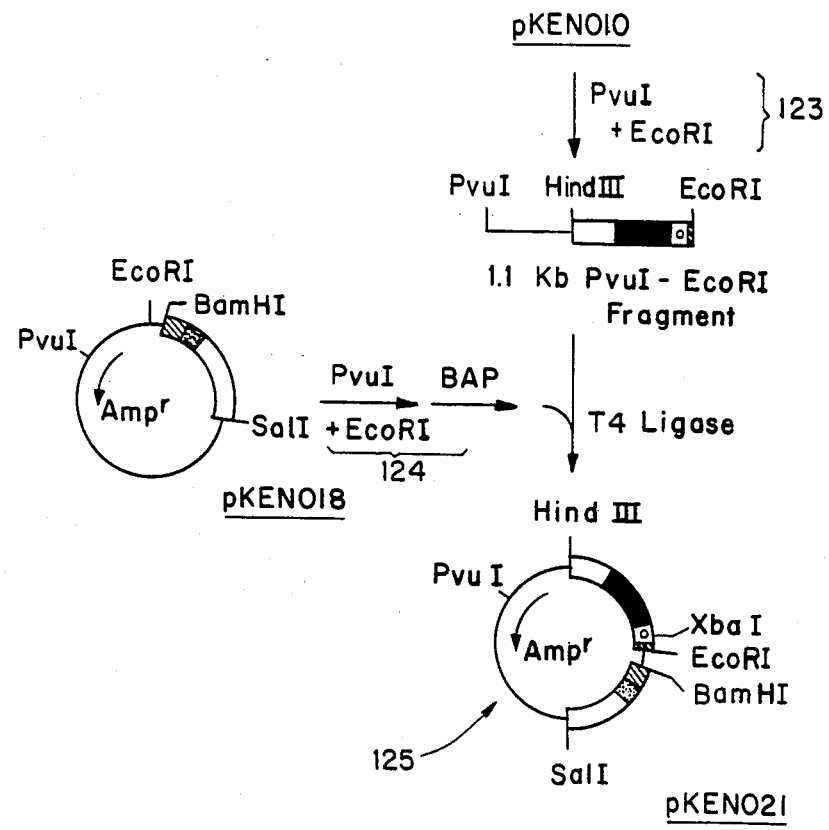

The purified fragment (0.75 micrograms) was then mixed with 0.6 micrograms of pKEN018 plasmid DNA which had previously been double-digested with Pvu I and Eco RI restriction enzymes and then treated with BAP (as shown at 124 in FIG. 10). The Pvu I and the Eco RI cohesive termini were ligated by treating with 0.4 units of T4 DNA ligase in 50 microliters of ligase buffer containing 0.4 mM ATP at 12.5° C. for 7 hours. Twenty-five microliters of the ligated mixture were used to transform E. coli strain JE5519, NRRL B-15013, and transformants were selected for ampicillin resistance. Plasmid DNAs were isolated from ampicillin-resistant transformants and analyzed by agarose gel electrophoresis. Restriction enzyme mapping indicated that one of the plasmids had the structure shown at 125 in FIG. 10, and this plasmid was designated pKEN021.

6. Construction of Plasmid pKEN037

Figure 11:
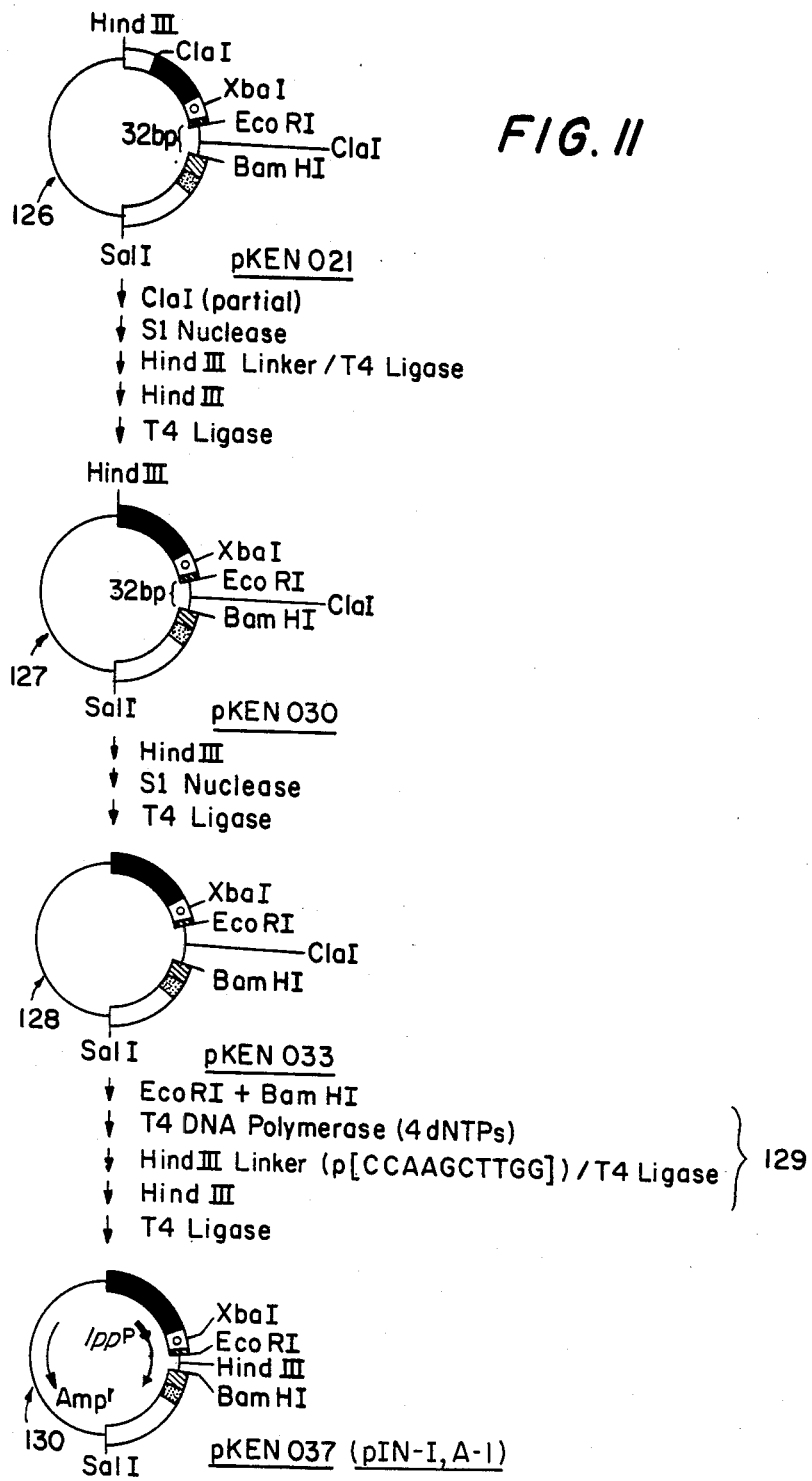

FIG. 11 illustrates the final step in the construction of the first A site lpp gene expression plasmid. As shown at 126 in FIG. 11, pKEN021 carries both the lpp promoter fragment and the lpp transcription terminator fragment, separated by a 32 bp fragment derived from pBR322. By deleting the latter fragment and inserting a DNA sequence coding for a desired polypeptide, a functional moiety for expression of the desired polypeptide is provided. However, since there are Eco RI and Bam HI cleavage sites at the ends of the 32 bp fragment, the structure of plasmid pKEN021 allows only for the insertion of exogenous DNA insert fragments having Eco RI-Eco RI, Bam HI-Bam HI, or Eco RI-Bam HI cohesive termini. Therefore, in order to expand the class of exogenous genes which can be inserted to include those tailored with other combinations of cohesive termini, the DNA sequence in this region was modified to add a Hind III cleavage site between the existing Eco RI and Bam HI sites.

To accomplish this result, it was first desirable to reduce the size of the plasmid by eliminating the 200 bp Hind III-Cla I fragment in pKEN021, using the following procedure: five micrograms of pKEN021 plasmid DNA were partially digested with one unit of Cla I restriction enzyme in 100 microliters of a reaction mixture comprising 10 mM Tris:HCl (pH 8.0), 10 mM MgCl$_2$ and 100 micrograms/ml BSA at 37° C. for one hour. After phenol extraction and ethanol precipitation, Cla I cohesive termini were removed by treating with 600 units of S1 Nuclease in 200 microliters of S1 buffer at 20° C. for one hour. The reaction was terminated by adding 20 microliters of 0.5M Tris:HCl (pH 8.0) and 20 microliters of 0.25M EDTA. The mixture was extracted with phenol and dialyzed for four hours against 0.01×SSC. The DNAs were precipitated with 2.5 volumes of ethanol, centrifuged and resuspended in 100 microliters of 0.3M Na-acetate. The DNAs were re-precipitated with 250 microliters of ethanol, centrifuged, and dried under vacuum.

One microgram of the S1-treated DNA was then mixed with 70 pmoles of phosphorylated Hind III linker (5'CCAAGCTTGG3'; obtained from Collaborative Research and phosphorylated according to the same procedure as described hereinabove) and blunt-end ligated with 4 units of T4 DNA ligase in 20 microliters of ligase buffer containing 0.6 mM ATP at 12.5° C. for 16 hours. The mixture was then diluted to 100 microliters with Hind III buffer and heated at 60° C. for 10 minutes. Twenty units of Hind III restriction endonuclease were added, and the mixture was incubated at 37° C. for one hour to remove superfluous linker molecules and to create Hind III cohesive termini. The reaction mixture was then extracted with phenol, and the DNAs were precipitated with ethanol. Plasmid DNAs (0.5 micrograms) were re-circularized by treating with 0.8 units of T4 DNA ligase in 15 microliters of ligase buffer containing 0.4 mM ATP at 12.5° C. for 7 hours. Eight microliters of the ligated mixture were used to transform E. coli strain JA221, NRRL B-15014 (recA$^-$, hr$^-$, hm$^+$, $\Delta$trpE5, thr, leu, thi, lacY$^-$; obtained from Dr. J. Carbon, Dept. of Biological Sciences, University of California, Santa Barbara). This strain is available to the public from the permanent collection of the Northern Regional Research Laboratory, U.S. Department of Agriculture, Peoria, Ill., U.S.A. Among the plasmid DNAs which were purified from the ampicillin-resistant transformants was one that had the structure shown at 127 in FIG. 11, and this plasmid was designated pKEN030.

In order to eliminate the Hind III cleavage site of pKEN030, 2.5 micrograms of pKEN030 plasmid DNA were digested with 5 units of Hind III restriction enzyme in 50 microliters of Hind III buffer at 37° C. for one hour. After phenol extraction and ethanol precipitation, the Hind III cohesive termini were removed by treating with 400 units of S1 nuclease in 200 microliters of S1 buffer at 20° C. for one hour. Following recovery of the DNA, 0.75 micrograms of the S1-treated plasmid DNAs were re-circularized by treating with 2 units of T4 DNA ligase in 10 microliters of ligase buffer containing 0.6 mM ATP at 12.5° C. for 16 hours. Three microliters of the ligated mixture were then used to transform E. coli strain JA221, NRRL B-15014, and one of the plasmids isolated from the ampicillin-resistant transformants was found to have the structure shown at 128 in FIG. 11. This plasmid, designated pKEN033, contained no Hind III cleavage sites.

Figure 12:
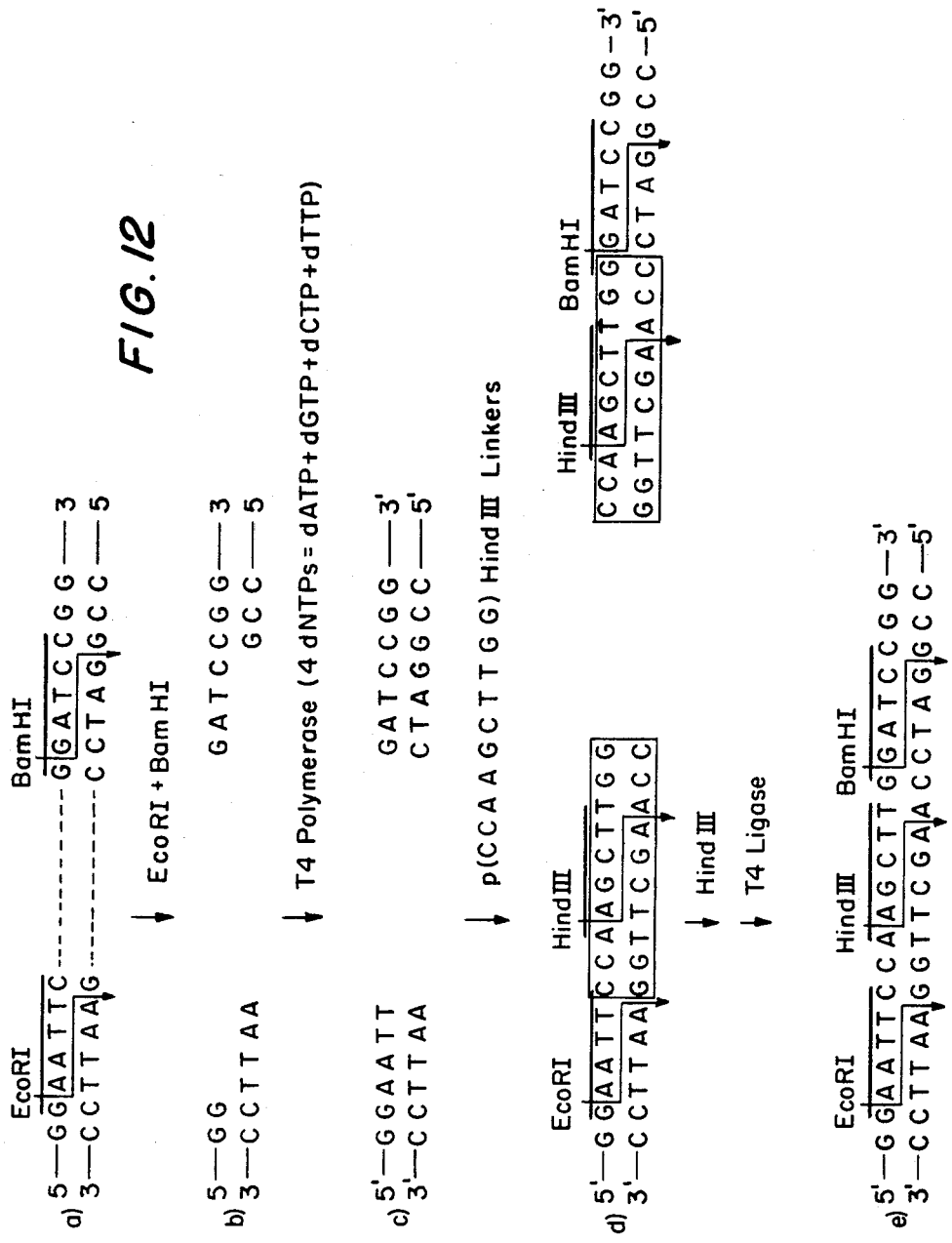

As shown schematically at 129 in FIG. 11, and in more detail in FIG. 12, the DNA sequence of plasmid pKEN033 was modified to create a Hind III cleavage site between the Eco RI and Bam HI sites, as follows: 5 micrograms of pKEN033 plasmid DNA (having the DNA sequence of interest shown in FIG. 12, line a) were digested with 10 units of Bam HI restriction endonuclease in 50 microliters of Bam HI buffer at 37° C. for one hour. After inactivation of the Bam HI enzyme by heating the reaction mixture at 60° C. for 10 minutes, the linearized DNA fragments were further digested with 10 units of Eco RI enzyme in 100 microliters of Eco RI buffer at 37° C. for one hour (see FIG. 12, line b). After phenol extraction and ethanol precipitation, the DNAs (3.6 micrograms) were treated with three units of T4 polymerase (obtained from Bethesda Research Laboratories) in 20 microliters of a reaction mixture containing 50 mM Tris:HCl (pH 8.0), 100 mM KCl, 6 mM MgCl$_2$, and 6 mM dithiothreitol (this reaction mixture will hereinafter be referred to as a "polymerase buffer") in the presence of 0.1 mM each of dATP, dGTP, dCTP and dTTP at 12.5° C. for 45 minutes. By this procedure, the Bam HI and the Eco RI "sticky ends" were filled in completely, as shown in FIG. 12, line c.

After recovery of the DNAs, 300 pmoles of phosphorylated Hind III linker were added, followed by blunt-end ligation with 4 units of T4 DNA ligase in 15 microliters of ligase buffer containing 0.6 mM ATP at 12.5° C. for 16 hours. The mixture was then diluted to 100 microliters with Hind III buffer, and digested with 100 units of Hind III restriction enzyme. The mixture was incubated at 37° C. for one hour to remove superfluous linker molecules and to create Hind III cohesive termini (see FIG. 12, line d), which were later joined (thereby re-circularizing the plasmid DNAs) by treating 0.8 micrograms of the DNA with 0.4 units of T4 DNA ligase in 20 microliters of ligase buffer containing 0.4 mM ATP at 12.5° C. for 7 hours. Following transformation of *E. coli* strain JA221, NRRL B-15014, with a portion of the ligated mixture, plasmid DNAs were isolated from the ampicillin-resistant colonies, and one of them had the structure indicated at 130 in FIG. 11 and was designated pKEN037. Analysis of the DNA nucleotide sequence of pKEN037 revealed the DNA sequence depicted in FIG. 12, line e, in which one G-C pair was deleted between the Hind III and Bam HI cleavage sites (for reasons which are presently unknown), and confirmed that pKEN037 was the constitutive A-1 cloning vehicle.

7. Construction of Plasmids pKEN039 and pKEN040

Figure 13:
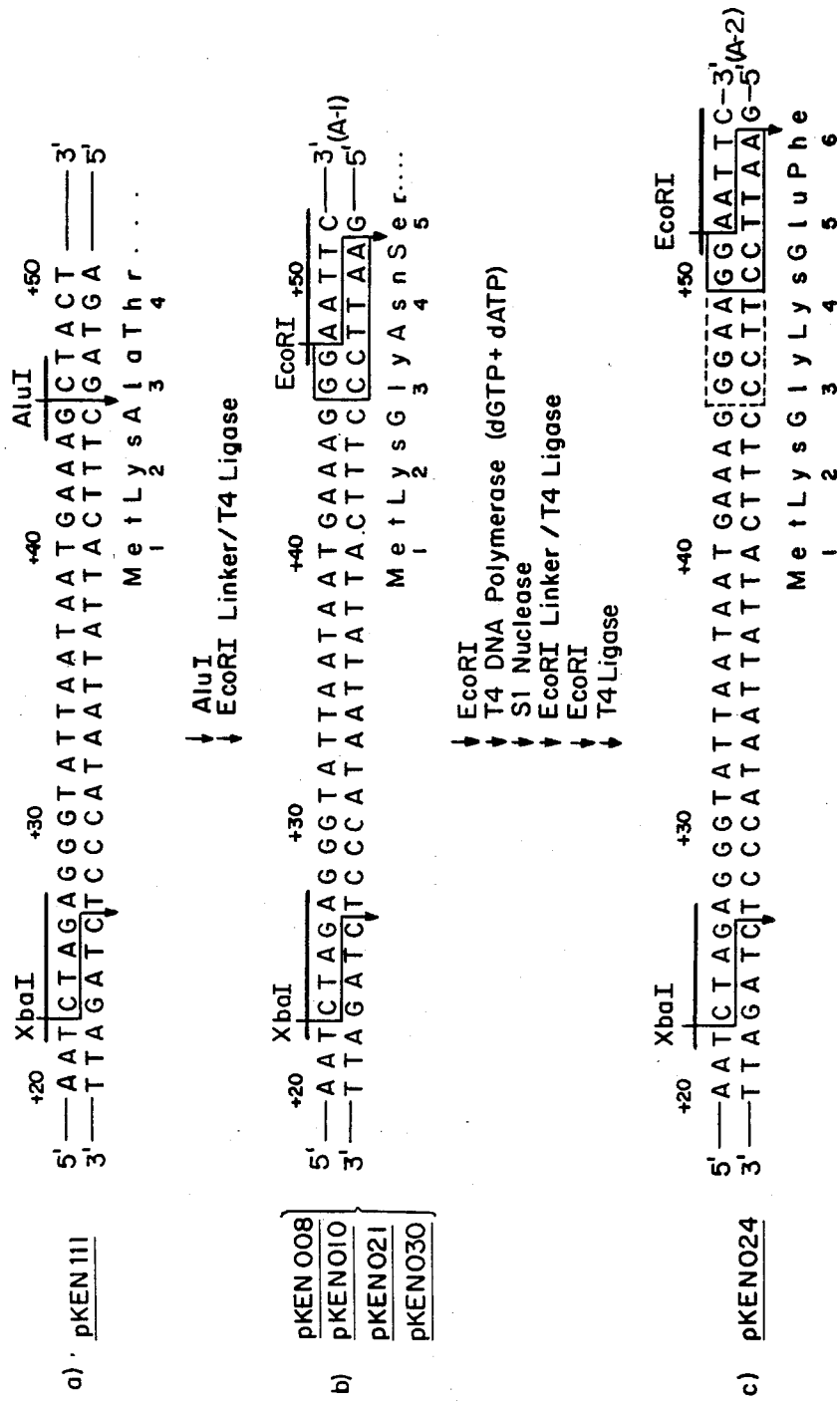
Figure 14:
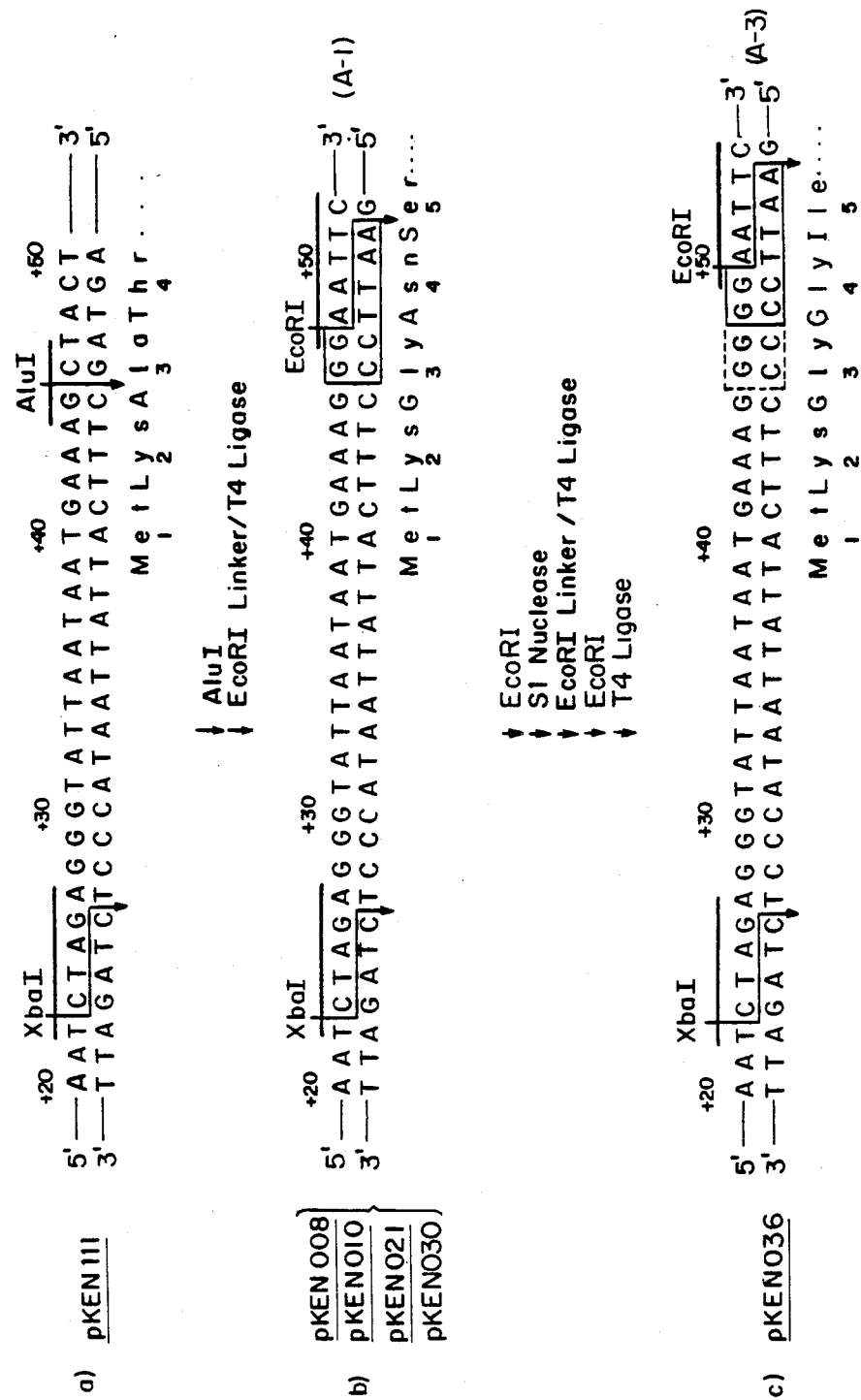

In order to accommodate DNA insert fragments with reading frames differing from that of pKEN037, the constitutive A-2 and A-3 lpp gene cloning vehicles were constructed by adjusting the reading frame of pKEN030 at the Eco RI cleavage site. FIG. 13, line a, and FIG. 14, line a, both illustrate the DNA sequence surrounding the translation initiation site of the prolipoprotein in pKEN111. As shown, this sequence includes an Alu I cleavage site between positions +45 and +46. In creating plasmid pKEN008, an Eco RI linker was attached to the Alu I terminus, resulting in the DNA sequence shown in FIG. 13, line b, and in FIG. 14, line b, in plasmids pKEN008, pKEN010, pKEN021 and pKEN030, and creating an Eco RI cleavage site between positions +47 and +48. The DNA sequence of pKEN030 was modified at the Eco RI site, as shown in FIG. 13, line c, and in FIG. 14, line c, to shift its reading frame by one base and by two bases, respectively.

To accomplish this result in the first case to produce a plasmid with the A-2 reading frame, 5 micrograms of pKEN030 plasmid DNA were digested completely with Eco RI restriction enzyme in 100 microliters of Eco RI buffer at 37° C. for 60 minutes. After phenol extraction and ethanol precipitation, the DNAs were treated with 3 units of T4 DNA polymerase in 30 microliters of polymerase buffer in the presence of 0.1 mM dGTP and 0.1 mM dATP at 12.5° C. for 45 minutes. The reaction was terminated by adding EDTA to a final concentration of 25 mM, followed by phenol extraction. By this procedure, half of the 4-base Eco RI "sticky end" was filled in with two A residues. The remaining two single-strand A residues were removed by treating with S1 Nuclease in 200 microliters of S1 buffer at 20° C. for one hour. The reaction was terminated by adding 20 microliters of 0.5M Tris:HCl (pH 8.0) and 20 microliters of 0.25M EDTA. The mixture was extracted with phenol and dialyzed overnight against 0.01×SSC. The DNAs were precipitated with 2.5 volumes of ethanol, centrifuged and re-suspended in 100 microliters of 0.3M Na-acetate. The DNAs were re-precipitated with 250 microliters of ethanol, centrifuged, and dried under vacuum.

In order to restore the Eco RI cleavage site, one microgram of the S1-treated DNA was first mixed with 70 pmoles of phosphorylated Eco RI linker and blunt-end ligated with 3.2 units of T4 DNA ligase in 11 microliters of ligase buffer containing 0.6 mM ATP at 12.5° C. for 16 hours. The mixture was then diluted to 50 microliters with Eco RI buffer and heated at 60° C. for 10 minutes. Twenty units of Eco RI restriction endonuclease were added, and the mixture was incubated at 37° C. for one hour to remove superfluous linker molecules and to create Eco RI cohesive termini. The reaction mixture was then extracted with phenol, and the DNAs were precipitated with ethanol. Plasmid DNAs (0.5 micrograms) were re-circularized by treating with 0.8 units of T4 DNA ligase in 15 microliters of ligase buffer containing 0.4 mM ATP at 12.5° C. for 7 hours. Eight microliters of the ligated mixture were used to transform *E. coli* strain JA221, NRRL B-15014. Plasmid DNAs were purified from 3 ampicillin-resistant transformants, which had been grown overnight in one hundred ml of L broth containing 50 micrograms/ml of ampicillin, and the DNA sequences at their Eco RI cleavage sites were determined. One of them was found to have the sequence shown in FIG. 13, line c, and was designated pKEN024 (A-2).

To construct a plasmid with the A-3 reading frame, 5 micrograms of pKEN030 plasmid DNA were digested completely with Eco RI restriction enzyme in 100 microliters of Eco RI buffer at 37° C. for 60 minutes. After phenol extraction and ethanol precipitation, the Eco RI "sticky ends" were removed by treating the DNA (4.4 micrograms) with 500 units of S1 Nuclease in 150 microliters of S1 buffer at 20° C. for one hour. The reaction was terminated by adding 15 microliters of 0.5M Tris:HCl (pH 8.0) and 15 microliters of 0.25M EDTA. The mixture was extracted with phenol and dialyzed for four hours against 0.01×SSC. The DNAs were precipitated with 2.5 volumes of ethanol, centrifuged and re-suspended in 100 microliters in 0.3 Na-acetate. The DNAs were re-precipitated with 250 microliters of ethanol, centrifuged, and dried under vacuum.

In order to restore the Eco RI cleavage site, one microgram of the S1-treated DNA was first mixed with 240 pmoles of phosphorylated Eco RI linker and blunt-end ligated with 4 units of T4 DNA ligase in 15 microliters of ligase buffer containing 0.6 mM ATP at 12.5° C. for 16 hours. The mixture was then diluted to 250 microliters with Eco RI buffer and heated at 60° C. for 10 minutes. One hundred units of Eco RI restriction endonuclease were added, and the mixture was incubated at 37° C. for one hour to remove superfluous linker molecules and to create Eco RI cohesive termini. The reaction mixture was then extracted with phenol, and the DNAs were precipitated with ethanol. Plasmid DNAs (0.3 micrograms) were re-circularized by treating with 0.8 units of T4 DNA ligase in 15 microliters of ligase buffer containing 0.4 mM ATP at 12.5° C. for 7 hours. Eight microliters of the ligated mixture were used to transform *E. coli* strain JA221, NRRL B-15014. Plasmid DNAs were purified from 3 ampicillin-resistant transformants, which had been grown overnight in one hundred ml of L broth containing 50 micrograms/ml of ampicillin, and the DNA sequences at their Eco RI cleavage sites were determined. One of them was found to have the sequence shown in FIG. 14, line c, and was designed pKEN036 (A-3).

Figure 15:
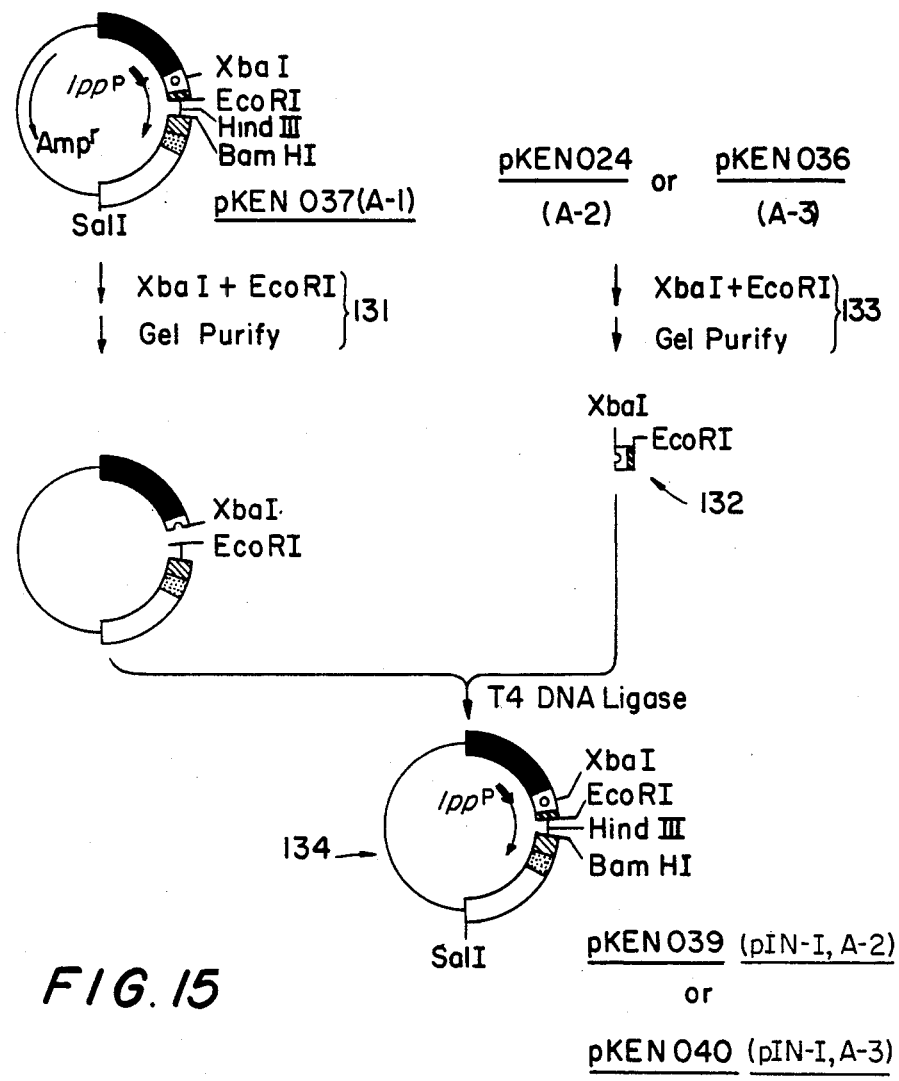

To change the translational reading frame of pKEN037 (A-1) into the two other reading frames (A-2 and A-3), the smaller Xba I-Eco RI fragment of pKEN037 was replaced with the smaller Xba I-Eco RI fragments from pKEN024 (A-2) or pKEN036 (A-3), as shown schematically in FIG. 15, using the following procedure: 3 micrograms of pKEN037 were first digested (as shown at 131 in FIG. 15) with 6 units of Xba I restriction enzyme in 50 microliters of Bam HI buffer at 37° C. for one hour, and after inactivation of the Xba I enzyme, the linearized DNA fragments were further digested with 6 units of Eco RI restriction enzyme in 100 microliters of Eco RI buffer at 37° C. for one hour. The larger Xba I-Eco RI fragment was separated from the smaller fragment by agarose gel electrophoresis: the DNA fragments in the agarose gel were stained with ethidium bromide (one microgram/ml), and the band corresponding to the larger fragment was cut out. The DNA fragments in this band were eluted from the gel after freezing. Ethidium bromide was removed from the DNA fragments by phenol extraction, and the DNAs were recovered by ethanol precipitation.

The dried DNA fragments were dissolved in 20 microliters of water, and one microliter aliquots of this pKEN037 DNA fragment mixture were combined with 0.1 micrograms of each of the smaller Xba I-Eco RI restriction fragments (illustrated at 132 in FIG. 15) previously obtained from pKEN024 or pKEN036 by double-digestion of each plasmid with Xba I and Eco RI restriction enzymes followed by gel purification (as shown at 133 in FIG. 15). The "sticky ends" of the Xba I-Eco RI fragments were joined by treatment with 0.2 units of T4 DNA ligase in 20 microliters of ligase buffer containing 0.4 mM ATP at 12.5° C. for 7 hours, following which a portion of the ligated mixture was used to transform E. coli strain JA221, NRRL B-15014. Among the ampicillin-resistant transformants, plasmid DNAs having the A-2 and A-3 reading frames were obtained, and these were designated pKEN039 and pKEN040, respectively, each having the structure shown at 134 in FIG. 15.

It will be appreciated that the foregoing was the experimental procedure used to construct plasmids pKEN039 (A-2) and pKEN040 (A-3) in the first instance. However, it will be understood by those skilled in the art that an alternative method exists with which to construct those plasmids. Specifically, the DNA sequence in the vicinity of the Eco RI cleavage site of plasmid pKEN037 (A-1) can itself be modified according to the scheme illustrated in FIG. 13, lines b and c, or the scheme shown in FIG. 14, lines b and c, to yield directly the structure of plasmids pKEN039 (A-2) or pKEN040 (A-3), respectively.

B. Construction of B Site Plasmids (pIN-I)

FIGS. 16-21 schematically illustrate the manner in which constitutive recombinant plasmids incorporating the B insertion site were constructed, and may be referred to in connection with the following more particularized discussion.

1. Construction of Plasmid pKEN221

The first step in the construction of the B site expression plasmids was to construct a plasmid to serve as a source of lpp gene fragments having a restriction enzyme cleavage site at or near the signal peptide cleavage site. The gene chosen codes for the lipoprotein of S. marcescens, and has a Fnu4H-I restriction endonuclease recognition sequence at the 3' end of the signal peptide. The plasmid chosen to receive the S. marcescens lpp gene was pBR322.

Figure 16:
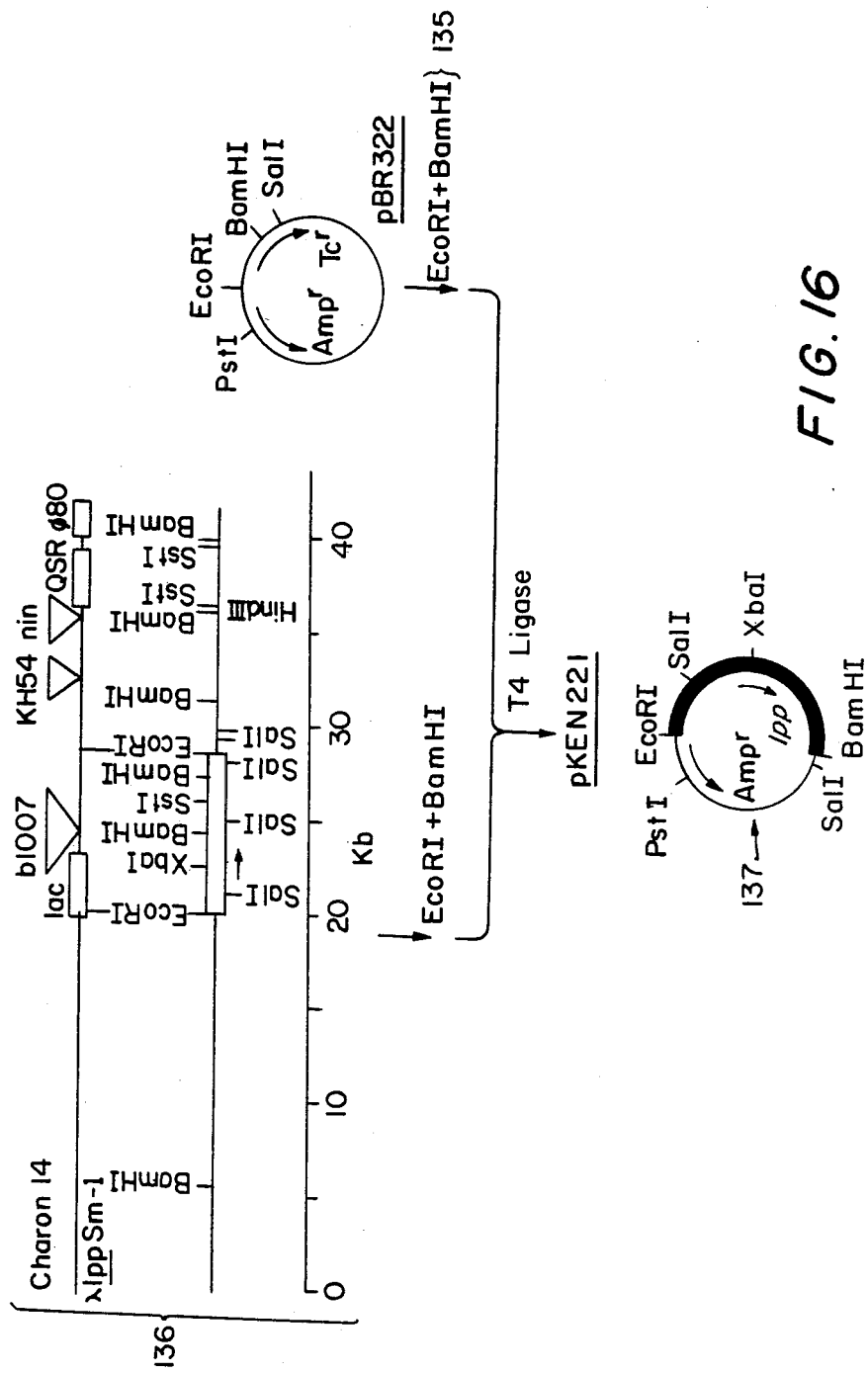

As shown schematically at 135 in FIG. 16, 2 micrograms of plasmid pBR322 DNA were digested to completion with two units of the restriction endonuclease Bam HI in 50 microliters of Bam HI buffer at 37° C. for 60 minutes. After inactivation of Bam HI enzyme by heating at 60° C. for 10 minutes, 2 units of Eco RI and 100 microliters of Eco RI buffer were added. The mixture was further incubated at 37° C. for 60 minutes, and the reaction was then terminated by phenol extraction, after which the linearized DNA fragments were recovered by ethanol precipitation.

An 8.5 Kb DNA fragment containing the S. marcescens lpp gene was separately derived, as shown at 136 in FIG. 16, from a hybrid λ phage carrying the S. marcescens lpp gene (designated λlppSm-1). The lpp gene had previously been cloned into a λ phage vector, Charon 14 (Blattner, F., et al., Science 196: 161-169 [1977]), as follows: Total DNA (200 micrograms) isolated from S. marcescens was digested with 200 units of the restriction enzyme Eco RI. DNA fragments were separated on a preparative agarose gel, and fractions of DNA fragments of approximately 8.5 Kb which showed positive hybridization with $5'$-$^{32}$p-lipoprotein mRNA were collected, using the Southern hybridization technique. A mixture of 8.5 Kb Eco RI fragments (enriched approximately twenty-fold) and Eco RI-cleaved Charon 14 vector DNA was reacted with T4 DNA ligase. Ligated DNA was used to transfect E. coli K802, NRRL B-15016. Recombinant phages carrying the lpp gene were screened by the plaque hybridization technique of Benton and Davis using $5'$-$^{32}$p-lipoprotein mRNA. One of the plaques examined which gave positive hybridization was designated λlppSm-1.

The micrograms of λlppSm-1 DNA were then digested completely with the restriction enzymes Bam HI and Eco RI, in the same manner as described immediately above with respect to linearization of pBR322, and 0.5 micrograms of the λlppSm-1 DNA fragments were combined with 0.5 micrograms of the previously-linearized plasmid pBR322 DNA in 40 microliters of ligase buffer. The mixture was heated at 37° C. for 5 minutes, and the Eco RI and Bam HI cohesive termini were annealed by incubating at 4° C. for 16 hours and then at 0° C. for 1 hour. After adding ATP (0.4 mM final) and 0.4 units of T4 DNA ligase, the mixture was incubated at 12.5° C. for 7 hours.

One-fourth of the ligation mixture was thereafter used to transform E. coli lpp deletion mutant strain JE5527, NRRL B-15012. Transformation was carried out as described in Cohen, S. N., et al., Proc. Natl. Acad. Sci U.S.A. 69: 2110-2114 (1972), and ampicillin-resistant transformants were grown overnight on Whatman 3MM filter papers, placed on the surface of an L broth plate containing 50 micrograms/ml of ampicillin, and screened for lpp clones by colony hybridization. A 0.95 Kb Msp I fragment of λlppEc-1 containing the lpp gene was nick-translated with [α-$^{32}$p]dATP and [α-$^{32}$p]dCTP, as described in Maniatis, T., et al., Proc. Natl. Acad. Sci. U.S.A. 72: 1184-1188 (1975), and was used as a $^{32}$p-probe. One of the transformants which gave positive hybridization was shown to contain the plasmid with the structure illustrated at 137 in FIG. 16, and this plasmid was designated pKEN221.

2. Construction of Plasmid pKEN009

Figure 17:
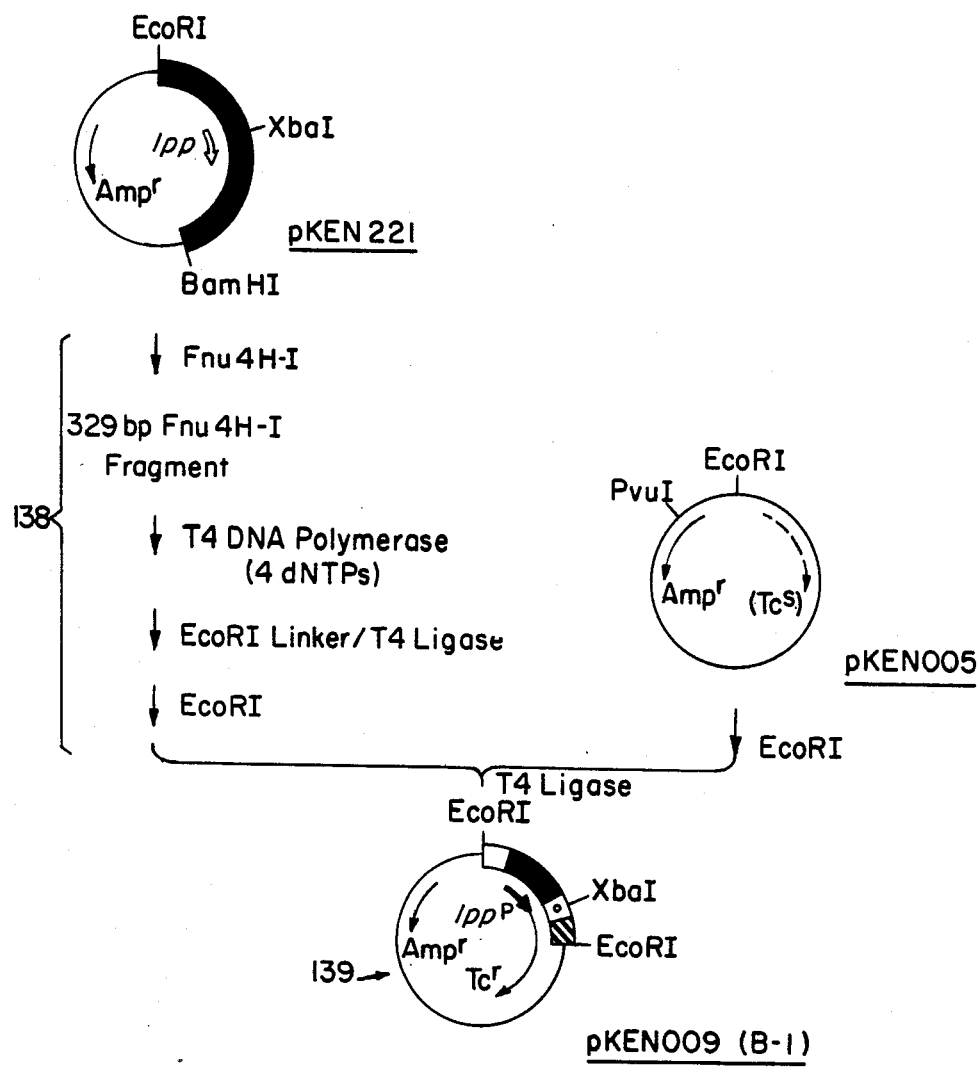

In order to construct the B site cloning vehicles, a 329 bp Fnu4H-I fragment containing the lpp promoter and 5'-untranslated region, as well as the signal peptide region of the *S. marcescens* lpp gene (this fragment is shown schematically at 105B in FIG. 5) was first cloned into pKEN005, as illustrated at 138 in FIG. 17, as follows: 80 micrograms of pKEN221 plasmid DNA were digested to completion with 100 units of the restriction endonuclease Fnu4H-I (New England Biolabs) in 400 microliters of Hae III buffer, and a 324 bp Fnu4H-I fragment was purified by acrylamide gel electrophoresis.

Since digestion with Fnu4H-I restriction enzyme results in the production of fragments with "sticky ends" at both termini, these sticky ends were modified by filling in with T4 DNA polymerase to create blunt ends. Two micrograms of the purified 324 bp Fnu4H-I fragment were treated with 3 units of T4 DNA polymerase in 20 microliters of polymerase buffer in the presence of 0.1 mM each of dATP, dGTP, dCTP and dTTP at 12.5° C. for 45 minutes. After phenol extraction and ethanol precipitation, the DNA fragments were mixed with 400 pmoles of phosphorylated Eco RI linker and treated with 4 units of T4 DNA ligase in 20 microliters of ligase buffer containing 0.6 mM ATP at 12.5° C. for 16 hours. The mixture was diluted to 300 microliters with Eco RI buffer and digested with 150 units of Eco RI restriction enzyme to create Eco RI cohesive termini.

One microgram of the Eco RI-digested fragments was then mixed with 0.5 micrograms of Eco RI-digested pKEN005 plasmid DNA, and treated with 0.4 units of T4 DNA ligase in 40 microliters of ligase buffer containing 0.6 mM ATP at 12.5° C. for 16 hours. Twenty microliters of the ligated mixture were used to transform *E. coli* strain JE5519, NRRL B-15013. Upon restriction enzyme analysis of the plasmid DNAs obtained from tetracycline-resistant transformants by the rapid alkaline denaturation method, one of the plasmids was found to carry a 334 bp Eco RI fragment derived from the 329 bp Fnu4H-I fragment, and this plasmid (depicted schematically at 139 in FIG. 17) was designated pKEN009. DNA nucleotide sequence analysis of the pKEN009 plasmid DNA showed that the Eco RI site in pKEN009 lies at the B insertion site and corresponds with the B-1 reading frame. This plasmid had the DNA sequence illustrated in FIG. 19, line b, and in FIG. 20, line b. For reasons which are not understood at present, it was found that three base pairs had been inserted in the region of position +90 (resulting in the addition of one extra amino acid residue at this position) and that an extra G-C pair had been inserted at position +99. The surprising cumulative effect of these changes was to convert the amino acid sequence in the region of the signal peptide cleavage site from that of the *S. marcescens* lpp gene to that of the *E. coli* lpp gene.

3. Construction of Plasmids pKEN017, pKEN026 and pKEN027

Figure 18:
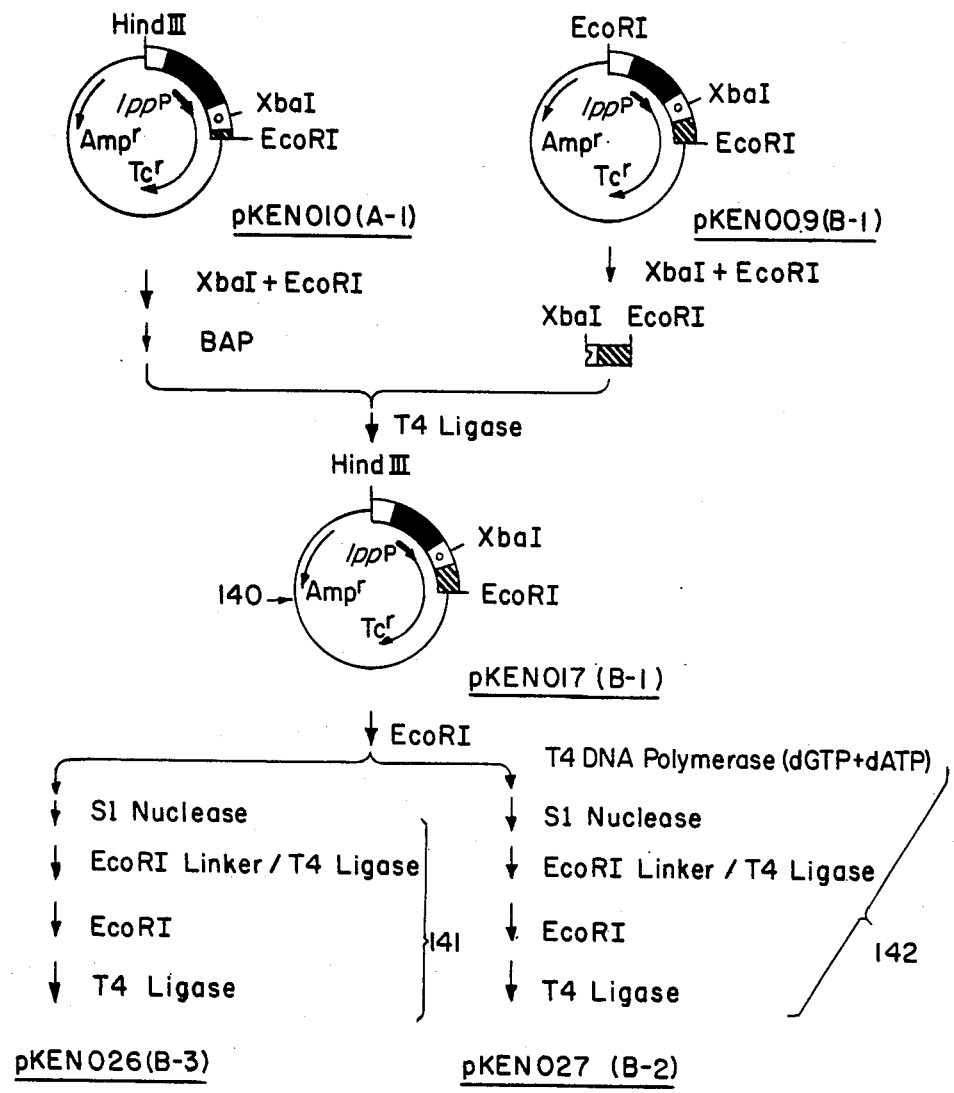

In order to construct constitutive B site expression plasmids corresponding to the B-2 and B-3 reading frames, it was first necessary to eliminate one of the two Eco RI cleavage sites of pKEN009. FIG. 18 depicts schematically the strategy for removing the Eco RI site located upstream of the lpp promoter. This procedure involved transferring an 80 bp Xba I-Eco RI fragment (containing the signal peptide and a portion of the 5'-untranslated region of the *S. marcescens* lpp gene) from pKEN009 into the Xba I-Eco RI sites of pKEN010.

In order to accomplish this result, 5 micrograms of pKEN010 plasmid DNA were first digested with 5 units of Xba I restriction endonuclease in 50 microliters of Bam HI buffer, followed by digestion with 5 units of Eco RI restriction enzyme in 100 microliters of Eco RI buffer. The linearized DNA was then treated with 5 microliters of BAP in 100 microliters of 10 mM Tris:HCl (pH 8.0) and 0.1 mM EDTA at 37° C. for 30 minutes. Plasmid DNAs were extracted with phenol and precipitated with ethanol, and 0.5 micrograms of the DNA were mixed with 0.2 micrograms of an 80 bp Xba I-Eco RI fragment, which has previously been obtained by digestion of 50 micrograms of pKEN009 plasmid DNA by Eco RI and Xba I restriction enzymes, followed by polyacrylamide gel electrophoresis. The DNA mixture was treated with 0.4 units of T4 DNA ligase in 40 microliters of ligase buffer containing 0.4 mM ATP at 12.5° C. for 16 hours. Twenty microliters of the ligated mixture were used to transform *E. coli* strain JE5519, NRRL B-15013. Upon restriction enzyme analysis of the plasmid DNAs obtained from ampicillin-resistant transformants by the rapid alkaline denaturation method, one plasmid was found to contain the desired 80 bp Xba I-Eco RI fragment carrying the signal peptide region of the *S. marcescens* lpp gene in the B-1 reading frame, as shown at 140 in FIG. 18, and that plasmid was designated pKEN017.

Figure 19:
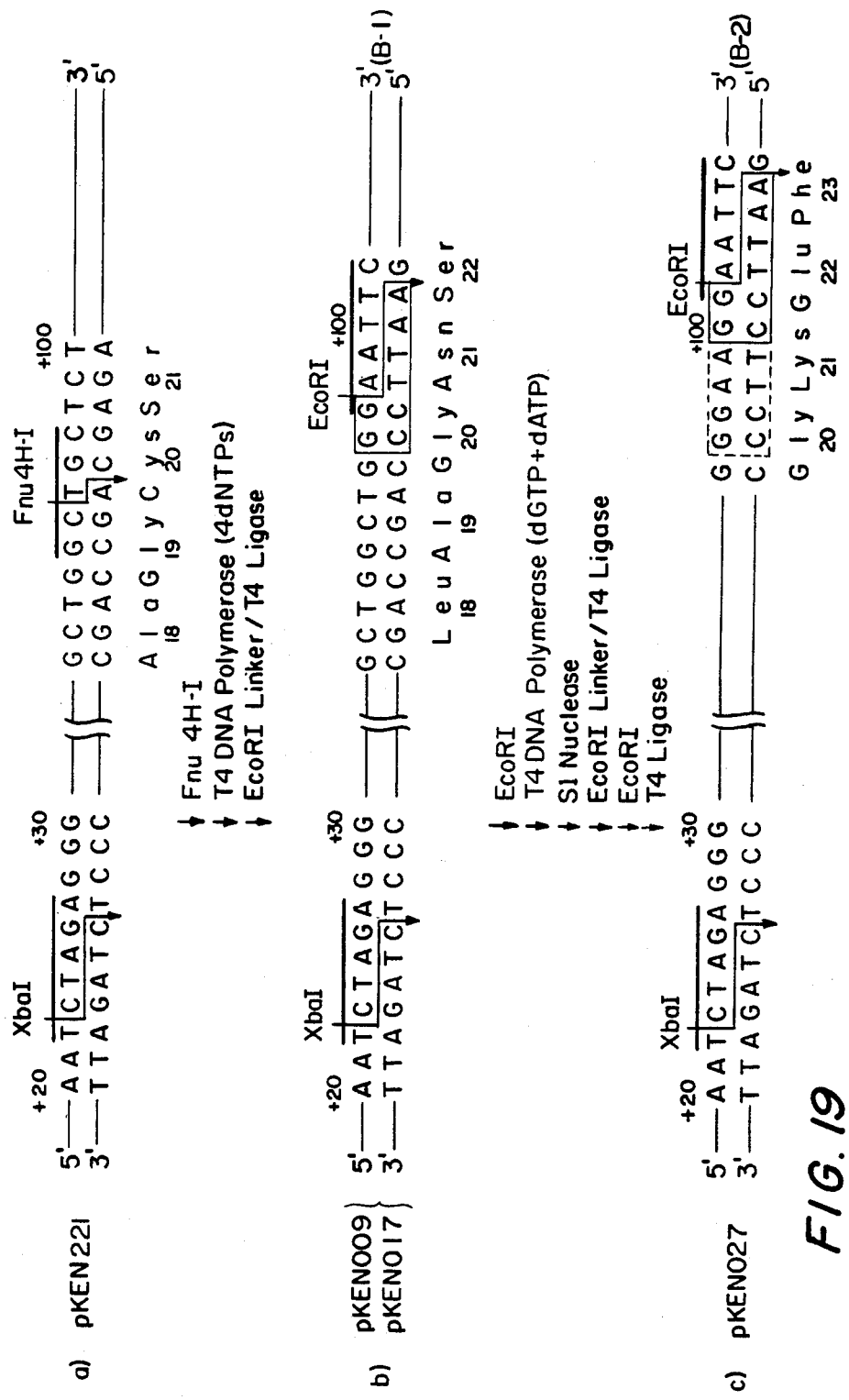
Figure 20:
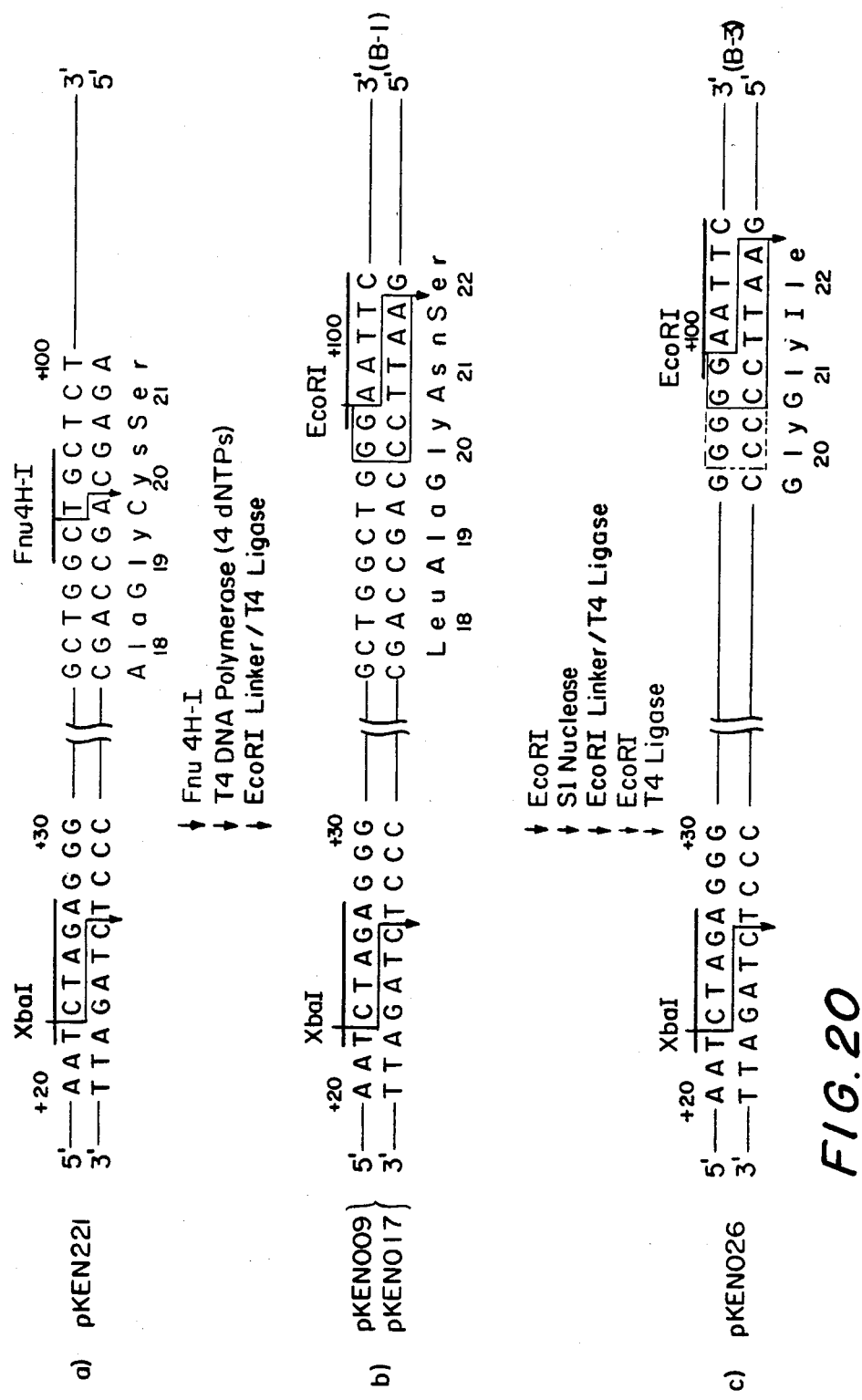

The reading frame at the B insertion site in pKEN017 was then modified to yield plasmids corresponding to the B-2 and B-3 reading frames, according to the methods previously described for changing the A-1 reading frame into the A-2 or A-3 reading frames, respectively. These procedures are illustrated schematically at 141 and 142 in FIG. 18, and the corresponding modifications of the DNA sequence around the Eco RI cleavage site are shown in FIGS. 19 and 20. It will be understood that the same procedures used to derive plasmids pKEN024 (A-2) and pKEN036 (A-3) from plasmid pKEN030 (A-1), described hereinabove in connection with FIGS. 13 and 14, can be used to derive plasmids pKEN026 (B-3) and pKEN027 (B-2) from plasmid pKEN017 (B-1).

4. Construction of Plasmids pKEN041, pKEN047 and pKEN048

Figure 21:
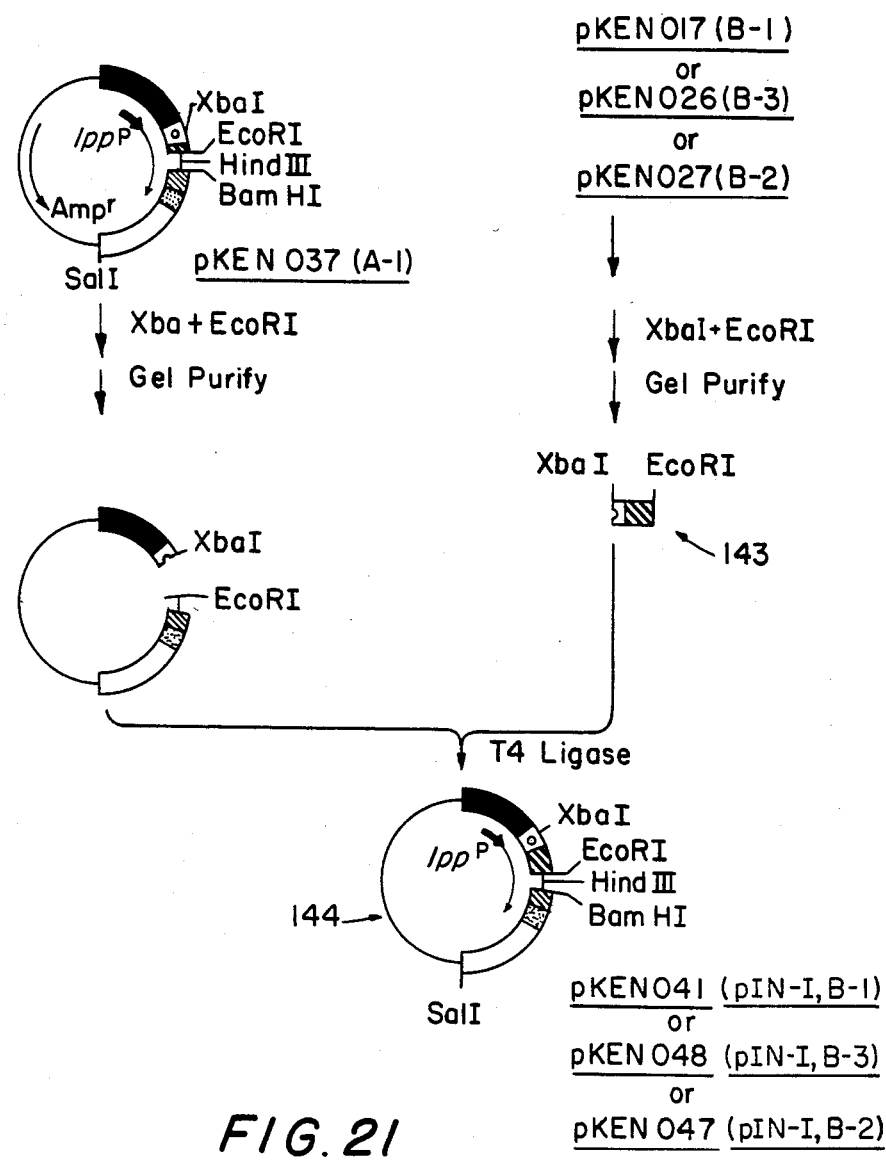

FIG. 21 illustrates schematically the last step in the construction of the B site cloning vehicles, which was to replace the Xba I-Eco RI A site fragment of pKEN037 with each of the three different Xba I-Eco RI B site fragments of pKEN017, pKEN026 and pKEN027. This was necessary in order to provide the B site plasmids with the same sequence of Eco RI, Hind III and Bam HI restriction enzyme recognition sequences at the exogenous DNA insertion site as contained in the A site plasmids. As shown schematically at 143 in FIG. 21, each of the three B site fragments derived from pKEN017, pKEN026 and pKEN027 contains the DNA sequence including the signal peptide obtained from the Fnu4H-I fragment of the *S. marcescens* lpp gene.

In order to accomplish this result, the same procedure was used to obtain the larger Xba I-Eco RI fragment of plasmid pKEN037 as was described hereinabove in connection with FIG. 15. One microliter aliquots of the aqueous pKEN037 DNA fragment mixture were each combined with a different Xba I-Eco RI smaller fragment (about 0.1 micrograms of each) previously obtained from pKEN017, pKEN026 and pKEN027, respectively, by double-digestion with Xba I and Eco RI restriction enzymes followed by gel purification. Each DNA mixture was treated with 0.2 units of T4 DNA ligase in 20 microliters of ligase buffer containing 0.4 mm ATP at 12.5° C. for 16 hours. Ten microliters of each of the ligated mixtures were used to transform *E. coli* strain JA221, NRRL B-15014. Among the ampicillin-resistant transformants, plasmid DNAs having the B-1, B-2 and B-3 reading frames were purified, and these were designated pKEN041, pKEN047 and pKEN048, respectively, each having the structure shown at 144 in FIG. 21.

C. Construction of C Site Plasmids (pIN-I)

FIGS. 22–26 schematically illustrate the manner in which constitutive recombinant plasmids incorporating the C insertion site were constructed, and may be referred to in connection with the following more particularized discussion.

1. Construction of Plasmid pKEN006

Figure 22:
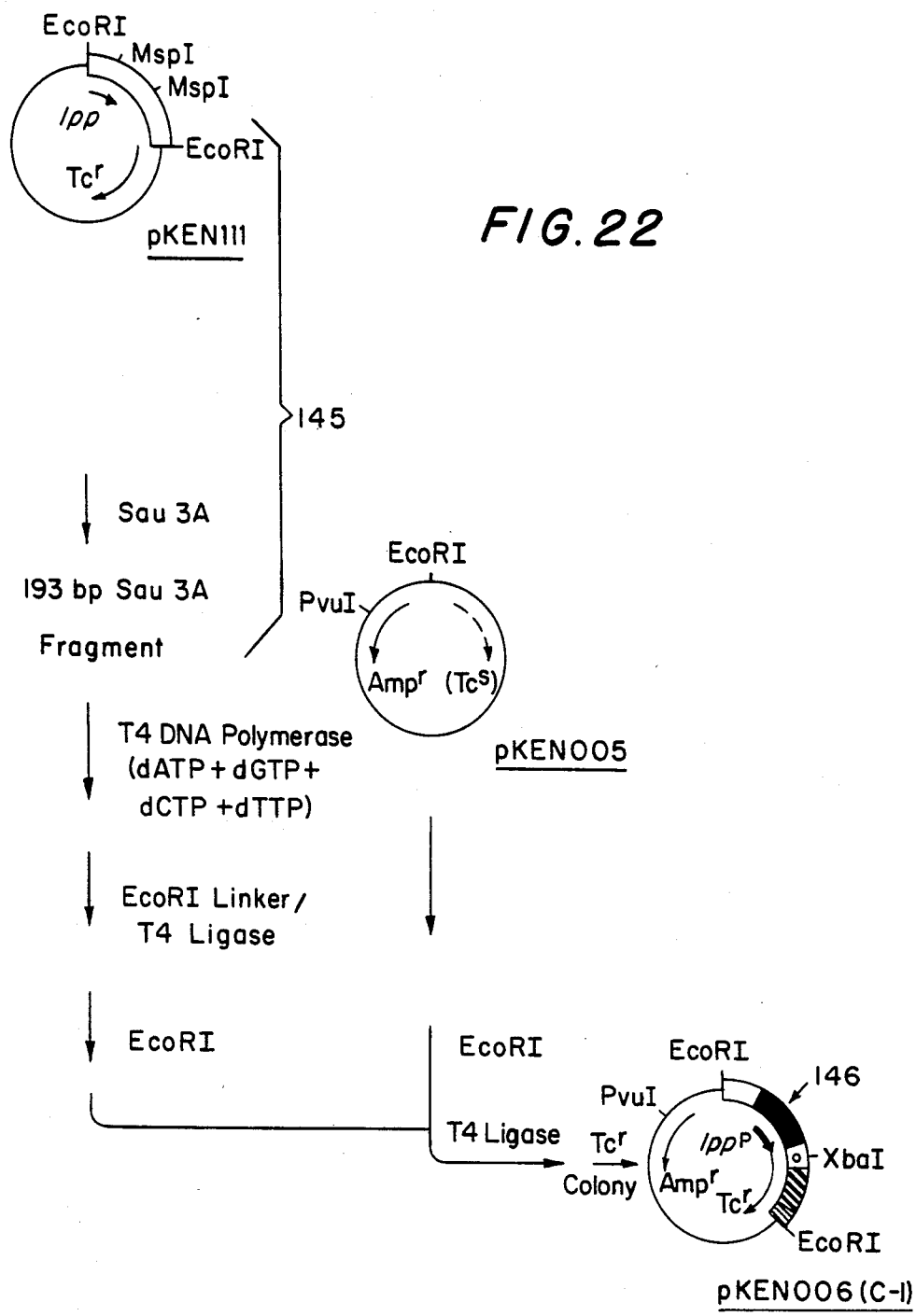

In order to construct the C site cloning vehicles, a 193 bp Sau 3A fragment containing the lpp promoter and 5'-untranslated region, as well as the signal peptide region and the first eight structural codons of the *E. coli* lpp gene (this fragment is shown schematically at 105C in FIG. 5) was first cloned into pKEN005, as illustrated at 145 in FIG. 22, as follows: 200 micrograms of pKEN111 plasmid DNA, which can be obtained by conventional means from *E. coli* CC620/pKEN111, NRRL B-15011, were digested to completion with 200 units of Sau 3A restriction endonuclease in 400 microliters of a reaction mixture comprising 10 mM Tris:HCl (pH 7.5), 10 mM MgCl₂, 60 mM NaCl, and 100 micrograms/ml BSA at 37° C. for one hour. After digestion was completed, phenol extraction was performed, the DNAs were recovered by ethanol precipitation, and a 193 bp Sau 3A fragment was purified by acrylamide gel electrophoresis.

Since digestion with Sau 3A restriction enzyme results in the production of fragments with "sticky ends" at both termini, these sticky ends were modified by filling in with T4 DNA polymerase to create blunt ends. Two micrograms of the purified 193 bp Sau 3A fragment were treated with 3 units of T4 DNA polymerase in 20 microliters of polymerase buffer in the presence of 0.1 mM each of dATP, dGTP, dCTP and dTTP at 12.5° C. for 45 minutes. After phenol extraction and ethanol precipitation, the DNA fragments were mixed with 400 pmoles of phosphorylated Eco RI linker and treated with 4 units of T4 DNA ligase in 20 microliters of ligase buffer containing 0.6 mM ATP at 12.5° C. for 16 hours. The mixture was diluted to 300 microliters with Eco RI buffer and digested with 150 units of Eco RI restriction enzyme to create Eco RI cohesive termini.

One microgram of the Eco RI-digested fragments was then mixed with 0.5 micrograms of Eco RI-digested pKEN005 plasmid DNA, and treated with 0.4 units of T4 DNA ligase in 40 microliters of ligase buffer containing 0.6 mM ATP at 12.5° C. for 16 hours. Twenty microliters of the ligated mixture were used to transform *E. coli* strain JE5519, NRRL B-15013. Upon restriction enzyme analysis of the plasmid DNAs obtained from tetracycline-resistant transformants by the rapid alkaline denaturation method, one of the plasmids was found to carry an Eco RI fragment derived from the 193 bp Sau 3A fragment, and this plasmid (depicted schematically at 146 in FIG. 22) was designated pKEN006. DNA nucleotide sequence analysis of the pKEN006 plasmid DNA showed that the Eco RI site in pKEN006 lies at the C insertion site and corresponds with the C-1 reading frame.

2. Construction of Plasmids pKEN007, pKEN019 and pKEN046

Figure 23:
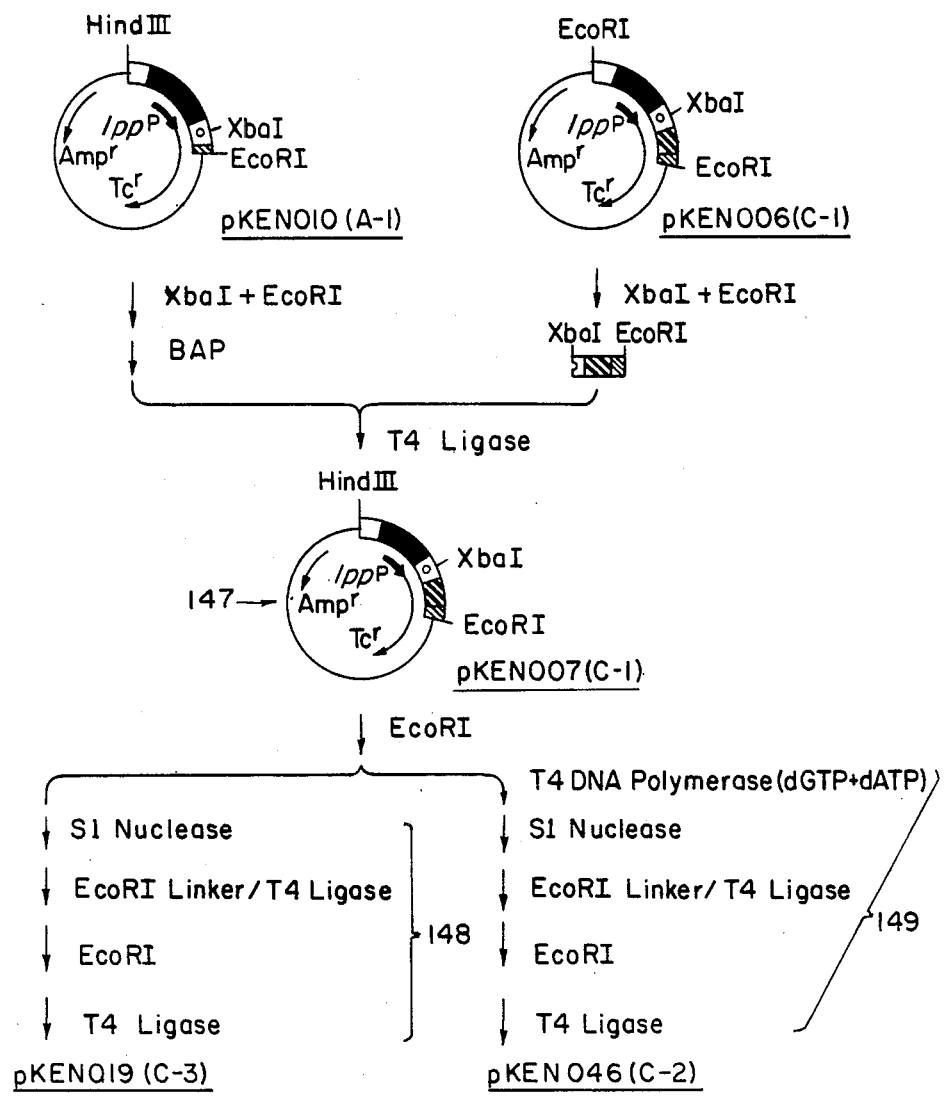

In order to construct C site expression plasmids corresponding to the C-2 and C-3 reading frames, it was first necessary to eliminate one of the two Eco RI cleavage sites of pKEN006. FIG. 23 depicts schematically the strategy for removing the Eco RI site located upstream of the 1 pp promoter. This procedure involved transferring a 106 bp Xba I-Eco RI fragment (containing the signal peptide, a portion of the 5'-untranslated region and a portion of the structural sequence of the *E. coli* 1 pp gene) from pKEN006 into the Xba I-Eco RI sites of pKEN010.

In order to accomplish this result, 5 micrograms of pKEN010 plasmid DNA were first digested with 5 units of Xba I restriction endonuclease in 50 microliters of Bam HI buffer, followed by digestion with 5 units of Eco RI restriction enzyme in 100 microliters of Eco RI buffer. The linearized DNA was then treated with 5 microliters of BAP in 100 microliters of 10 mM Tris:HCl (pH 8.0) and 0.1 mM EDTA at 37° C. for 30 minutes. Plasmid DNAs were extracted with phenol and precipitated with ethanol, and 0.5 micrograms of the DNA were mixed with 0.2 micrograms of a 106 bp Xba I-Eco RI fragment, which has previously been obtained by digestion of 50 micrograms of pKEN006 plasmid DNA by Eco RI and Xba I restriction enzymes, followed by polyacrylamide gel electrophoresis. The DNA mixture was treated with 0.4 units of T4 DNA ligase in 40 microliters of ligase buffer containing 0.4 mM ATP at 12.5° C. for 7 hours. Twenty microliters of the ligated mixture were used to transform *E. coli* strain JE5519, NRRL B-15013. Upon restriction enzyme analysis of the plasmid DNAs obtained from ampicillin-resistant transformants by the rapid alkaline denaturation method, one plasmid was found to contain the desired 106 bp I-Eco RI fragment carrying the signal peptide region of the *E. coli* 1 pp gene in the C-1 reading frame, as shown at 147 in FIG. 23, and that plasmid was designated pKEN007.

Figure 24:
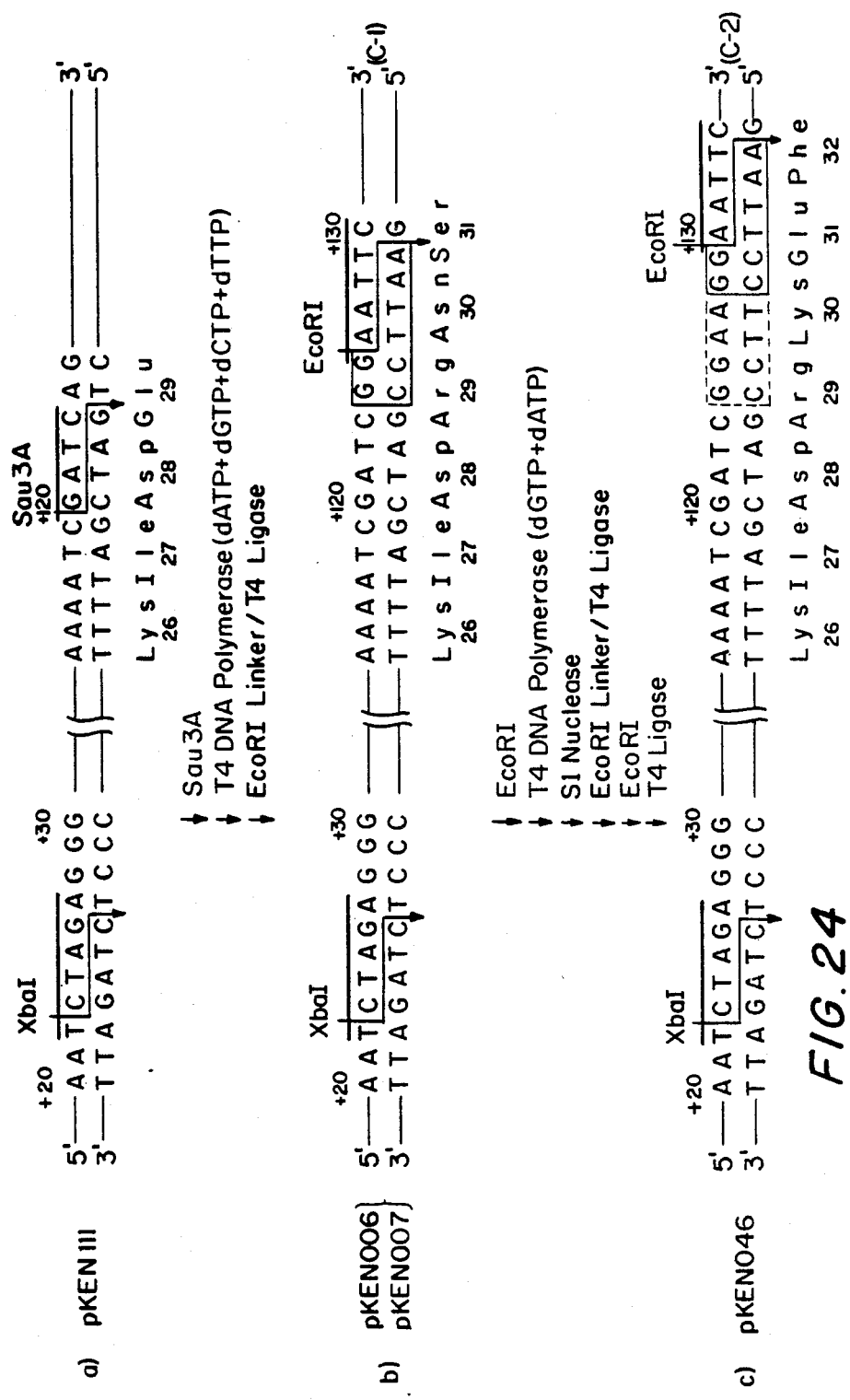
Figure 25:
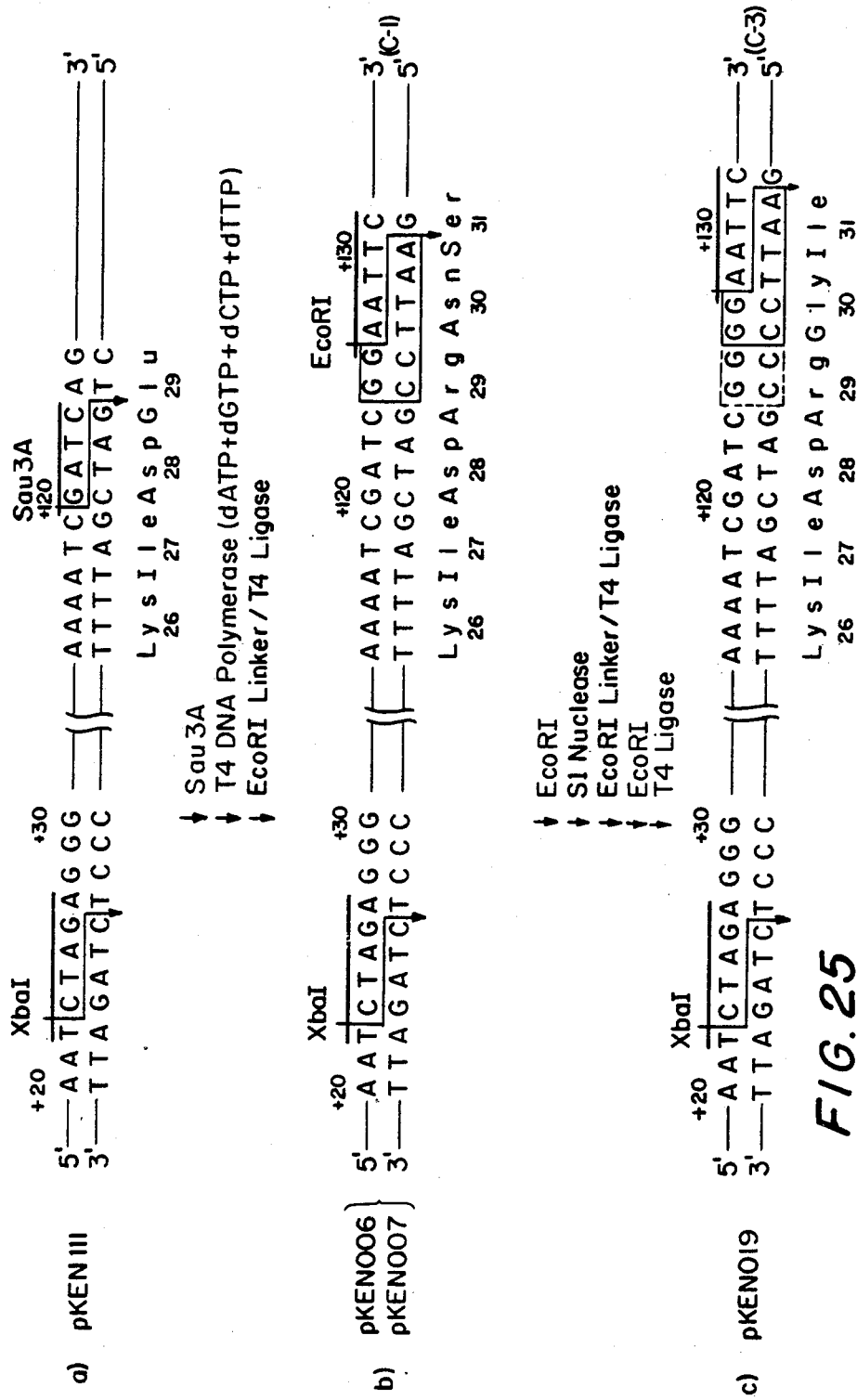

The reading frame at the C insertion site in pKEN007 was then modified to yield plasmids corresponding to the C-2 and C-3 reading frames, according to the methods previously described for changing the A-1 reading frame into the A-2 or A-3 reading frames, respectively. These procedures are illustrated schematically at 148 and 149 in FIG. 23, and the corresponding modifications of the DNA sequence around the Eco RI cleavage site are shown in FIGS. 24 and 25. It will be understood that the same procedures used to derive plasmids pKEN024 (A-2) and pKEN036 (A-3) from plasmid pKEN030 (A-1), described hereinabove in connection with FIGS. 13 and 14, can be used to derive plasmids pKEN046 (C-2) and pKEN019 (C-3) from plasmid pKEN007 (C-1).

3. Construction of Plasmids pKEN042, pKEN043 and pKEN044

Figure 26:
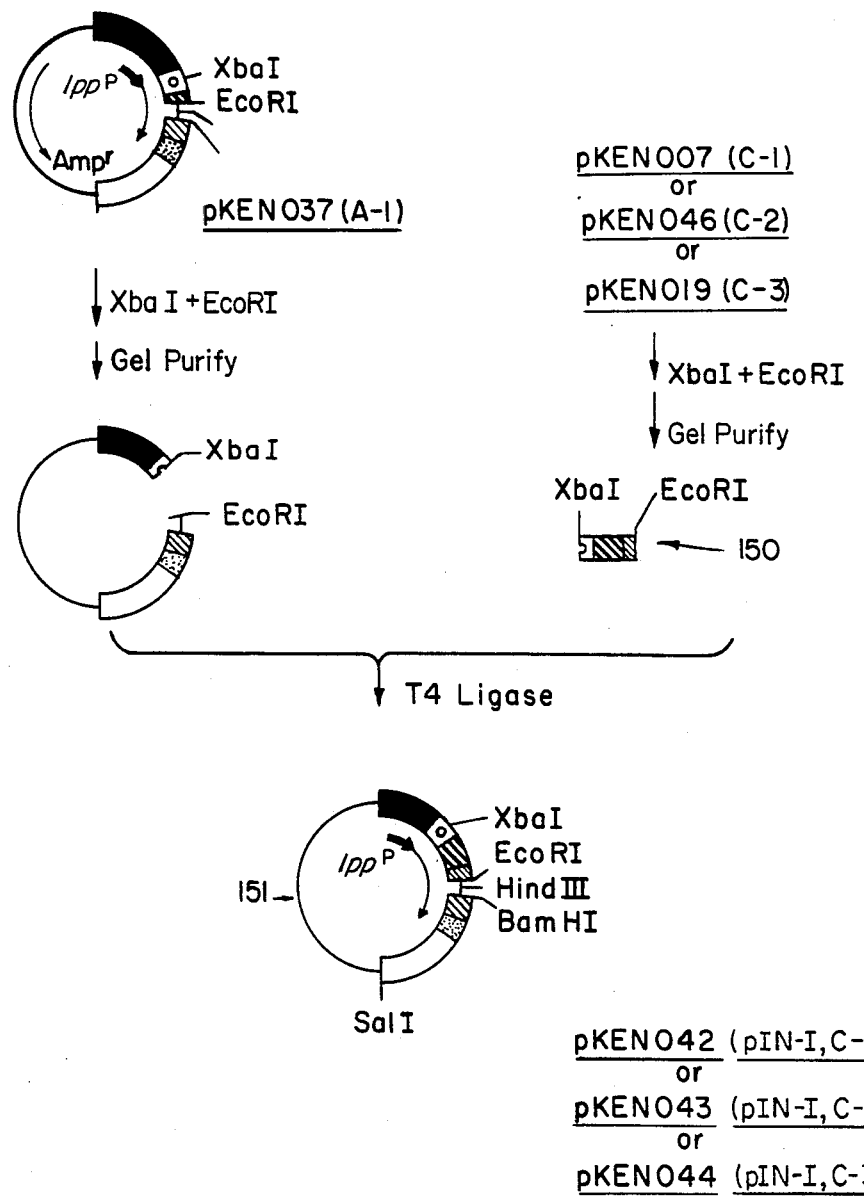

The last step in the construction of the constitutive C site expression plasmids was to substitute each of the three different Xba I-Eco RI C site fragments of pKEN007, pKEN046 and pKEN019 for the Xba I-Eco RI A site fragment of pKEN037, as illustrated in FIG. 26. This was done so that the C site plasmids would contain the same sequence of Eco RI, Hind III and Bam HI restriction enzyme recognition sequences at the exogenous DNA insertion site as contained in the A site and B site plasmids. As shown schematically at 150 in FIG. 26, each of the three C site fragments derived from pKEN007, pKEN046 and pKEN019 contains the DNA sequence including the signal peptide obtained from the Sau 3A fragment of the E. coli lpp gene.

In order to accomplish this result, the same procedure was used to obtain the larger Xba I-Eco RI fragment of pKEN037 as was described hereinabove in connection with FIG. 15. One microliter aliquots of the aqueous pKEN037 DNA fragment mixture were each combined with a different Xba I-Eco RI smaller fragment (about 0.1 micrograms of each) previously obtained from pKEN007, pKEN046 and pKEN019, respectively, by double digestion with Xba I and Eco RI restriction enzymes followed by gel purification. Each DNA mixture was treated with 0.2 units of T4 DNA ligase in 20 microliters of ligase buffer containing 0.4 mM ATP at 12.5° C. for 16 hours. Ten microliters of each of the ligated mixtures were used to transform E. coli strain JA221, NRRL B-15014. Among the ampicillin-resistant transformants, plasmid DNAs having the C-1, C-2 and C-3 reading frames were purified, and these were designated pKEN042, pKEN043 and pKEN044, respectively, each having the structure shown at 151 in FIG. 26.

D. Construction of Inducible Expression (pIN-II) Plasmids

Figure 27:
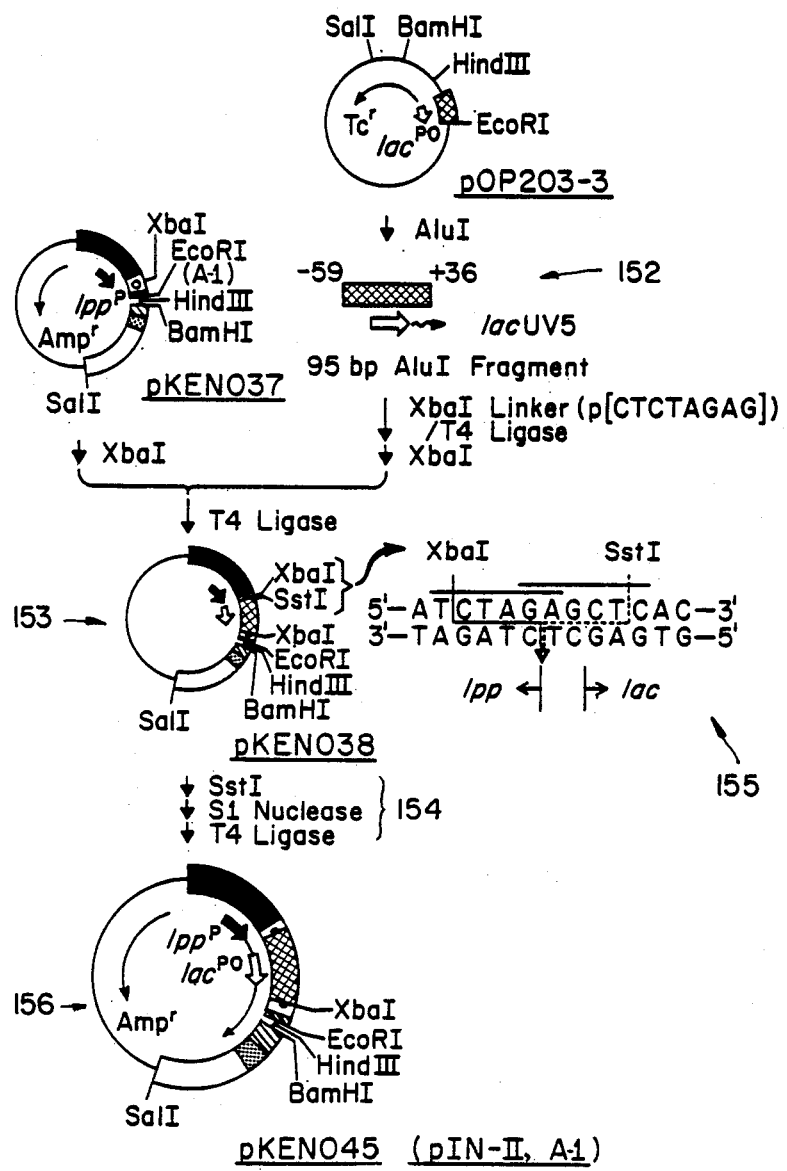

FIG. 27 schematically depicts the manner in which an inducible plasmid cloning vehicle incorporating the A insertion site in the A-1 reading frame (and corresponding to the constitutive plasmid pKEN037) was constructed. The lac UV5 promoter-operator was derived from plasmid pOP203-3 (obtained from Dr. F. Fuller, Dept. of Biochemistry and Molecular Biology, Harvard University). The lac UV5 promoter-operator is obtainable from E. coli 4288 recA/pKM006, NRRL B-15236, which is available to the public from the permanent collection of the Northern Regional Research Laboratory, U.S. Department of Agriculture, Peoria, Ill., U.S.A. The lac UV5 promoter-operator is carried on a 95 bp Xba I fragment of plasmid pKM006. The plasmid can be obtained from NRRL B-15236 by conventional means, and the 95 bp Xba I fragment can thereafter be isolated using known techniques.

Figure 29:
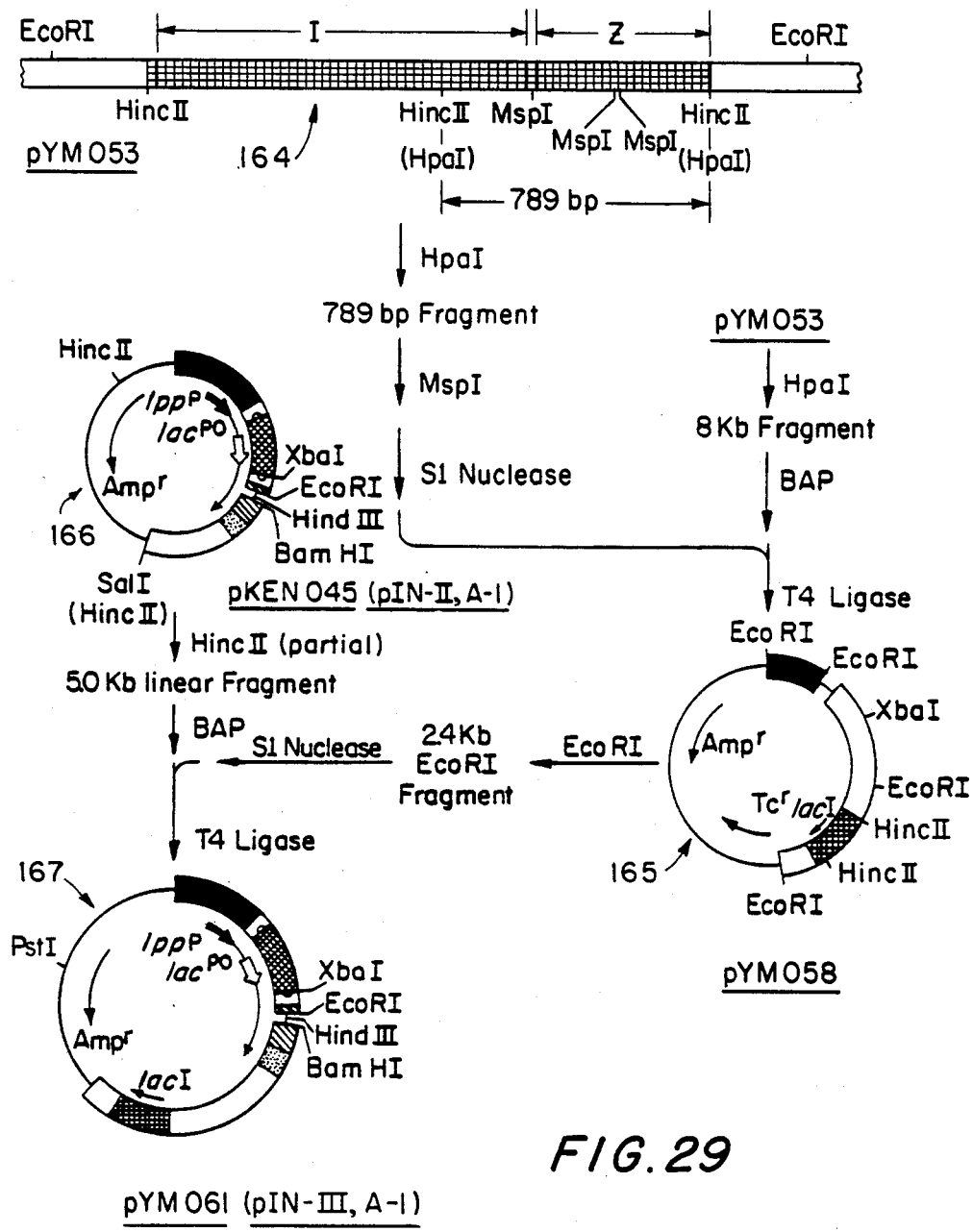
Figure 30A:
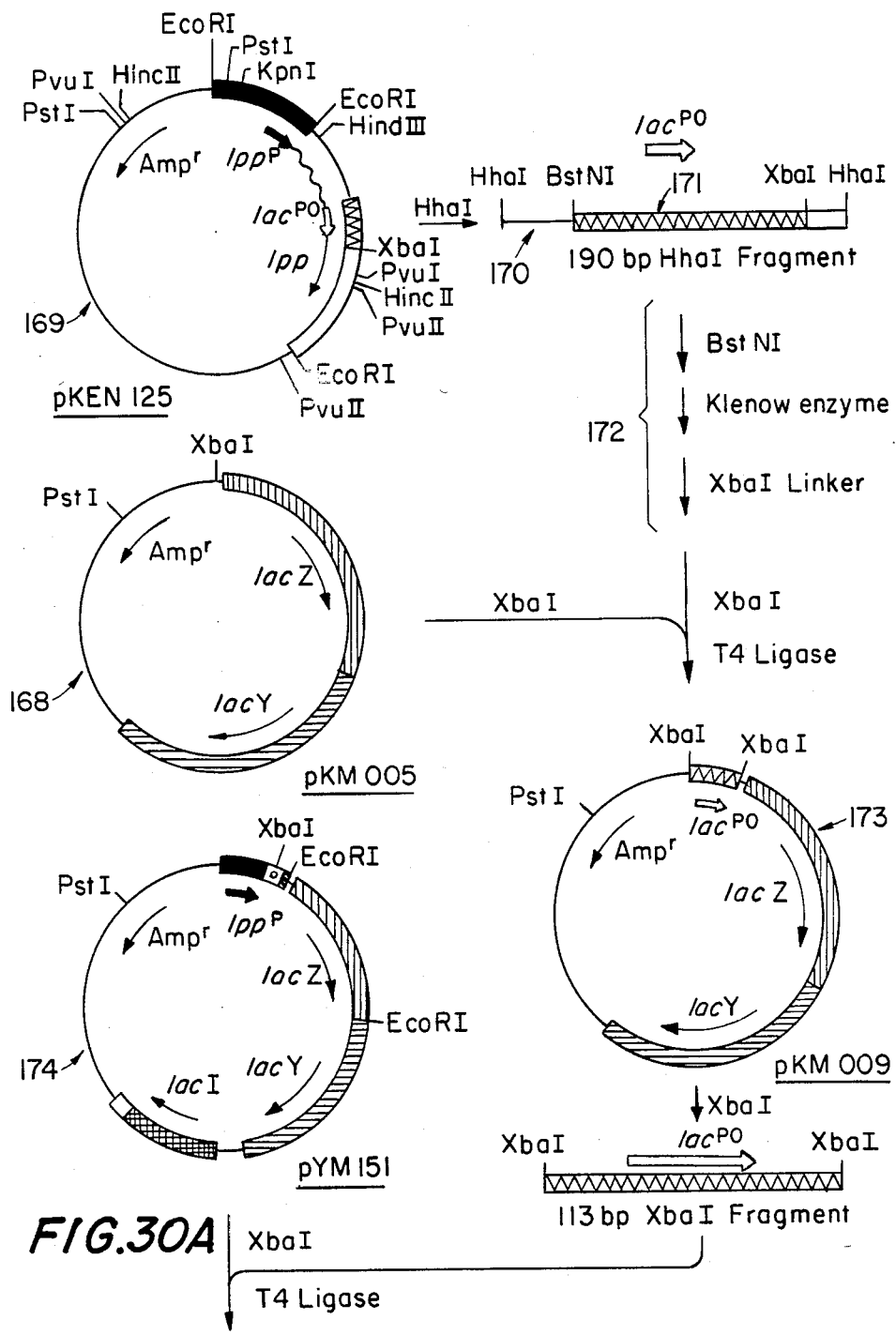
FIGS. 30A and 30B together comprise a schematic illustration of the experimental method actually used to construct one of the plasmids of the present invention.
Figure 30B:
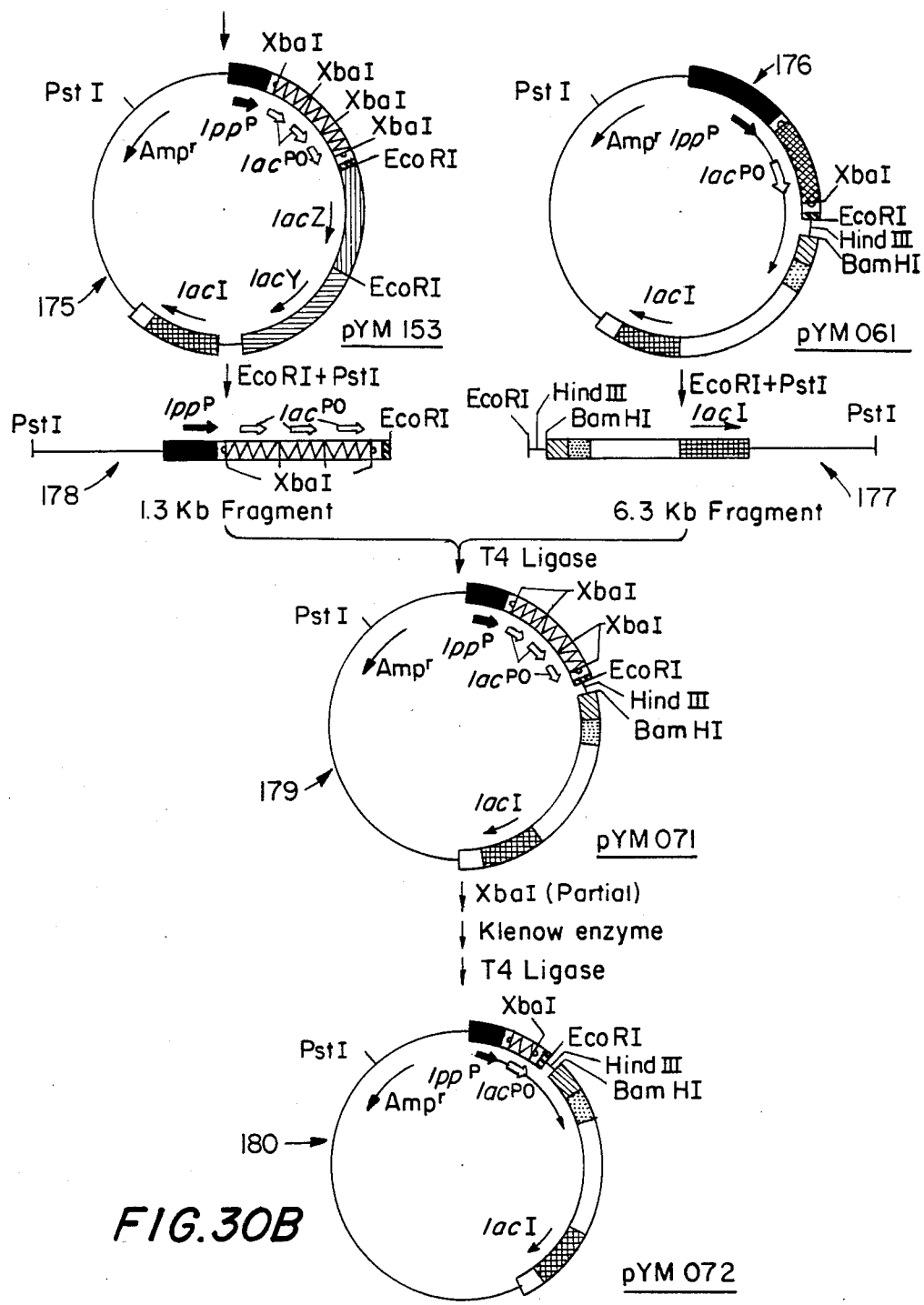
Figure 31A:
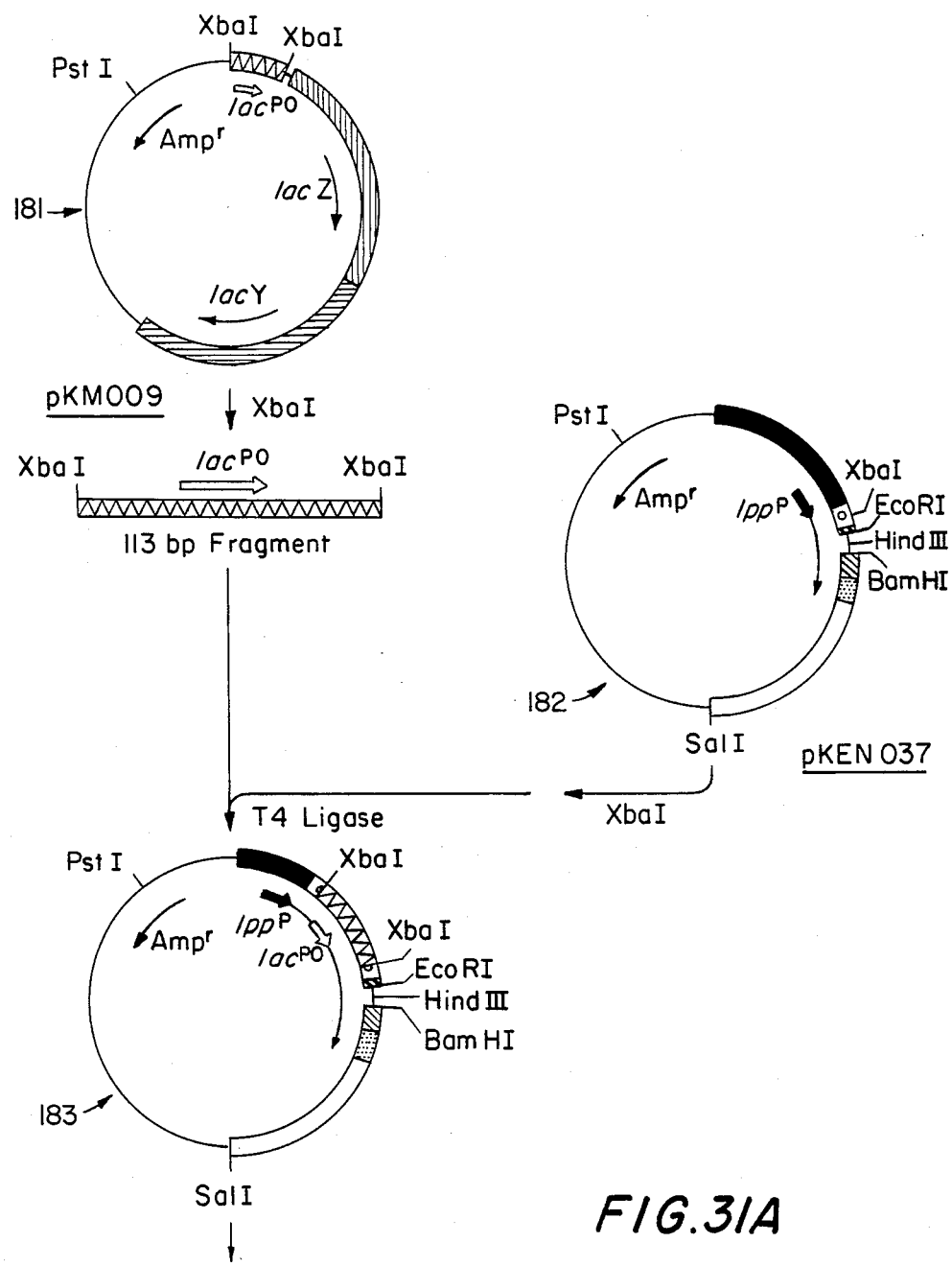
FIGS. 31A and 31B together comprise a schematic illustration of the preferred method of modification of one of the plasmids resulting from the earlier research efforts to obtain the corresponding plasmid of the present invention.
Figure 31B:
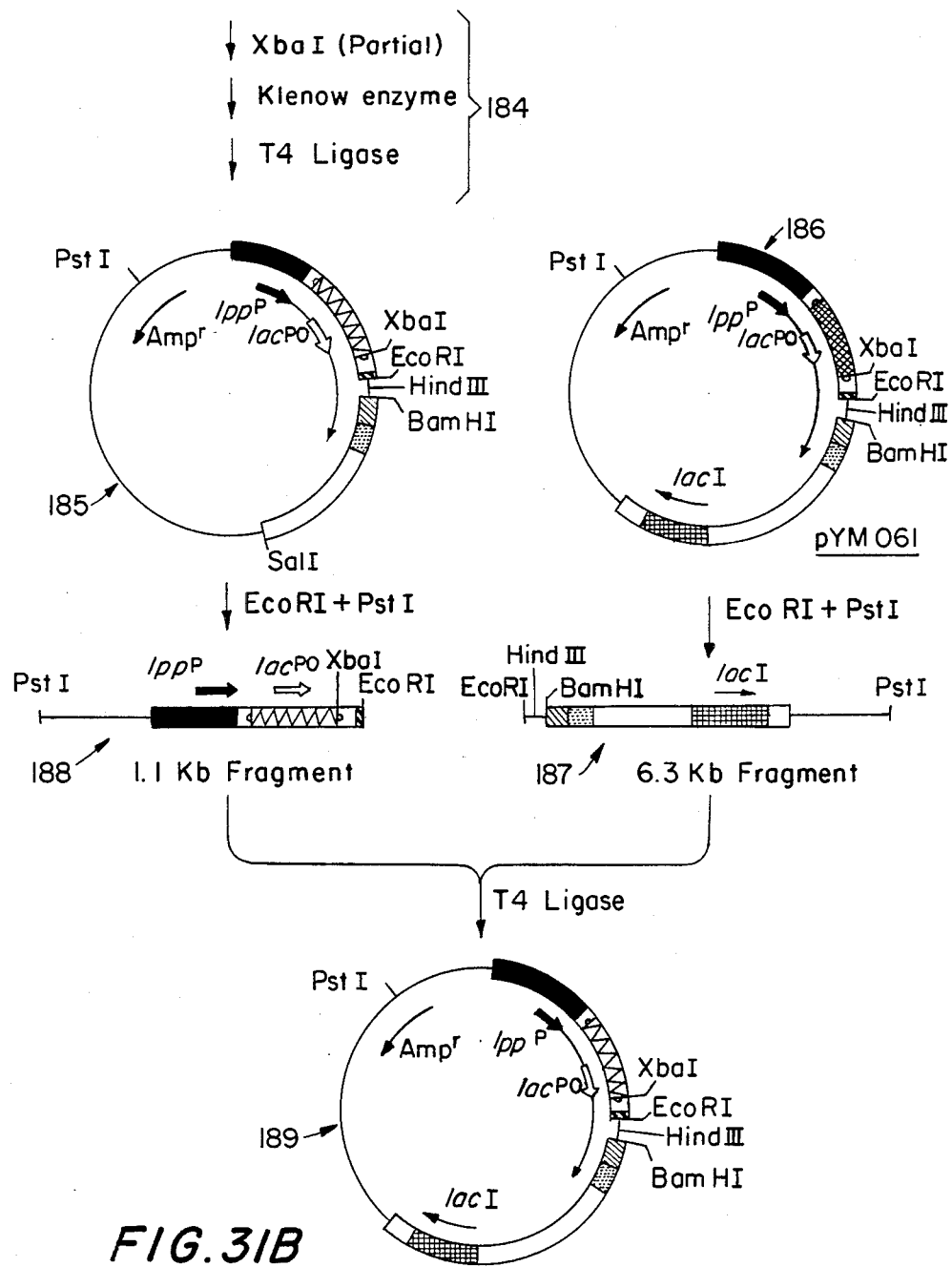

The lac UV5 promoter-operator was inserted at the Xba I cleavage site of pKEN037 (within the 5'-untranslated region of the lpp gene) according to the following procedure: 200 micrograms of pOP203-3 plasmid DNA were digested to completion with 200 units of Alu I restriction enzyme in 400 microliters of Hind III buffer, and a 95 bp Alu I fragment carrying lac UV5 promoter and operator region (illustrated schematically by the diagonally cross-hatched segment at 152 in FIG. 27 and similarly in FIGS. 29, 30B and 31B) was purified by polyacrylamide gel electrophoresis. One microgram of the 95 bp Alu I fragment was mixed with 400 pmoles of phosphorylated Xba I linker (5'CTCTAGAG3'; obtained from Colaborative Research and phosphorylated in the same manner as described hereinabove), and blunt-end ligated with 5 units of T4 DNA ligase in 20 microliters of ligase buffer containing 0.6 mM ATP at 12.5° C. for 16 hours. The ligated mixture was diluted to 300 microliters with Bam HI buffer and heated at 60° C. for 10 minutes. The mixture was then treated with 100 units of Xba I restriction enzyme at 37° C. for one hour to create Xba I cohesive termini. The mixture was extracted with phenol, ethanol precipitated and lyophilized. The DNA fragments were then dissolved in 10 microliters of water, and 0.3 micrograms of the lac fragment thus obtained were mixed with 0.5 micrograms of pKEN037 plasmid DNA, which had previously been digested with Xba I restriction enzyme. The mixture was treated with 0.4 units of T4 DNA ligase in 20 microliters of ligase buffer containing 0.4 mM ATP at 12.5° C. for 16 hours to anneal the Xba I cohesive termini, thereby re-circularizing the plasmid. Ten microliters of the ligated mixture were used to transform E. coli JA221/F'lacIq, NRRL B-15015, which was constructed by transferring the F' factor from χ90/F'lacIq lac+ pro+ (obtained from Dr. J. Beckwith, Dept. of Biochemistry and Molecular Biology, Harvard University) into E. coli strain JA221, NRRL B-15014. E. coli strain JA221/F'lacIq is available to the public from the permanent collection of the Northern Regional Research Laboratory, U.S. Department of Agriculture, Peoria, Ill., U.S.A. Upon restriction enzyme analysis of the plasmid DNAs isolated from ampicillin-resistant transformants by the rapid alkaline denaturation method, one of them was found to contain one copy of the 95 bp Alu I fragment inserted at the Xba I site of pKEN037 in the correct orientation, as shown at 153 in FIG. 27, and this plasmid was designated pKEN038.

In order to simplify the construction of inducible plasmids containing the B and C insertion sites, it was first necessary to remove one of the two Xba I cleavage sites in pKEN038 surrounding the lac promoter-operator fragment. The Xba I cleavage site located upstream of the lac promoter-operator fragment was eliminated as shown schematically at 154 in FIG. 27. This was carried out utilizing the fact that attachment of the Xba I linker to the 95 bp lac promoter-operator fragment, as described in the preceding paragraph, resulted in the creation of a new Sst I cleavage site only at the upstream end of the lac promoter, but not at the downstream end. As shown at 155 in FIG. 27, the recognition sequence of the Sst I restriction enzyme overlaps with that of the Xba I enzyme. Thus, the deletion of the 4-base "sticky end" of the Sst I cleavage site using S1 nuclease should result in the deletion of part of the Xba I recognition sequence as well, effectively eliminating the Xba I cleavage site.

In order to accomplish this result, five micrograms of pKEN038 plasmid DNA were digested with 10 units of Sst I restriction endonuclease in 50 microliters of Bam HI buffer, and treated with 500 units of S1 nuclease in 200 microliters of S1 buffer at 20° C. for one hour. Blunt ends were joined by treatment of 0.5 micrograms of the S1-treated DNA with 5 units of T4 DNA ligase in 10 microliters of ligase buffer containing 0.6 mM ATP at 12.5° C. for 16 hours. Five microliters of the ligated mixture were used to transform E. coli strain JA221/F-'lacIq, NRRL B-15015. A plasmid having the structure shown schematically at 156 in FIG. 27 was isolated after restriction enzyme analysis of plasmid DNAs obtained from ampicillin-resistant transformants by the rapid alkaline denaturation method, and that plasmid was designated pKEN045 (pIN-II, A-1).

There are several methods available with which to construct pIN-II plasmids corresponding to the A-2 and A-3 reading frames. Assuming the availability of the pIN-I A-2 and A-3 plasmids, one method would involve inserting the lac promoter-operator fragment into plasmids pKEN039 and pKEN040 in the same manner as shown in FIG. 27 and described hereinabove in connection with plasmid pKEN037. An alternative and preferable method merely requires transferring the smaller Xba I-Eco RI fragments of pKEN039 and pKEN040 into the Xba I-Eco RI site of pKEN045, in a manner analogous to that described hereinabove in connection with FIG. 15, to yield plasmids pKEN049 (pIN-II, A-2) and pKEN050 (pIN-II, A-3).

On the other hand, assuming that the corresponding constitutive plasmids are not already constructed, inducible plasmids pKEN049 (A-2) and pKEN050 (A-3) can be derived directly from plasmid pKEN045 (A-1). Specifically, the DNA sequence in the vicinity of the Eco RI cleavage site of pKEN045 can itself be modified according to the scheme shown in FIG. 13, lines b and c, or the scheme illustrated in FIG. 14, lines b and c, to yield directly the structure of plasmids pKEN049 (A-2) or pKEN050 (A-3), respectively. This is the most preferred method of constructing these plasmids, since it does not require as a condition precedent the construction of the corresponding constitutive plasmids.

There are also several options available in constructing pIN-II plasmids incorporating the B and C insertion sites. Assuming again that the corresponding pIN-I plasmids have already been constructed, each could be modified to insert the lac promoter-operator fragment, according to the procedure of FIG. 27, or more preferably, the smaller Xba I-Eco RI fragment of pKEN045 (pIN-II, A-1) could be replaced successively with the smaller Xba I-Eco RI fragments from each of the constitutive B site and C site plasmids, yielding, in either case, pIN-II plasmids according to Table I.

TABLE I

| Insertion Site | Reading Frame | pIN-I Plasmids | pIN-II Plasmids |
|---|---|---|---|
| B | 1 | pKENO41 | pKENO51 |
|   | 2 | pKENO47 | pKENO52 |
|   | 3 | pKENO48 | pKENO53 |
| C | 1 | pKENO42 | pKENO54 |
|   | 2 | pKENO43 | pKENO55 |
|   | 3 | pKENO44 | pKENO56 |

Most preferably, however, the pIN-II expression plasmids are constructed without first making the corresponding pIN-I plasmids. In the case of the B insertion site, plasmid pKEN051 (pIN-II, B-1) can be derived from plasmid pKEN221 by first digesting pKEN221 plasmid DNA with Fnu4H-I restriction enzyme and then attaching Eco RI cohesive termini to the ends of the resulting fragment, according to the procedure described hereinabove and illustrated schematically at 138 in FIG. 17. The Eco RI fragment thus obtained can then be digested by Xba I restriction enzyme, splitting the fragment in two at the Xba I cleavage site located within the 5'-untranslated region. By purifying the smaller Xba I-Eco RI fragment thus obtained, and substituting it for the smaller Xba I-Eco RI fragment of pKEN045 (pIN-II, A-1), the B-1 inducible cloning vehicle can be obtained. The resulting plasmid, pKEN051 (pIN-II, B-1), can then be further modified according to the scheme illustrated schematically at 141 in FIG. 18 and in FIG. 19, or according to the scheme shown schematically at 142 in FIG. 18 and in FIG. 20, to yield the pIN-II plasmids corresponding to the B-2 and B-3 reading frames, pKEN052 and pKEN053, respectively.

An analogous course can be followed to obtain the pIN-II C site plasmids directly, without first constructing the corresponding pIN-I plasmids. Specifically, after digestion of pKEN111 plasmid DNA with Sau 3A restriction enzyme and attachment of Eco RI cohesive termini to the ends of the resulting fragment (according to the procedure described hereinabove and illustrated at 145 in FIG. 22), the Eco RI fragment thus obtained can then be digested with Xba I restriction enzyme, splitting the fragment in two at the Xba I cleavage site (located within the 5'-untranslated region). The Xba I-Eco RI fragment carrying the signal peptide region can then be inserted into the Xba I-Eco site of pKEN045, resulting in the plasmid pKEN054 (pIN-II, C-1). Further modification of the pKEN054 DNA according to the procedure shown schematically at 148 in FIG. 23 and in FIG. 24, or according to the procedure illustrated schematically at 149 in FIG. 23 and in FIG. 25, yields the pIN-II plasmids corresponding to the C-2 and C-3 reading frames, pKEN055 and pKEN056, respectively.

E. Construction of Auto-Regulated Inducible Expression (pIN-III) Plasmids

Figure 28:
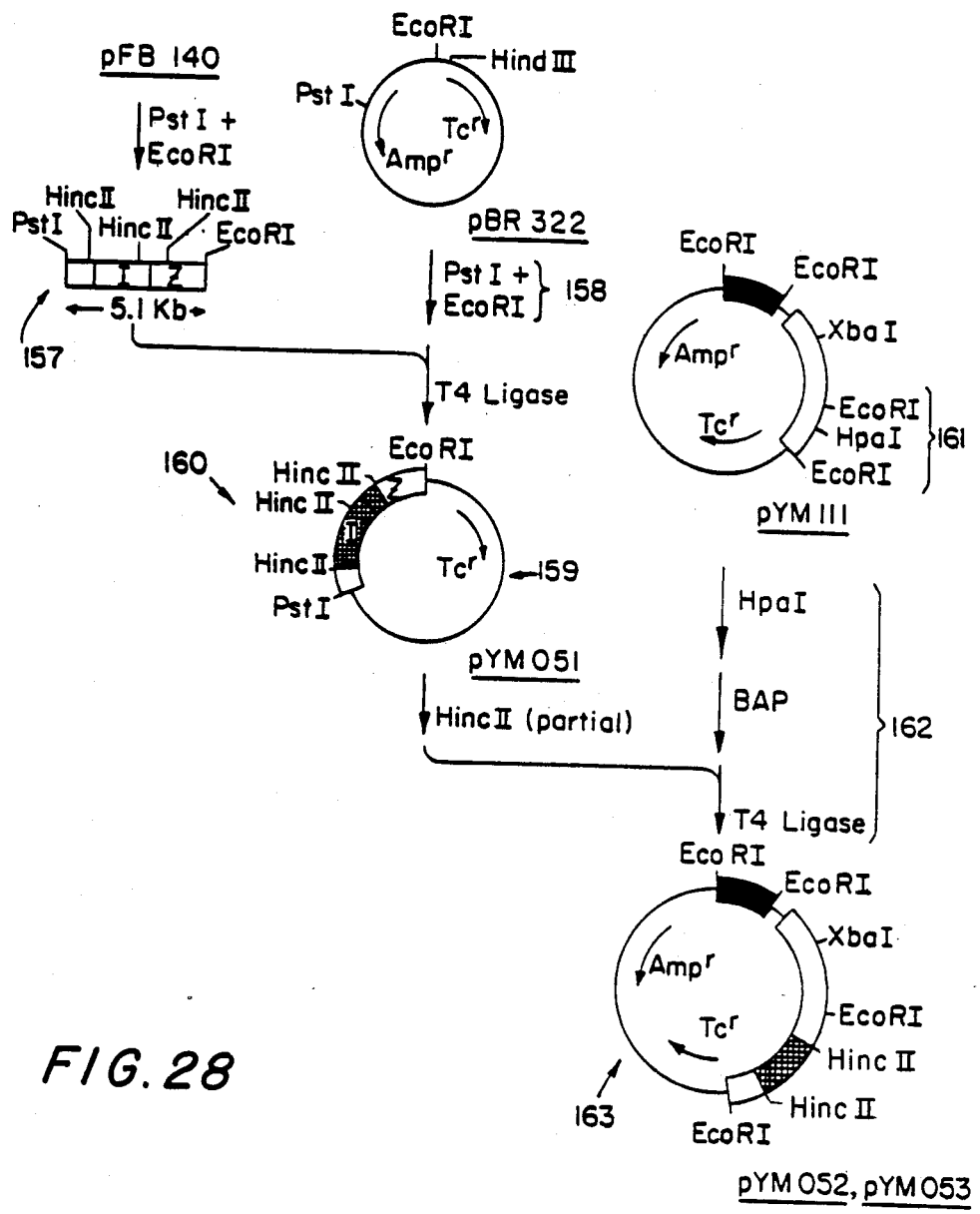

FIGS. 28 and 29 schematically illustrate the manner in which the lacI gene was added to the inducible A-1 plasmid cloning vehicle of the pIN-II series, yielding the corresponding auto-regulated inducible expression plasmid of the pIN-III series. The specific steps in this procedure are described in detail hereinbelow.

1. Construction of Plasmid pYM051

The first step in the construction of the A-1 expression plasmid of the pIN-III series was to clone the lacI gene into pBR322. In order to accomplish this result, a 5.1 Kb DNA fragment containing the lacI gene was first derived from plasmid pFB140 (obtained from Monica Riley of the Department of Biochemistry, State University of New York at Stony Brook) as follows: 15 micrograms of pFB140 plasmid DNA were digested with 80 units Eco RI restriction enzyme in 200 microliters of Eco RI buffer at 37° C. for 2 hours. The reaction mixture was extracted with phenol and the DNA fragments were precipitated with 2.5 volumes of ethanol and dried under vacuum. The DNAs were then digested to completion with 12 units of Pst I restriction endonuclease in 300 microliters of a reaction mixture containing 6 mM Tris:HCl (pH 7.5), 6 mM $MgCl_2$, 50 mM NaCl, 6 mM $\beta$-mercaptoethanol and 100 micrograms/ml BSA (this reaction mixture will hereinafter be referred to as a "Pst I buffer") at 37° C. for 2 hours. A 5.1 Kb Pst I-Eco RI fragment carrying the lacI gene (illustrated schematically at 157 in FIG. 28) was purified by agarose gel electrophoresis: the DNA fragments in the agarose gel were stained with ethidium bromide (one microgram/ml), and the band corresponding to the 5.1 Kb fragment was cut out. The DNA fragments in this band were eluted from the gel after freezing. Ethidium bromide was removed from the DNA fragments by phenol extraction, and the DNAs were recovered by ethanol precipitation.

In order to clone the 5.1 Kb Pst I-Eco RI fragment containing the lacI gene into pBR322, the smaller DNA fragment lying between the Pst I and Eco RI cleavage sites of pBR322 was first deleted, as shown schematically at 158 in FIG. 28, using the following procedure:

10 micrograms of pBR322 DNA were digested with 2 units of Pst I restriction enzyme in 100 microliters of Pst I buffer at 37° C. for 3 hours. After phenol extraction and ethanol precipitation, the DNAs were dried under vacuum, and then digested with 80 units of Eco RI restriction enzyme in a total volume of 200 microliters of Eco RI buffer at 37° C. for 2 hours. The larger Pst I-Eco RI fragments, consisting of approximately 3.7 Kb, were then purified by agarose gel electrophoresis.

The purified fragments (0.07 micrograms) were then mixed with 0.1 micrograms of the previously-obtained 5.1 Kb pFB140 fragments, and the Pst I and Eco RI cohesive termini were ligated by treating with 20 units of T4 DNA ligase (obtained from New England Biolabs) in 25 microliters of ligase buffer containing 0.48 mM ATP at 12.5° C. for 16 hours. Fifteen microliters of the ligated mixture were used to transform *E. coli* strain W620 recA, NRRL B-15024 (F−, thi-1, pyrD36, gltA6, galK30, strA129λ−, supE44). This strain is available to the public from the permanent collection of the Northern Regional Research Laboratory, U.S. Department of Agriculture, Peoria, Ill., U.S.A., and was derived from *E. coli* strain W620, obtained from the Department of Human Genetics, Yale University, School of Medicine. One of the plasmid DNAs purified from tetracycline-resistant transformants had the structure shown at 159 in FIG. 28. This plasmid was designated pYM051, and is obtainable from *E. coli* W620 recA/pYM051, NRRL B-15025, which is available to the public from the permanent collection of the Northern Regional Research Laboratory, U.S. Department of Agriculture, Peoria, Ill., U.S.A. The plasmid can be obtained from NRRL B-15025 by conventional means.

2. Construction of Plasmids pYM052 and pYM053

Plasmid pYM051 carries a 5.1 Kb Pst I-Eco RI DNA fragment containing not only the lacI gene, but also a substantial portion of the lacZ gene. As shown at 160 in FIG. 28, this fragment contains three Hinc II cleavage sites in the vicinity of the lacI gene, two of which surround or "bracket" the lacI gene, and one of which falls within the lacI gene itself. In order to shorten this 5.1 Kb DNA fragment and at the same time retain the lacI gene intact for later use, the following procedure was used: 5 micrograms of pYM051 plasmid DNA were partially digested with 0.32 units of Hinc II restriction enzyme in 75 microliters of Hind III buffer at 37° C. for 1 hour. After phenol extraction and ethanol precipitation, the DNAs were dried under vacuum. This procedure yielded DNA fragments of varying of lengths, one of which (1.7 Kb in length—shown schematically by the vertical and horizontal cross-hatching at 160 in FIG. 28 and similarly in FIGS. 29, 30A, 30B and 31B) carries an intact lacI gene.

In order to provide a vehicle to carry the shortened DNA fragment bearing the lacI gene, a plasmid designated pYM111 was constructed. This plasmid is obtainable from *E. coli* JA221/F'lacIq/pYM111, NRRL B-15038, which is available to the public from the permanent collection of the Northern Regional Research Laboratory, U.S. Department of Agriculture, Peoria, Ill., U.S.A. The plasmid can be obtained from NRRL B-15038 by conventional means.

As shown schematically at 161 in FIG. 28, pYM111 includes a Hpa I cleavage site surrounded in relatively close proximity by two Eco RI cleavage sites. This plasmid is an acceptable recipient for the lacI gene fragment because it is a member of the class of plasmids having the following characteristics: (1) it contains a unique restriction enzyme cleavage site (i.e., a site occurring only once within the plasmid) which preferably yields blunt end termini, such as Hpa I, Hinc II or Pvu II; (2) it is derived from pBR322, and the unique cleavage site is not located within the DNA sequence responsible for the replication of the plasmid itself; (3) it also contains two cleavage sites which surround the unique cleavage site and are located within approximately 400–700 base pairs of the unique cleavage site, the two surrounding cleavage sites preferably being recognizable by the same readily-available restriction enzyme, such as Eco RI, Hind III, Bam HI or Pst I, provided that neither of the two surrounding cleavage sites is also repeated within the lacI gene.

Plasmid pYM111 is suitable because it contains only one Hpa I cleavage site surrounded within 400–700 base pairs by two Eco RI cleavage sites, and because the lacI gene does not itself contain any Eco RI cleavage sites. It is to be understood, however, that any suitable plasmid having the foregoing characteristics can be used to receive the lacI gene fragment and to serve as a source of that fragment in subsequent steps of the procedure.

The DNA fragment carrying the lacI gene was inserted in plasmid pYM111, as shown schematically at 162 in FIG. 28, according to the following procedure: four micrograms of pYM111 plasmid DNA were digested with 4 units of Hpa I restriction endonuclease in a total volume of 50 microliters of Hpa I buffer at 37° C. for 1 hour. Phenol extraction was performed, after which the DNAs were recovered by ethanol precipitation and dried under vacuum. To prevent self-ligation of the Hpa I-treated DNA fragments, the dried DNAs were treated with 0.15 units of BAP in a total volume of 100 microliters of a reaction mixture comprising 10 mM Tris:HCl (pH 8.0) and 0.1 mM EDTA (this reaction mixture will hereinafter be referred to as a "BAP buffer") at 37° C. for 45 minutes. Phenol extraction was performed three times to remove the BAP completely, after which the DNAs were recovered by ethanol precipitation and then dried under vacuum.

In order to insert the 1.7 Kb DNA fragment carrying the intact lacI gene into pYM111, 0.1 micrograms of the Hpa I-treated pYM111 plasmid DNA were mixed with 0.275 micrograms of the DNA fragments obtained from the Hinc II partial digestion of pYM051, and the DNAs were ligated with 320 units of T4 DNA ligase (obtained from New England Biolabs) in ligase buffer (total volume 20 microliters) containing 0.6 mM ATP at 12.5 for 16 hours. Half of the ligation mixture was used to transform *E. coli* strain W620 recA, NRRL B-15024, and transformants were placed on the surface of an L-plate containing 50 micrograms/ml of ampicillin and 40 micrograms/ml of 5-bromo-4-chloro-3-indolyl-β-D-galactoside (hereinafter referred to as "X-gal"). The transformants yielding white colonies were selected, indicating insertion of the 1.7 Kb Hinc II fragment carrying the intact lacI gene into plasmid pYM111. Since this transformation results in plasmids carrying the lacI gene in two different orientations, the resulting plasmids were designated pYM052 and pYM053. The structure of both of these plasmids is depicted at 163 in FIG. 28.

3. Construction of Plasmid pYM058

In order to limit still further the size of the expression plasmid, and also to eliminate any possible inhibitory effect on lacI gene expression resulting from the small portion of the lacZ gene still remaining in the plasmid, the lacZ gene fragment was deleted while preserving the lacI gene intact. FIG. 29 depicts schematically the strategy used to remove this fragment from plasmid pYM053.

The illustration at 164 in FIG. 29 is a partial restriction enzyme cleavage map of the region between the two Eco RI cleavage sites of plasmid pYM053, containing the lacI gene. This region includes the three Hinc II cleavage sites discussed hereinabove in connection with FIG. 28 and shown at 157 and at 160 in FIG. 28. As shown in FIG. 29, two of these Hinc II cleavage sites are also recognized by the Hpa I restriction endonuclease. Moreover, the greater detail of FIG. 29 reveals that there are three Msp I cleavage sites in this region, two of which are located within the lacZ gene fragment, and one of which is located within the DNA sequence that separates the 3' end of the lacI gene from the 5' end of the lacZ gene fragment.

The foregoing arrangement permits easy isolation of the 789 bp fragment lying between the two Hpa I cleavage sites. This fragment can be further subdivided to obtain a mixture of Msp I fragments, one of which contains the 3' region of the lacI gene, but no portion of the lacZ gene. The latter fragment can then be inserted in the proper orientation to reconstruct an intact lacI gene.

In order to accomplish this result, 100 micrograms of pYM053 plasmid DNA were digested with 60 units of Hpa I restriction enzyme in 800 microliters of Hpa I buffer at 37° C. for 2 hours. A 789 bp fragment was purified by 5% polyacrylamide gel electrophoresis: the DNA fragments in the polyacrylamide gel were stained with ethidium bromide (one microgram/ml), and the band corresponding to the 789 bp fragment was cut out. The DNA fragments in this band were eluted from the gel using electrophoresis. Ethidium bromide was removed from the DNA fragments by phenol extraction, and the DNAs were recovered by ethanol precipitation.

The purified 789 bp DNA fragments (1.1 micrograms) were then digested with 12 units of Msp I restriction enzyme in 75 microliters of Hpa I buffer at 37° C. for one hour. Phenol extraction was performed, after which the DNAs were recovered by ethanol precipitation and dried under vacuum. The DNA fragments were then treated with 2,000 units of S1 nuclease in a total volume of 150 microliters of S1 buffer at 20° C. for 1 hour. The reaction was terminated by adding 15 microliters of 500 mM Tris:HCl (pH 8.0) and 15 microliters of 250 mM EDTA, following which phenol extraction was performed. To remove phenol and zinc ions, the mixture was extracted with ether and dialyzed against 0.01×SSC at 4° C. for 1.5 hours twice, and the DNAs were then recovered by ethanol precipitation.

Ten micrograms of pYM053 plasmid DNA were separately digested with 12 units of Hpa I restriction enzyme in 100 microliters of Hpa I buffer at 37° C. for 1 hour. An 8 Kb fragment was purified by 0.7% agarose gel electrophoresis, and the DNAs (1.1 micrograms) were then treated with 0.12 units of BAP in 75 microliters of BAP buffer at 37° C. for one hour to prevent self-ligation of the Hpa I blunt ends. Phenol extraction was performed three times to remove the BAP completely, and the DNAs were recovered by ethanol precipitation and then dried under vacuum.

The 8 Kb Hpa I fragments (0.4 micrograms) derived from pYM053 were then mixed with 0.05 micrograms of the DNA fragments obtained from the Msp I digestion of the 789 bp fragment derived from pYM053, and the DNAs were ligated with 400 units of T4 DNA ligase (obtained from New England Biolabs) in ligase buffer (total volume 15 microliters) containing 0.8 mM ATP at 12.5° C. for 16 hours. Ten microliters of the ligation mixture were used to transform E. coli strain W620 recA, NRRL B-15024, and the transformants were placed on the surface of an L-plate containing 50 micrograms/ml of ampicillin and 40 micrograms/ml of X-gal. The ampicillin-resistant transformants yielding white colonies were selected, indicating that an intact lacI gene had been reconstructed. One of the plasmid DNAs purified from the transformants selected had the structure shown at 165 in FIG. 29, and this plasmid was designated pYM058.

4. Construction of Plasmid pYM061 and Other Auto-Regulated Expression Plasmids

The final step in the construction of the first auto-regulated inducible expression plasmid of the pIN-III series was to insert the lacI gene into pKEN045 (pIN-II, A-1). In order to accomplish this result, the following procedure was used: 30 micrograms of pYM058 plasmid DNA were digested with 100 units of Eco RI restriction enzyme in 250 microliters of Eco RI buffer at 37° C. for 1.5 hours. A 2.4 Kb Eco RI fragment was purified by agarose gel electrophoresis in the same manner as described hereinabove. The DNA fragments (2.0 micrograms) were then treated with 600 units of S1 nuclease in a total volume of 150 microliters of S1 buffer at 20° C. for 1 hour. The reaction was terminated by adding 15 microliters of 500 mM Tris:HCl (pH 8.0) and 15 microliters of 250 mM EDTA, following which phenol extraction was performed. To remove phenol and zinc ions, the mixture was extracted with ether and dialyzed against 0.01×SSC at 4° C. for 1.5 hours twice, and the DNAs were then recovered by ethanol precipitation.

Ten micrograms of pKEN045 plasmid DNA were partially digested with one unit of Hinc II restriction enzyme in 75 microliters of Hind III buffer at 37° C. for 30 minutes. As shown schematically at 166 in FIG. 29, pKEN045 includes two Hinc II cleavage sites, one of which is also a Sal I cleavage site. Partial digestion with Hinc II restriction enzyme yielded a mixture of linear DNA fragments, the longest of which had been cleaved at only one of the Hinc II sites. These fragments (each about 5.0 Kb long) were isolated by 0.7% agarose gel electrophoresis in the same manner as described hereinabove.

The linearized DNAs (2.5 micrograms) were then treated with 0.15 units of BAP in 50 microliters of BAP buffer at 37° C. for one hour to prevent self-ligation of the Hinc II blunt ends. Phenol extraction was performed three times to remove the BAP completely. The DNAs were recovered by ethanol precipitation and then dried under vacuum.

The 2.4 Kb Eco RI fragments (0.15 micrograms) derived from pYM058 were then mixed with 0.3 micrograms of the 5.0 Kb pKEN045 fragments and treated with 400 units of T4 DNA ligase (obtained from New England Biolabs) in 15 microliters of ligase buffer containing 0.8 mM ATP at 12.5° C. for 16 hours. Ten microliters of the ligation mixture were used to transform E. coli strain W620 recA, NRRL B-15024, and ampicillin-resistant transformants were selected using X-gal as previously described. The white colonies confirmed insertion of the lacI gene at the Hinc II site downstream from the Ampr gene. This transformation results in plasmids carrying the lacI gene in two different orientations, the structure of one of which is illustrated schematically at 167 in FIG. 29. The plasmids having this structure were designated pYM061 (pIN-III, A-1).

There are several methods available with which to construct pIN-III plasmids corresponding to the A-2 and A-3 reading frames. Assuming the availability of the counterpart A-2 and A-3 plasmids of the pIN-I and pIN-II series, one method would involve inserting the lacI gene fragment into plasmids pKEN049 (pIN-II, A-2) and pKEN050 (pIN-II, A-3) in the same manner as shown in FIG. 29 and described hereinabove in connection with plasmid pKEN045. An alternative and preferable method merely requires substituting the smaller Xba I-Eco RI fragments of pKEN049 and pKEN050 (or pKEN039 (pIN-I, A-2) and pKEN040 (pIN-I, A-3)) for the smaller Xba I-Eco RI fragment of pYM061, in a manner analogous to that described hereinabove in connection with FIG. 15, to yield the A-2 and A-3 plasmids of the pIN-III series.

On the other hand, assuming that the corresponding constitutive (pIN-I) and inducible (pIN-II) plasmids are not already constructed, auto-regulated inducible A-2 and A-3 plasmids of the pIN-III series can be derived directly from plasmid pYM061 (A-1). Specifically, the DNA sequence in the vicinity of the Eco RI cleavage site of pYM061 can itself be modified according to the scheme shown in FIG. 13, lines b and c, or the scheme illustrated in FIG. 14, lines b and c, to yield directly the structure of the A-2 and A-3 plasmids, respectively, of pIN-III. This is the most preferred method of constructing these plasmids, since it does not require as a condition precedent the construction of the corresponding pIN-I and pIN-II plasmids.

There are also several options available in constructing pIN-III plasmids incorporating the B and C insertion sites. Assuming again that the corresponding pIN-I and pIN-II plasmids have already been constructed, each could be modified to insert the lacI gene fragment, according to the procedure of FIG. 29, or more preferably, the smaller Xba I-Eco RI fragment of pYM061 (pIN-III, A-1) could be replaced successively with the smaller Xba I-Eco RI fragments from each of the constitutive or inducible B site and C site plasmids, yielding, in either case, pIN-III B site and C site plasmids.

Most preferably, however, the pIN-III expression plasmids are constructed without first making the corresponding pIN-I or pIN-II plasmids. In the case of the B insertion site the B-1 pIN-III plasmid can be derived from plasmid pKEN221 by first digesting pKEN221 plasmid DNA with Fnu4H-1 restriction enzyme and then attaching Eco RI cohesive termini to the ends of the resulting fragment, according to the procedure described hereinabove and illustrated schematically at 138 in FIG. 17. The Eco RI fragment thus obtained can then be digested by Xba I restriction enzyme, splitting the fragment in two at the Xba I cleavage site located within the 5'-untranslated region. By purifying the smaller Xba I-Eco RI fragment thus obtained, and substituting it for the smaller Xba I-Eco RI fragment of pYM061 (pIN-III, A-1), the B-1 auto-regulated inducible cloning vehicle can be obtained. The resulting plasmid can then be further modified according to the scheme illustrated schematically at 141 in FIG. 18 and in FIG. 19, or according to the scheme shown schematically at 142 in FIG. 18 and in FIG. 20, to yield the pIN-III plasmids corresponding to the B-2 and B-3 reading frames, respectively.

An analogous course can be followed to obtain the pIN-III C site plasmids directly, without first constructing the corresponding pIN-I or pIN-II plasmids. Specifically, after digestion of pKEN111 plasmid DNA with Sau 3A restriction enzyme and attachment of Eco RI cohesive termini to the ends of the resulting fragment (according to the procedure described hereinabove and illustrated at 145 in FIG. 22), the Eco RI fragment thus obtained can then be digested with Xba I restriction enzyme, splitting the fragment in two at the Xba I cleavage site (located within the 5'-untranslated region). The Xba I-Eco RI fragment carrying the signal peptide region can then be inserted into the Xba I-Eco RI site of pYM061, resulting in the C-1 plasmid of pIN-III. Further modification of the plasmid DNA according to the procedure shown schematically at 148 in FIG. 23 and in FIG. 24, or according to the procedure illustrated schematically at 149 in FIG. 23 and in FIG. 25, yields the pIN-III plasmids corresponding to the C-2 and C-3 reading frames, respectively.

F. Construction of pIN-II(113) and pIN-III(113) Expression Plasmids

FIGS. 30A and 30B together illustrate schematically the manner in which an auto-regulated inducible plasmid cloning vehicle incorporating the A insertion site in the A-3 reading frame, and also utilizing the 113 bp lac promoter-operator fragment (rather than the 95 bp lac fragment) was constructed, and may be referred to in connection with the following more particularized discussion.

1. Construction of Plasmid pKM009

The first step in the construction of the A-3 expression plasmid of the pIN-III(113) series was to construct a plasmid to serve as a source of the 113 bp lac fragment in subsequent steps of the procedure. The plasmid chosen to receive the 113 bp lac fragment for this purpose was pKM005, a 9.9 Kb plasmid derived from pBR322 and carrying the lacZ and lacY structural genes, but no promoter with which to initiate their transcription, as shown schematically at 168 in FIG. 30A. This plasmid is obtainable from *E. coli* 4288 recA/pKM005, NRRL B-15395, which is available to the public from the permanent collection of the Northern Regional Research Laboratory, U.S. Department of Agriculture, Peoria, Ill., U.S.A. The plasmid can be obtained from NRRL B-15395 by conventional means.

The 113 bp lac promoter-operator fragment was derived from pKEN125, a 3.9 Kb plasmid which carries a rather lengthy (approximately 500 bp) portion of the natural *E. coli* lac promoter-operator region, as shown schematically at 169 in FIG. 30A. This plasmid is obtainable from *E. coli* JA221/F'lacIq/pKEN125, NRRL B-15235, which is available to the public from the permanent collection of the Northern Regional Research Laboratory, U.S. Department of Agriculture, Peoria, Ill., U.S.A. The plasmid can be obtained from NRRL B-15235 by conventional means.

In order to construct the plasmid vehicle to carry the 113 bp lac fragment, the following procedure was used: 10 micrograms of pKM005 plasmid DNA were digested to completion with 20 units of Xba I restriction enzyme in 100 microliters of Bam HI buffer at 37° C. for one hour. The reaction was terminated by phenol extraction, and the linearized DNAs were recovered by ethanol precipitation.

A 190 bp Hha I fragment (shown schematically at 170 in FIG. 30A) carrying the lac promoter-operator region (illustrated schematically by the saw-toothed segment at 171 in FIG. 30A and similarly in FIGS. 30B, 31A and 31B), was separately derived from pKEN125 as follows: 40 micrograms of pKEN125 plasmid DNA were digested with 40 units of Hha I restriction enzyme in 302 microliters of Hind III buffer at 37° C. for 1.5 hours. The 190 bp fragment was purified by 5% polyacrylamide gel electrophoresis in the following manner: the DNA fragments in the polyacrylamide gel were stained with ethidium bromide (one microgram/ml), and the band corresponding to the 190 bp fragment was cut out. The DNA fragments in this band were eluted from the gel using electrophoresis. Ethidium bromide was removed from the DNA fragments by phenol extraction, and the DNAs were recovered by ethanol precipitation.

In order to isolate still further the DNA segment within which the lac promoter-operator resides, the following procedure (indicated schematically at 172 in FIG. 30A) was used: one-half of the purified 190 bp Hha I DNA fragments obtained were digested with 7 units of Bst NI restriction enzyme in 50 microliters of Hae III buffer at 60° C. for one hour. Phenol extraction was performed, after which the DNAs were recovered by ethanol precipitation and dried under vacuum. After digestion with Bst NI restriction enzyme, the DNAs were then treated with 4 units of Klenow enzyme (obtained from New England Nuclear) in 50 microliters of Hind III buffer in the presence of a 40 μM mixture of deoxynucleotides (dATP, dGTP, dCTP, dTTP) at room temperature for 30 minutes to create blunt ends. After phenol extraction and ethanol precipitation, the DNA fragments were mixed with 400 pmoles of phosphorylated Xba I linker, and treated with 5 units of T4 DNA ligase in ligase buffer (total volume 30 microliters) containing 0.48 mM ATP at 12.5° C. for 16 hours. The reaction was terminated by diluting the mixture twelve-fold with Bam HI buffer and by heating the mixture at 60° C. for 10 minutes. Eighty units of Xba I restriction enzyme were added, and the mixture was then incubated at 37° C. for 2 hours to create Xba I cohesive termini. This reaction was terminated by phenol extraction, and the DNAs were recovered by ethanol precipitation.

One-fortieth of the DNA mixture thus obtained was mixed with 0.4 micrograms of the previously-linearized pKM005 plasmid DNA, and the Xba I cohesive termini were ligated with 20 units of T4 DNA ligase (obtained from New England Biolabs) in ligase buffer (total volume 20 microliters) containing 0.6 mM ATP at 12.5° C. for 16 hours. Ten microliters of the ligation mixture were thereafter used to transform *E. coli* strain 4288 recA, NRRL B-15397 (recA, mal24, spc12, supE-50, DE5 [Δlac, proB]). This strain is available to the public from the permanent collection of the Northern Regional Research Laboratory, U.S. Department of Agriculture, Peoria, Ill., U.S.A. The transformants were placed on the surface of a MacConkey agar plate containing 50 micrograms/ml of ampicillin. The ampicillin-resistant transformants yielding red colonies were selected, and one of the plasmid DNAs purified from those transformants had the structure shown at 173 in FIG. 30A. This plasmid, which carried a 113 bp Xba I fragment containing the lac promoter-operator, was designated pKM009.

2. Construction of Plasmid pYM153

The next step in the construction of the pIN-III(113), A-3 expression plasmid was to clone the 113 bp lac fragment in a plasmid which already carries the lpp promoter. The plasmid chosen for this purpose was pYM151, a 12.6 Kb plasmid carrying the lpp promoter as well as the lacZ and lacY structural genes and the entire lacI gene, as shown schematically at 174 in FIG. 30A. This plasmid is obtainable from *E. coli* W620 recA/pYM151, NRRL B-15396, which is available to the public from the permanent collection of the Northern Regional Research Laboratory, U.S. Department of Agriculture, Peoria, Ill., U.S.A. The plasmid can be obtained from NRRL B-15396 by conventional means.

In order to clone the 113 bp lac fragment, the following procedure was used: 2 micrograms of pYM151 plasmid DNA were digested to completion with 20 units of Xba I restriction enzyme in 100 microliters of Bam HI buffer at 37° C. for one hour. The reaction was terminated by phenol extraction, and the linearized DNAs were recovered by ethanol precipitation. In a separate reaction, 25 micrograms of pKM009 plasmid DNA were digested with 50 units of Xba I restriction enzyme and RNaseA in 400 microliters of Bam HI buffer at 37° C. for two hours. The 113 bp Xba I fragment containing the lac promoter-operator region was purified by 5% polyacrylamide gel electrophoresis in the same manner as described previously, and 0.014 micrograms of the 113 bp Xba I fragment were combined with 0.2 micrograms of the previously-linearized pYM151 plasmid DNA. The Xba I cohesive termini were annealed and the plasmid thereby re-circularized by treating the mixture with 20 units of T4 DNA ligase (obtained from New England Biolabs) in ligase buffer (total volume 10 microliters) containing 1.2 mM ATP at 12.5° C. for 16 hours. Ten microliters of the ligated mixture were used to transform *E. coli* strain 4288 recA, NRRL B-15397, and the transformants were placed on the surface of an L-broth plate containing 50 micrograms/ml of ampicillin and 40 micrograms/ml of X-gal. The transformants yielding white colonies were selected, and one of the plasmids purified from the ampicillin-resistant, white-colony transformants had the structure shown at 175 in FIG. 30B. This plasmid, which was found to have undergone multiple insertion of the 113 bp Xba I lac promoter-operator fragment, was designated pYM153.

3. Construction of Plasmid pYM071

The next step in the construction of the pIN-III, A-3 cloning vehicle was to join, in the same orientation, the region containing the tandem lpp promoter-multiple lac promoter-operator fragments, with a DNA segment containing the other necessary and desirable features of an auto-regulated inducible lpp gene cloning vehicle, described hereinabove. These are, specifically, the polynucleotide sequence at the exogenous DNA insertion site containing the recognition sequences for the Eco RI, Bam HI and Hind III restriction enzymes, the transcription terminator fragment of the lpp gene, and the intact, functional lacI gene. The source chosen for this DNA segment was pYM061, the pIN-III, A-1 expression plasmid, the construction of which was described hereinabove, and the structure of which is depicted schematically at 176 in FIG. 30B.

In order to combine these DNA sequences, the following procedure was used: 10 micrograms of pYM061 plasmid DNA were digested with 14 units of Pst I restriction enzyme in 250 microliters of Pst I buffer at 37° C. for 1.5 hours. To this solution, 36 microliters of 1M Tris:HCl (pH 7.5), 3.75 microliters of 0.1M $MgCl_2$, 13.75 microliters of 1M NaCl, 54 microliters of $H_2O$, one microgram/ml BSA (12.5 microliters), and 50 units of Eco RI restriction enzyme were added, and the mixture was incubated at 37° C. for two hours. A 6.3 Kb Eco RI-Pst I fragment was purified by 0.7% agarose gel electrophoresis in the same manner as described previously. This fragment is illustrated schematically at 177 in FIG. 30B.

Separately, 30 micrograms of pYM153 plasmid DNA were digested with 100 units of Eco RI restriction enzyme and RNaseA in 250 microliters of Eco RI buffer at 37° C. for one hour and fifty minutes. The reaction mixture was extracted with phenol and the DNA fragments were precipitated with 2.5 volumes of ethanol and dried under vacuum. The DNAs were then digested with 100 units of Pst I restriction endonuclease in 250 microliters of Pst I buffer at 37° C. for two hours. A 1.3 Kb Eco RI-Pst I fragment was purified by 0.7% agarose gel electrophoresis in the same manner as described previously. This fragment is illustrated schematically at 178 in FIG. 30B. The purified 1.3 Kb fragment (0.04 micrograms) was then mixed with 0.16 micrograms of the 6.3 Kb Eco RI-Pst I fragment previously obtained from pYM061, and the Pst I and Eco RI cohesive termini were annealed by treating the mixture with 20 units of T4 DNA ligase (obtained from New England Biolabs) in 20 microliters of ligase buffer containing 0.48 mM ATP at 12.5° C. for 16 hours. Ten microliters of the ligated mixture were used to transform *E. coli* strain W620 recA, NRRL B-15024, and one of the plasmid DNAs purified from the ampicillin-resistant transformants had the structure shown at 179 in FIG. 30B. This plasmid was designated pYM071.

4. Construction of Plasmid pYM072

The final step in the construction of the first auto-regulated inducible lpp gene cloning vehicle utilizing the 113 bp lac fragment was to eliminate the superfluous multiple 113 bp Xba I insert fragments in pYM071 (each fragment carrying a copy of the lac promoter-operator), so as to leave only one such fragment in the desired position downstream of the lpp promoter and upstream of the exogenous DNA insertion site.

To accomplish this result, 20 micrograms of pYM071 plasmid DNA were partially digested with 10 units of Xba I restriction enzyme in 100 microliters of Bam HI buffer at 37° C. for 40 minutes. The resulting Xba I fragments were purified by agarose gel electrophoresis in the same manner as described previously in order to obtain only those fragments with sizes in the range of approximately 7.4 Kb to 7.6 Kb. Since digestion with Xba I restriction enzyme results in the production of fragments with "sticky ends" at both termini, the purified DNA fragments (0.3 micrograms) were then treated with 4 units of Klenow enzyme in 75 microliters of Hind III buffer in the presence of a 5 μM mixture of deoxynucleotides (dATP, dGTP, dCTP, dTTP) at room temperature for 30 minutes to create blunt ends. Phenol extraction was performed and the DNAs were then recovered by ethanol precipitation.

The DNA fragments were blunt-end ligated and thereby re-circulated by treating with 2.5 units of T4 DNA ligase in 10 microliters of ligase buffer containing 0.6 mM ATP at 12.5° C. for 16 hours. Ten microliters of the ligated mixture were then used to transform *E. coli* strain W620 recA, NRRL B-15024, and the transformants were placed on the surface of L-broth plates containing 50 micrograms/ml of ampicillin. Twenty-four colonies were picked up, their plasmid DNAs were isolated, and restriction maps of those plasmids were examined. Two of them had the structure shown at 180 in FIG. 30B, and these plasmids were designated pYM072. Analysis of the DNA nucleotide sequence of pYM072 confirmed that this plasmid was the pIN-III(113), A-3 auto-regulated inducible cloning vehicle of the present invention.

5. Construction of Other pIN-II(113) and pIN-III(113) Expression Plasmids

It will be appreciated that the foregoing was the experimental procedure actually used in the first instance to construct an auto-regulated inducible expression plasmid, having the A-3 reading frame and utilizing the 113 bp lac promoter-operator fragment. It will also be apparent that there are several methods available, as disclosed hereinabove in connection with the pIN-II and pIN-III plasmids, with which to modify plasmid pYM072 to construct pIN-III(113) plasmids corresponding to the remaining A site reading frames and to all of the B site and C site reading frames, whether or not the counterpart pIN-III plasmids are available.

However, it will be understood by those skilled in the art that alternative and preferable methods exist with which to construct the pIN-III(113) expression plasmids, which also will yield the pIN-II(113) (inducible, but not auto-regulated) expression plasmids, if desired. These methods are depicted schematically in FIGS. 31A and 31B.

As shown at 181 and 182, respectively, in FIG. 31A, these methods require the availability of plasmid pKM009, the construction of which was described in detail hereinabove, to serve as a source of the 113 bp lac promoter-operator fragment, as well as the availability of plasmid pKEN037, also described hereinabove as the constitutive (pIN-I) A-1 cloning vehicle resulting from the prior research of one of the present inventors. Referring to the prior research, the procedure depicted schematically in FIG. 27 illustrates the manner in which the constitutive A-1 plasmid (pKEN037) can be made inducible by incorporating therein the 95 bp lac promoter-operator fragment. In an analogous fashion, the 113 bp lac fragment can be incorporated into pKEN037, yielding the pIN-II(113), A-1 inducible plasmid.

As illustrated in FIG. 31A, this can be accomplished by first digesting pKM009 plasmid DNA with Xba I restriction enzyme to obtain the 113 bp Xba I fragment carrying the lac promoter-operator, followed by insertion of that fragment at the Xba I cleavage site of pKEN037 and re-circularization with T4 DNA ligase to obtain the plasmid with the structure shown at 183 in FIG. 31A. This plasmid can then be modified to remove the Xba I cleavage site located upstream of the 113 bp lac fragment by partial digestion with Xba I restriction enzyme, followed by treatment with Klenow enzyme to create blunt ends and recirculization with T4 DNA ligase, as shown schematically at 184 in FIG. 31B. The resulting structure, which is illustrated at 185 in FIG. 31B, is the pIN-II(113), A-1 inducible expression plasmid, and is analogous to the inducible plasmid pKEN045 (pIN-II, A-1), carrying the 95 bp lac fragment, shown at 156 in FIG. 27. The other inducible pIN-II(113) plasmids incorporating the A insertion site in the A-2 and A-3 reading frames, as well as the plasmids incorporating the B and C insertion sites in all three reading frames, can then be prepared, if desired, in a manner directly analogous to that discussed hereinabove in connection with pKEN045 and the pIN-II plasmids.

However, because the plasmids of the pIN-III(113) series do not require the use of specialized *E. coli* strains as transformants and are therefore preferred for exogenous gene expression over those of the pIN-II(113) series, the foregoing scheme in turn suggests the preferred methods for constructing the pIN-III(113) plasmids. Both of these methods assume the availability of the pIN-II(113), A-1 plasmid whose structure is indicated at 185 in FIG. 31B. One of the preferred methods (not shown in the drawings) involves utilizing a course analogous to the procedures described hereinabove and illustrated in FIGS. 28 and 29, in which the lacI gene is inserted into the inducible pIN-II(113), A-1 plasmid shown at 185 in FIG. 31B, yielding the corresponding auto-regulated inducible expression plasmid of the pIN-III(113) series.

Another method which achieves the same result in fewer steps, and is therefore most preferred, is shown in FIG. 31B, and assumes the availability of plasmid pYM061 (illustrated at 186 in FIG. 31B), which was described hereinabove as the auto-regulated inducible (pIN-III) A-1 cloning vehicle resulting from the prior research of one of the present inventors. This most preferred method involves double digestion of pYM061 plasmid DNA with Eco RI and Pst I restriction enzymes to obtain the 6.3 Kb DNA fragment shown at 187 in FIG. 31B, as well as double digestion of the plasmid shown at 185 in FIG. 31B to yield the 1.1 Kb DNA fragment depicted at 188 in FIG. 31B, followed by mixture of those fragments and ligation of the mixture with T4 DNA ligase. This procedure results in the plasmid having the structure shown at 189 in FIG. 31B, which is the pIN-III(113), A-1 auto-regulated inducible expression plasmid, analogous to the auto-regulated inducible plasmid pYM061 (pIN-III, A-1) shown at 167 in FIG. 29.

Whichever of the methods described above is used to construct the plasmid shown at 189 in FIG. 31B, the other auto-regulated inducible pIN-III(113) plasmids incorporating the A insertion site in the A-2 and A-3 reading frames, as well as the plasmids incorporating the B and C insertion sites in all three reading frames, can then be prepared in a manner directly analogous to that discussed hereinabove in connection with pYM061 and the pIN-III plasmids.

A structural gene coding for a human hormone or other desired polypeptide can be expressed in transformed bacterial hosts using a recombinant plasmid cloning vehicle constructed in accordance with the present invention, and significant quantities of the desired polypeptide can be produced thereby. However, it will be apparent to those skilled in the art that the embodiments described herein are by way of illustration and not of limitation, and that other recombinant plasmid cloning vehicles with which exogeneous genes may be expressed may be utilized without departing from the spirit and scope of the present invention, as set forth in the appended claims.

We claim:

1. A recombinant plasmid suited for use as a cloning vehicle for expression of at least one polypeptide in a transformed bacterial host, said plasmid comprising a first DNA sequence comprising DNA coding for the promoter of the lipoprotein gene of *Escherichia coli*, linked in reading phase with (a) a second DNA sequence located downstream of said lipoprotein promoter and coding for the segment between positions −40 and +65 of the β-galactosidase promoter-operator of *Escherichia coli*, and (b) a third DNA sequence located downstream of said second DNA sequence and coding for the amino acid sequence of said at least one polypeptide, said plasmid also comprising a fourth DNA sequence coding for the lacI gene of *Escherichia coli*.

2. A plasmid in accordance with claim 1 wherein said first DNA sequence comprises DNA coding for the 5′-untranslated region of said lipoprotein gene, and wherein said second DNA sequence is located within said 5′-untranslated region.

3. A plasmid in accordance with claim 2 wherein said first DNA sequence comprises DNA coding for the 3′-untranslated region and the transcription termination signal of said lipoprotein gene.

4. A plasmid in accordance with claim 3 wherein said third DNA sequence is located downstream of said 5′-untranslated region and upstream of said 3′-untranslated region and upstream of said transcription termination signal.

5. A plasmid in accordance with claim 4 wherein said first DNA sequence further comprises DNA coding for a peptide extension capable of directing translocation of said at least one polypeptide across the cytoplasmic membrane of the bacterial host.

6. A plasmid in accordance with claim 5 wherein said third DNA sequence is located within the DNA coding for the peptide extension.

7. A plasmid in accordance with claim 5 wherein said third DNA sequence is located at the 3′ terminus of the DNA coding for the peptide extension.

8. A plasmid in accordance with claim 4 wherein said at least one polypeptide comprises a mammalian hormone.

9. A recombinant plasmid suited for use as a cloning vehicle for expression of at least one polypeptide in a transformed bacterial host, said plasmid comprising a first DNA sequence comprising DNA coding for the promoter and 5′-untranslated region and 3′-untranslated region and transcription termination signal of the lipoprotein gene of *Escherichia coli*, linked with (a) a second DNA sequence located downstream of said promoter and within said 5′-untranslated region and coding for the segment between positions −40 and +65 of the β-galactosidase promoter-operator of *Escherichia coli*, and (b) a third DNA sequence located downstream of said second DNA sequence and upstream of said 3′-untranslated region and upstream of said transcription termination signal and linked in reading phase with said first DNA sequence and with said second DNA sequence and coding for a translation initiation codon adjacent the recognition sequence of at least one restriction endonuclease for incorporation in said plasmid of the DNA sequence coding for the amino acid sequence of said at least one polypeptide, said plasmid also comprising a fourth DNA sequence coding for the lacI gene of *Escherichia coli*.

10. A plasmid in accordance with claim 5 wherein said first DNA sequence further comprises DNA coding for a polypeptide consisting of at least the first eight amino acid residues of and at most the entire amino acid sequence of the lipoprotein of *Escherichia coli*.

11. A plasmid in accordance with claim 10 wherein said third DNA sequence is located within the DNA coding for a polypeptide consisting of at least the first eight amino acid residues of and at most the entire amino acid sequence of the lipoprotein of *Escherichia coli*.

12. A plasmid in accordance with claim 9 wherein said first DNA sequence further comprises DNA coding for the peptide extension of the prolipoprotein of *Escherichia coli.*

13. A plasmid in accordance with claim 12 wherein said first DNA sequence further comprises DNA coding for the first eight amino acid residues of the lipoprotein of *Escherichia coli,* linked with and located immediately downstream of the DNA coding for said peptide extension.

14. A plasmid in accordance with claim 13 wherein said third DNA sequence is located at the 3' terminus of the DNA coding for the first eight amino acid residues of the lipoprotein of *Escherichia coli.*

15. A plasmid in accordance with claim 12 wherein said third DNA sequence is located within the DNA coding for said peptide extension.

16. A plasmid in accordance with claim 12 wherein said third DNA sequence is located at the 3' terminus of the DNA coding for said peptide extension.

17. A plasmid in accordance with claims 15, 16 or 14 wherein the insertion site comprises DNA sequences recognized by the Eco RI, Hind III and Bam HI restriction endonucleases.

18. A plasmid in accordance with claim 17 which is pYM072.

19. A recombinant plasmid suited for use as a cloning vehicle for expression of at least one polypeptide in a transformed bacterial host, said plasmid comprising a first DNA sequence comprising DNA coding for the promoter and 5'-untranslated region and 3'-untranslated region and transcription termination signal of the lipoprotein gene of *Escherichia coli,* linked with (a) a second DNA sequence located downstream of said promoter and within said 5'-untranslated region and coding for the segment between positions −40 and +65 of the β-galactosidase promoter-operator of *Escherichia coli,* and (b) a third DNA sequence located downstream of said second DNA sequence and upstream of said 3'-untranslated region and upstream of said transcription termination signal and linked in reading phase with said first DNA sequence and with said second DNA sequence and coding for a translation initiation codon adjacent the recognition sequence of at least one restriction endonuclease for incorporation in said plasmid of the DNA sequence coding for the amino acid sequence of said at least one polypeptide.

20. A method for producing a polypeptide in a transformed bacterial host comprising the steps of (a) selecting a recombinant plasmid comprising a first DNA sequence including DNA coding for the promoter and 5'-untranslated region and 3'-untranslated region and transcription termination signal of the lipoprotein gene of *Escherichia coli,* linked with (i) a second DNA sequence located downstream of said promoter and within said 5'-untranslated region and coding for the segment between positions −40 and +65 of the β-galactosidase promoter-operator of *Escherichia coli,* and (ii) a third DNA sequence located downstream of said second DNA sequence and upstream of said 3'-untranslated region and upstream of said transcription termination signal and linked in reading phase with said first DNA sequence and with said second DNA sequence and coding for a translation initiation codon adjacent the recognition sequence of at least one restriction endonuclease for incorporation in said plasmid of the DNA sequence coding for the amino acid sequence of said polypeptide, said plasmid also comprising a fourth DNA sequence coding for the lacI gene of *Escherichia coli,* (b) inserting said DNA sequence coding for the amino acid sequence of said polypeptide within said third DNA sequence, (c) inserting the plasmid in said bacterial host by transformation, (d) isolating and culturing said bacterial host to produce a large population of said bacterial host, (e) adding to said population a lactose inducer, and (f) producing said polypeptide from said population.

21. A method for producing a polypeptide in a transformed bacterial host comprising the steps of (a) selecting a recombinant plasmid including a first DNA sequence comprising DNA coding for the promoter and 5'-untranslated region and 3'-untranslated region and transcription termination signal of the lipoprotein gene of *Escherichia coli,* linked with (i) a second DNA sequence located downstream of said promoter and within said 5'-untranslated region and coding for the segment between positions −40 and +65 of the β-galactosidase promoter-operator of *Escherichia coli,* and (ii) a third DNA sequence located downstream of said second DNA sequence and upstream of said 3'-untranslated region and upstream of said transcription termination signal and linked in reading phase with said first DNA sequence and with said second DNA sequence and coding for a translation initiation codon adjacent the recognition sequence of at least one restriction endonuclease for incorporation in said plasmid of the DNA sequence coding for the amino acid sequence of said polypeptide, (b) inserting said DNA sequence coding for the amino acid sequence of said polypeptide within said third DNA sequence, (c) inserting the plasmid in said bacterial host by transformation, (d) isolating and culturing said bacterial host to produce a large population of said bacterial host, and (e) producing said polypeptide from said population.

22. A transformant comprising a plasmid comprised of a first DNA sequence comprising DNA coding for the promoter and 5'-untranslated region and 3'-untranslated region and transcription termination signal of the lipoprotein gene of *Escherichia coli,* linked with (a) a second DNA sequence located downstream of said promoter and within said 5'-untranslated region and coding for the segment between positions −40 and +65 of the β-galactosidase promoter-operator of *Escherichia coli,* and (b) a third DNA sequence located downstream of said second DNA sequence and upstream of said 3'-untranslated region and upstream of said transcription termination signal and linked in reading phase with said first DNA sequence and with said second DNA sequence and coding for a translation initiation codon adjacent the recognition sequence of at least one restriction endonuclease for incorporation in said plasmid of the DNA sequence coding for the amino acid sequence of a polypeptide, said plasmid also comprising a fourth DNA sequence coding for the lacI gene of *Escherichia coli,* said transformant being capable of producing the polypeptide upon fermentation in an aqueous nutrient medium containing assimilable sources of carbon, nitrogen and inorganic substances, and also containing a lactose inducer.

23. The transformant of claim 22 wherein the transformant is selected from the species *Escherichia coli.*

24. The transformant of claim 23 which is *E. coli* W620 recA/pyM072.

25. A transformant comprising a plasmid comprised of a first DNA sequence comprising DNA coding for the promoter and 5'-untranslated region and 3'-untranslated region and transcription termination signal of the lipoprotein gene of *Escherichia coli*, linked with (a) a second DNA sequence located downstream of said promoter and within said 5'-untranslated region and coding for the segment between positions −40 and +65 of the β-galactosidase promoter-operator of *Escherichia coli*, and (b) a third DNA sequence located downstream of said second DNA sequence and upstream of said 3'-untranslated region and upstream of said transcription termination signal and linked in reading phase with said first DNA sequence and with second DNA sequence and coding for a translation initiation codon adjacent the recognition sequence of at least one restriction endonuclease for incorporation in said plasmid of the DNA sequence coding for the amino acid sequence of a polypeptide, said transformant being capable of producing the polypeptide upon fermentation in an aqueous nutrient medium containing assimilable sources of carbon, nitrogen and inorganic substances.

* * * * *